United States Patent
Pedersen et al.

(10) Patent No.: US 10,731,151 B2
(45) Date of Patent: Aug. 4, 2020

(54) METHOD FOR SYNTHESISING TEMPLATED MOLECULES

(71) Applicant: NUEVOLUTION A/S, Copenhagen (DK)

(72) Inventors: Henrik Pedersen, Bagsvaerd (DK); Anette Holtmann, Ballerup (DK); Thomas Franch, Copenhagen N. (DK); Alex Haahr Gouliaev, Veksoe Sjaelland (DK); Jakob Felding, Charlottenlund (DK)

(73) Assignee: NUEVOLUTION A/S, Copenhagen (DK)

( * ) Notice: Subject to any disclaimer, the term of this patent is extended or adjusted under 35 U.S.C. 154(b) by 889 days.

(21) Appl. No.: 14/340,123

(22) Filed: Jul. 24, 2014

(65) Prior Publication Data
US 2015/0252360 A1  Sep. 10, 2015

Related U.S. Application Data

(63) Continuation of application No. 12/179,323, filed on Jul. 24, 2008, now Pat. No. 8,808,984, which is a continuation of application No. 10/507,121, filed as application No. PCT/DK03/00172 on Mar. 14, 2003, now Pat. No. 7,413,854, which is a continuation-in-part of application No. 10/175,539, filed on Jun. 20, 2002, now Pat. No. 7,727,713, and a continuation-in-part of application No. PCT/DK02/00419, filed on Jun. 20, 2002.

(60) Provisional application No. 60/364,056, filed on Mar. 15, 2002, provisional application No. 60/389,885, filed on Jun. 20, 2002, provisional application No. 60/409,968, filed on Sep. 12, 2002.

(30) Foreign Application Priority Data

Mar. 15, 2002 (DK) .................................. 2002 0415
Jun. 20, 2002 (DK) ................................ 2002 00952
Sep. 12, 2002 (DK) ................................ 2002 03147

(51) Int. Cl.
*C12N 15/10* (2006.01)
*C07H 21/04* (2006.01)

(52) U.S. Cl.
CPC ......... *C12N 15/1068* (2013.01); *C07H 21/04* (2013.01); *C07B 2200/11* (2013.01)

(58) Field of Classification Search
None
See application file for complete search history.

(56) References Cited

U.S. PATENT DOCUMENTS

| | | | |
|---|---|---|---|
| 4,599,303 A * | 7/1986 | Yabusaki | C12Q 1/6816 435/6.11 |
| 4,822,731 A | 4/1989 | Watson et al. | |
| 4,914,210 A * | 4/1990 | Levenson | C07C 43/11 536/25.3 |
| 5,013,830 A | 5/1991 | Ohtsuka et al. | |
| 5,047,519 A | 9/1991 | Hobbs, Jr. et al. | |
| 5,432,272 A | 7/1995 | Benner | |
| 5,449,613 A | 9/1995 | Dordick et al. | |
| 5,451,503 A | 9/1995 | Hogan et al. | |
| 5,473,060 A | 12/1995 | Gryaznov et al. | |
| 5,474,796 A | 12/1995 | Brennan | |
| 5,476,930 A | 12/1995 | Letsinger et al. | |
| 5,503,805 A | 4/1996 | Sugarman et al. | |
| 5,571,677 A | 11/1996 | Gryaznov | |
| 5,571,903 A | 11/1996 | Gryaznov | |
| 5,573,905 A | 11/1996 | Lerner et al. | |
| 5,604,097 A | 2/1997 | Brenner | |
| 5,635,400 A | 6/1997 | Brenner | |
| 5,639,603 A | 6/1997 | Dower et al. | |
| 5,646,265 A | 7/1997 | McGee | |
| 5,654,413 A | 8/1997 | Brenner | |
| 5,656,739 A | 8/1997 | Cubicciotti | |
| 5,663,046 A | 9/1997 | Baldwin et al. | |
| 5,665,975 A | 9/1997 | Kedar et al. | |

(Continued)

FOREIGN PATENT DOCUMENTS

DE  196 46 372 C1  6/1997
DE  196 42 751 A1  4/1998

(Continued)

OTHER PUBLICATIONS

Blondal et al., "Isolation and characterization of a thermostable RNA ligase 1 from a Thermus scotoductus bacteriophage TS2126 with good single-stranded DNA ligation properties", Nucl. Acids. Res. 2005, vol. 33, No. 1, pp. 135-142.

Brennan & Gumport, "T4 RNA ligase catalyzed synthesis of base analogue-containing oligodeoxyribonucleotides and a characterization of their thermal stabilities", Nucleic Acids Res., 1985, vol. 13, No. 24, pp. 8665-8684.

Cummins et al., "Characterization of fully 2'-modified oligoribonucleotide hetero- and homoduplex hybridization and nuclease sensitivity", Nucl. Acids Res. 1995, vol. 23, No. 11, pp. 2019-2024.

(Continued)

*Primary Examiner* — Christopher M Gross
(74) *Attorney, Agent, or Firm* — Merchant & Gould P.C.

(57) ABSTRACT

The invention relates to a method for synthesising templated molecules attached to the templated which directed the synthesis thereof. The method involves a template, a scaffold functional entity and a functional entity attached to a building block, which, in turn, is attached the template. The scaffold functional entity and the functional entity of the building block are both provided with complementary dimerization domains allowing the functional entities to come into close proximity when the complementary domains interact with to each other. The method may be used for generating libraries of templated molecules which may be selected for biological activity.

47 Claims, 21 Drawing Sheets

Specification includes a Sequence Listing.

(56) References Cited

U.S. PATENT DOCUMENTS

| | | |
|---|---|---|
| 5,670,633 A | 9/1997 | Cook et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A | 3/1998 | Lerner et al. |
| 5,739,314 A | 4/1998 | Roy et al. |
| 5,739,386 A | 4/1998 | Holmes |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargill et al. |
| 5,780,613 A | 7/1998 | Letsinger et al. |
| 5,789,162 A | 8/1998 | Dower et al. |
| 5,789,172 A | 8/1998 | Still et al. |
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov et al. |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller et al. |
| 5,948,648 A | 9/1999 | Khan et al. |
| 6,001,579 A | 12/1999 | Still et al. |
| 6,036,587 A | 3/2000 | Tolles et al. |
| 6,056,926 A | 5/2000 | Sugarman et al. |
| 6,060,596 A | 5/2000 | Lerner et al. |
| 6,087,112 A | 7/2000 | Dale |
| 6,090,912 A | 7/2000 | Lebl et al. |
| 6,096,875 A | 8/2000 | Khan et al. |
| 6,127,533 A | 10/2000 | Cook et al. |
| 6,132,970 A | 10/2000 | Stemmer |
| 6,140,489 A | 10/2000 | Brenner |
| 6,140,493 A | 10/2000 | Dower et al. |
| 6,140,497 A | 10/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar et al. |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,281,344 B1 | 8/2001 | Szostak et al. |
| 6,287,765 B1 | 9/2001 | Cubicciotti |
| 6,297,053 B1 | 10/2001 | Stemmer |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 | 6/2012 | Freskgard et al. |
| 2002/0048760 A1 | 4/2002 | Drmanac et al. |
| 2002/0055125 A1 | 5/2002 | Charych et al. |
| 2002/0072887 A1 | 6/2002 | Szalma et al. |
| 2002/0081714 A1 | 6/2002 | Jain et al. |
| 2002/0115068 A1 | 8/2002 | Tomlinsen et al. |
| 2002/0127598 A1 | 9/2002 | Zhou et al. |
| 2002/0142335 A1 | 10/2002 | Strittmatter |
| 2003/0004122 A1 | 1/2003 | Beigelman et al. |
| 2003/0050453 A1 | 3/2003 | Sorge |
| 2003/0113738 A1 | 6/2003 | Liu et al. |
| 2003/0182068 A1 | 9/2003 | Battersby et al. |
| 2003/0186233 A1 | 10/2003 | Chesnut et al. |
| 2003/0187240 A1 | 10/2003 | Cook et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197804 A1 | 10/2004 | Keefe et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu |
| 2005/0042669 A1 | 2/2005 | Liu et al. |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard |

FOREIGN PATENT DOCUMENTS

| | | |
|---|---|---|
| EP | 0 324 616 A3 | 7/1989 |
| EP | 0 542 770 A1 | 5/1993 |
| EP | 0 604 552 A1 | 7/1994 |
| EP | 0 604 552 B1 | 7/1994 |
| EP | 0 643 778 A1 | 3/1995 |
| EP | 0 695 305 A1 | 2/1996 |
| EP | 0 766 826 A1 | 4/1997 |
| EP | 0 773 227 A1 | 5/1997 |
| EP | 0 776 330 A2 | 6/1997 |
| EP | 0 778 280 A2 | 6/1997 |
| EP | 0 830 363 A1 | 3/1998 |
| EP | 0 879 219 A1 | 11/1998 |
| EP | 0 962 527 A1 | 12/1999 |
| EP | 1 324 045 A2 | 7/2003 |
| EP | 1 402 024 A2 | 3/2004 |
| EP | 1 483 585 A1 | 12/2004 |
| EP | 1 514 938 A1 | 3/2005 |
| EP | 1 533 385 A1 | 5/2005 |
| EP | 1 828 381 A2 | 9/2007 |
| EP | 1 832 567 A2 | 9/2007 |
| EP | 2 305 808 A1 | 4/2011 |

(56) References Cited

FOREIGN PATENT DOCUMENTS

| | | |
|---|---|---|
| JP | 2004-535193 A | 11/2004 |
| JP | 2008-000268 A | 1/2008 |
| JP | 05292967 B2 | 9/2013 |
| WO | 90/05785 A1 | 5/1990 |
| WO | 1991/05058 A1 | 4/1991 |
| WO | 1991/19818 A1 | 12/1991 |
| WO | 1992/00091 A1 | 1/1992 |
| WO | 1992/02536 A1 | 2/1992 |
| WO | 1992/22875 A1 | 12/1992 |
| WO | 93/03172 A1 | 2/1993 |
| WO | 1993/03172 A1 | 2/1993 |
| WO | 1993/06121 A1 | 4/1993 |
| WO | 1993/20242 A1 | 10/1993 |
| WO | 1994/08051 A1 | 4/1994 |
| WO | 1994/13623 A1 | 6/1994 |
| WO | 1994/024143 A1 | 10/1994 |
| WO | 1995/04160 A1 | 2/1995 |
| WO | 1995/06293 A1 | 3/1995 |
| WO | 1995/12608 A1 | 5/1995 |
| WO | 1996/03418 A1 | 2/1996 |
| WO | 1996/09316 A1 | 2/1996 |
| WO | 1996/11878 A1 | 4/1996 |
| WO | 1996/12014 A1 | 4/1996 |
| WO | 1996/24061 A1 | 8/1996 |
| WO | 1996/24847 A1 | 8/1996 |
| WO | 1996/35699 A1 | 11/1996 |
| WO | 1996/40201 A1 | 12/1996 |
| WO | 1996/41011 A1 | 12/1996 |
| WO | 1997/04131 A1 | 2/1997 |
| WO | 1997/11958 A1 | 4/1997 |
| WO | 1997/19039 A1 | 5/1997 |
| WO | 1997/27317 A1 | 7/1997 |
| WO | 1997/35198 A1 | 9/1997 |
| WO | 1998/01562 A1 | 1/1998 |
| WO | 1998/56904 A1 | 6/1998 |
| WO | 1998/31700 A1 | 7/1998 |
| WO | 1998/47613 A1 | 10/1998 |
| WO | 1998/56904 A1 | 12/1998 |
| WO | 1998/58256 A1 | 12/1998 |
| WO | 1999/42605 A1 | 8/1999 |
| WO | 1999/51546 A1 | 10/1999 |
| WO | 1999/51773 A1 | 10/1999 |
| WO | 1999/64378 A2 | 12/1999 |
| WO | 00/023458 A1 | 4/2000 |
| WO | 2000/20639 A1 | 4/2000 |
| WO | 2000/21909 A2 | 4/2000 |
| WO | 2000/23456 A1 | 4/2000 |
| WO | 2000/23458 A1 | 4/2000 |
| WO | 2000/24882 A1 | 5/2000 |
| WO | 2000/32823 A1 | 6/2000 |
| WO | 2000/40695 A2 | 7/2000 |
| WO | 2000/47775 A1 | 8/2000 |
| WO | 2000/61775 A1 | 10/2000 |
| WO | 2001/00876 A1 | 1/2001 |
| WO | 2001/07657 A1 | 2/2001 |
| WO | 2001/53539 A1 | 7/2001 |
| WO | 2001/56955 A1 | 8/2001 |
| WO | 2001/90414 A1 | 11/2001 |
| WO | 2002/03067 A1 | 1/2002 |
| WO | 2002/10186 A1 | 2/2002 |
| WO | 2002/34948 A2 | 5/2002 |
| WO | 2002/40664 A1 | 5/2002 |
| WO | 2002/074929 A2 | 9/2002 |
| WO | 2002/074978 A2 | 9/2002 |
| WO | 2002/083951 A1 | 10/2002 |
| WO | WO2002090581 | 11/2002 |
| WO | 2002/099078 A2 | 12/2002 |
| WO | 2002/102820 A1 | 12/2002 |
| WO | 2002/103008 A2 | 12/2002 |
| WO | 2003/025567 A1 | 3/2003 |
| WO | 2003/062417 A1 | 7/2003 |
| WO | 2003/076943 A1 | 9/2003 |
| WO | 2003/078050 A2 | 9/2003 |
| WO | 2003/078416 A1 | 9/2003 |
| WO | 2003/078445 A2 | 9/2003 |
| WO | 2003/078446 A2 | 9/2003 |
| WO | 2003/078625 A2 | 9/2003 |
| WO | 2003/078626 A2 | 9/2003 |
| WO | 2003/078627 A2 | 9/2003 |
| WO | 2003/082901 A2 | 10/2003 |
| WO | 2003/106679 A1 | 12/2003 |
| WO | 2004/001042 A2 | 12/2003 |
| WO | 2004/007529 A2 | 1/2004 |
| WO | 2004/009814 A1 | 1/2004 |
| WO | 2004/013070 A2 | 2/2004 |
| WO | 2004/016767 A2 | 2/2004 |
| WO | 2004/024929 A2 | 3/2004 |
| WO | 2004/039825 A2 | 5/2004 |
| WO | 2004/039962 A2 | 5/2004 |
| WO | 2004/042019 A2 | 5/2004 |
| WO | 2004/056994 A2 | 7/2004 |
| WO | 2004/074429 A2 | 9/2004 |
| WO | 2004/074501 A2 | 9/2004 |
| WO | 2004/083427 A2 | 9/2004 |
| WO | 2004/099441 A2 | 11/2004 |
| WO | 2004/110964 A2 | 12/2004 |
| WO | 2005/003778 A2 | 1/2005 |
| WO | 2005/008240 A2 | 1/2005 |
| WO | 2005/026387 A1 | 3/2005 |
| WO | 2005/058479 A2 | 6/2005 |
| WO | 2005/078122 A2 | 8/2005 |
| WO | 2005/090566 A2 | 9/2005 |
| WO | 2005/116213 A2 | 12/2005 |
| WO | 2006/048025 A1 | 5/2006 |
| WO | 2006/053571 A2 | 5/2006 |
| WO | 2006/069063 A1 | 6/2006 |
| WO | 2006/079061 A2 | 7/2006 |
| WO | 2006/128138 A2 | 11/2006 |
| WO | 2006/130669 A2 | 12/2006 |
| WO | 2006/133312 A2 | 12/2006 |
| WO | 2006/135654 A2 | 12/2006 |
| WO | 2006/135786 A2 | 12/2006 |
| WO | 2006/138560 A2 | 12/2006 |
| WO | 2006/138666 A2 | 12/2006 |
| WO | 2007/008276 A2 | 1/2007 |
| WO | 2007/011722 A2 | 1/2007 |
| WO | 2007/016488 A2 | 2/2007 |
| WO | 2007/053358 A2 | 5/2007 |
| WO | 2007/062664 A2 | 6/2007 |
| WO | 2007/124758 A1 | 11/2007 |
| WO | 2008/014238 A2 | 1/2008 |
| WO | 2008/036273 A2 | 3/2008 |
| WO | 2008/054600 A2 | 5/2008 |
| WO | WO2008/094599 | 8/2008 |
| WO | 2009/018003 A2 | 2/2009 |
| WO | 2009/077173 A2 | 6/2009 |
| WO | 2009/152824 A1 | 12/2009 |
| WO | 2011/127933 A1 | 10/2011 |

OTHER PUBLICATIONS

Inoue et al., "Synthesis and hybridization studies on two complementary nona(2'-O-methyl)ribonucleotides", Nucleic Acids Res. 1987, vol. 15, No. 15, pp. 6131-6148.
Lesnik et al., "Oligodeoxynucleotides containing 2'-O-modified adenosine: Synthesis and effects on stability of DNA:RNA duplexes", Biochemistry, 1993, vol. 32, pp. 7832-7838.
Tessier et al., "Ligation of single-stranded oligodeoxyribonucleotides by T4 RNA ligase", Anal. Biochem., 1986, vol. 158, pp. 171-178.
Uhlenbeck and Gumport, The Enzymes, "T4 RNA ligase", 1982, vol. XV, pp. 31-58.
Verma et al., "Functional tuning of nucleic acids by chemical modifications: tailored oligonucleotides as drugs, devices, and diagnostics", Chem Rec. 2003, 3(1), pp. 51-60.
Communication (office action) by the European Patent Office dated Mar. 24, 2016 in relation to European Patent Application No. 10741877.4.
Glen Research (Catalogue No. 10-1014-XX)—Mar. 8, 2005 + Material Safety Data Sheet on Catalogue No. 10-1014-xx—Sep. 11, 2004.
Glen Research (Catalogue No. Oct. 1054-XX)—Mar. 8, 2005 + Material Safety Data Sheet on Catalogue No. 10-1054-xx—Oct. 28, 2004.

(56) References Cited

OTHER PUBLICATIONS

Glen Research (Catalogue No. 10-1092-XX)—Apr. 28, 2005 + Material Safety Data Sheet on Catalogue No. 10-1092-xx—Oct. 28, 2004.
Glen Research (Catalogue No. 10-1590-XX)—Aug. 21, 2008 + Further Info on 10-1590-xx—Dec. 12, 2008.
Han et al., "Quantum-dot-tagged microbeads for multiplexed optical coding of biomolecules", Nature Biotechnology, 2001, vol. 19, pp. 631-635.
Korshun et al., "5-(1-Pyrenylethynyl)-2'-Deoxyuridine, A N Ovel Fluorescent Nucleosideanalog", Bioorganiceskaa himia, 22(12), 1996, pp. 923-925. (English abstract only).
Mullah et al., "Efficient synthesis of double dye-labeled oligodeoxyribonucleotide probes and their application in a real time PCR assay", Nucleic Acids Research, 1998, vol. 26, No. 4, pp. 1026-1031.
Needels et al., "Generation and screening of an oligonucleotide-encoded synthetic peptide library", Proc. Natl. Acad. Sci. USA, 1993, vol. 90, pp. 10700-10704.
Nielsen et al., "Synthetic Methods for the Implementation of Encoded Combinatorial Chemistry", J. Am. Chem. Soc., 1993, vol. 115, 9812-9813, 1993 with supplementary Materials (pp. 1-7).
Thelwell, "Mode of action and application of Scorpion primers to mutation detection", Nucleic Acids Research, 2000, vol. 28, No. 19, pp. 3752-3761.
Third Party observation filed with the European Patent Office on Mar. 14, 2016 in relation to European Patent Application No. 10741877.4 (X-Chem Inc.).
Wagner, "Gene inhibition using antisense oligodeoxynucleotides", Nature, 1994, vol. 372, pp. 333-335.
Wagner, "Antisense gene inhibition by oligonucleotides containing C-5 propyne pyrimidines", Science, 1993, vol. 260, pp. 1510-1513.
Yamana et al., "Synthesis and Binding Properties of Oligonucleotides Containing an Azobenzene Linker", Nucleosides & Nucleotides, 1998, vol. 17, No. 1-3, pp. 233-242.
Zammatteo et al., "Amination of polystyrene microwells: Application to the covalent grafting of DNA probes for hybridization assays", Analytical Biochemistry, 236, pp. 85-94, 1996.
Abravaya et al. "Detection of point mutation with a modified ligase chain reaction (GAP-LCR)", Nucleic Acids Research, vol. 23, No. 4, 675-682 (1995).
Acevedo et al., "Non-enzymatic transcription of an oligonucleotide 14 residues long", J. Mol. Biol. 1987, 1978, p. 187-193.
Acevedo et al., "Template-directed oligonucleotide ligation on hydroxylapatite"; Nature vol. 321, Jun. 19, 1986, p. 790-792.
Acinas et al. "PCR-Induced Sequence Artifacts and Bias: Insights from Comparison of Two 16S rRNA Clone Libraries Constructed from the same Sample", Applied and Environmental Microbiology, vol. 71, No. 12, 8966-8969, (2005).
Adang et al., "The Contribution of Combinatorial Chemistry to Lead Generation: An Interim Analysis", Current Medicinal Chemistry, 2001, 8, 985-998.
Affleck, "Solutions for library encoding to create collections of discrete compounds", Chemical Biology, 2001, 5:257-263.
Agarwal, et al. "Total Synthesis of the gene for an alanine transfer ribonucleic acid from yeast", Abstract only, Nature, 227, 27-34 (1970).
Albagli D et al. "Chemical amplification (CHAMP) by a continuous, self-replicating oligonucleotide-based system" J. Am. Chem. Soc. 1999, 121, 6954-6955, Pub. on the web Jul. 14, 1999.
Albagli, et al., "Chemical amplification (CHAMP) by a continuous, self-replicating oligonucleotide-based system", J. Am. Chem. Soc., vol. 121, pp. 6954-6955, 1999.
Anonymous. "5,6-Dihydro-Pyrimidines, 2'-Phosphoramidites", Glen Research Report, vol. 10, 11 (Dec. 1997 issue).
Anonymous. "Cytofectin GSV Transfection Protocol", Glen Research Report, vol. 10, 4-6 (Dec. 1997 issue).
Anonymous. "DCI—A Logical Alternative Aviator", Glen Research Report, vol. 10, No. 1 (1997).
Anonymous. "More Novel Monomers-4-Thio-dU, 5'-Amino-dT, 2'-F-Pyrimidines", Glen Research Report, vol. 10, 10 (Dec. 1997 issue).
Anonymous. "New Fluorescent Reagents—Tamra CPG, Fluorescein-dt", Glen Research Report, vol. 10, 7 (Dec. 1997 issue).
Anonymous. "Non-enzymatic Ligation of Single-Stranded and Duplex DNA", Glen Research Report, vol. 10, 12 (Dec. 1997 issue).
Anonymous. "Preparing Oligonucleotides for Antisensen Experiments", Glen Research Report, vol. 10, 3 (Dec. 1997 issue).
Anonymous. "Q-Supports Reduce Cleavage Time to 2 Minutes", Glen Research Report, vol. 10, 9 (Dec. 1997 issue).
Anonymous. "Universal Support Replaces Individual Columns", Glen Research Report, vol. 10, 8 (Dec. 1997 issue).
Australian Patents Act 19909—Section 32 Regulation 3.6, (Request for a Determination of Dispute between Applicants) and 3.7 Applications to Commissioner for Declaration of an Eligible Person, (2005).
Bain et al., "Biosynthetic Site-Specific Incorporation of a Non-Natural Amino Acid into a Polypeptide", J. Am. Chem. Soc., 1989, 111, 8013-8014.
Bain et al., "Regioselective Ligation of Oligoribonucleotides using DNA Splints", Nucl. Acids Res., vol. 20, No. 16, 4372, 1992.
Baldwin, "Design, Synthesis and use of binary encoded synthetic chemical libraries", Molecular Diversity, 2, 81-88 (1996).
Baldwin, et al. "Synthesis of a Small Molecule Combinatorial Library Encoded with Molecular Tags", J. Am. Chem. Soc. 117, 5588-5589 (1995).
Balkenhohl et al., "Combinatorial Synthesis of Small Organic Molecules", Angew Chem Int. Ed Engl. 1996, 35, pp. 2288-2337.
Baran et al. "Total synthesis of Marine natural products without using protecting groups", Nature, vol. 446, 404-408 (2007).
Barany, "Genetic disease detection and DNA amplification using cloned thermostable ligase", Proc. Natl. Acad., vol. 88, 189-193 (1991).
Barany "The ligase chain reaction in a PCR world", Genome Res. vol. 1, 5-16 (1991).
Barany "The Taq1 star reaction: strand preferences reveal hydrogen-bond donor and acceptor sites in canonical sequence recognition", Gene vol. 65 149-165 (1988).
Barnes et al., "Recent developments in the encoding and deconvolution of combinatorial libraries", Chemical Biology 2000, 4:346-350.
Battersby, et al. "Optical encoding of micro-beads of gene screening: alternatives to micro-arrays", Drug Discovery Today, vol. 6, supp 1, p. 519-526 (Jun. 1, 2001).
Bayer et al. "Liquid Phase Synthesis of Peptides", Nature vol. 237; 30 (Jun. 1972).
Benner "Expanding the genetic lexicon; incorporating non-standard amino acids into proteins by ribosome-based synthesis", Trends Biotechnol. May 1994; 12(5): 158-63.
Berger et al. "Universal bases for hybridization, replication and chain termination", Nucleic acids research, Oxford University Press, vol. 28, No. 15, pub. Aug. 1, 2000, p. 2911-2914.
Bittker, et al. "Nucleic Acid Evolution and Minimization by Non-homologous Random Recombination", Nature Biotechnology 20, 1024-1029 (2002).
Bittker, et al., "Recent advances in the in vitro evolution of nucleic acids", Curr Opin Chem Biol., vol. 6(3), pp. 367-374, Jun. 2002.
Bittker et al. "Recent advances in the in vitro evolution of nucleic acids". Curr Opin Chem Biol. Jun. 2002;6(3):367-74. Review. Pub. on the web Mar. 20, 2002.
Boger & Goldberg, "Chapter 10: Multi-step Solution Phase Combinatorial Synthesis" in Combinatorial Chemistry, ed. Hicham Fenniri, Oxford University Press (Oxford, England), 2000, pp. 303-326.
Böhler et al., "Template switching between PNA and RNA oligonucleotides", Nature 1995. 376, 578-581.
Bonora, et al. "Large Scale, PEG-supported DNA Synthesis"; Nucleosides & Nucleotides, 10(1-3), (1991).
Borman, "Combinatorial chemists focus on small molecules, molecular recognition, and automation", Chemical & Engineering News, Feb. 12, 1996.
Braasch, et al. "Locked nuckic acids (LNA): fine-tuning the recognition of DNA and RNA", Elsevier, Chemistry & Biology, 9, 1-7 (2001).

(56) References Cited

OTHER PUBLICATIONS

Braun, et al., "DNA-templated assembly and electrode attachment of a conducting silver wire". Nature, vol. 391. Feb. 19, 1998, 775-778.
Brennan, et al. "Using T4 RNA Ligase with DNA Substrates", Methods in enzymology, vol. 100, pp. 38-52. (1983).
Brenner et al., "Encoded combinatorial chemistry", Proceedings of the National Academy of Sciences of USA, National Academy of Science, (Jun. 1, 1992), vol. 89, No. 12, pp. 5381-5383.
Broude "Stem-loop oligonucleotides: a robust tool for molecule biology and biotechnology", Trends in Biotechnology, vol. 20, No. 6, Jun. 2002 (22-06) pp. 249-256.
Bruce Smith and Markus Krummenacker "DNA-guided assembly of proteins as a pathway to an assembler" (http://www.wadsworth.org/albcon97/abstract/krummena.htm) The 1997 Albany Conference: Biomolecular Motors and Nanomachines.
Bruick et al. "Template-directed ligation of peptides to oligonucleotides" Chemistry and Biology, vol. 3, No. 1 Jan. 1996, p. 49-56.
Bruick et al. "A simple procedure for constructing 5'-amino-terminated oligodeoxynucleotides in aqueous solution" Nucleic Acids Res. Mar. 15, 1997; 25(6):1309-10.
Bruick et al. "Template-Directed Ligation of Peptides to Oligonucleotides," Chemistry and Biology 1996, vol. 3 No. 1.
Buller, et al., "Design and synthesis of a novel DNA-encoded chemical library using Diels-Alder cycloadditions", Bioorg Med Chem Lett 18, 5926 (2008).
Buller, et al. "Discovery of TNF inhibitors from an DNA-encoded chemical library based on Diels-Alder cycloaddition", Chem Biol 16, 1075 (2009).
Buller et al., "Drug Discovery with DNA-Encoded Chemical Libraries", Bioconjugate Chem., vol. 21 (9), pp. 1571-1580, (2010).
Bunin et al., "[26] Synthesis and Evaluation of 1,4-Benzodiazepine Libraries," Methods in Enzymology, vol. 267, pp. 448-465, (1996).
Bunin, et al. "The combinatorial synthesis and chemical and biological evaluation of a 1,4-benzodiazepine library", Proc. Natl. Acad. Sci. USA, vol. 91, pp. 4708-4712 (May 1994).
Buskirk, et al. "Engineering a Ligand-Dependent RNA Transcriptional Activator", Chem. Biol. 11, 1157-1163 (2004), This work is featured in a Research Highlight in Nature Methods 1, 6-7 (2004).
Calderone, et al., "Directing otherwise incompatible reactions in a single solution by using DNA-templated organic synthesis", Angew Chem Int Ed., 2002, vol. 41, No. 21. 4104-4108.
Canne et al. "Chemical Protein Synthesis by Solid Phase Ligation of Unprotected Peptide Segments", J. Am. Chem. Soc., 121, 8720-8727 (1999).
Chan et al., "Intra-tRNA distance measurements for nucleocapsid protein-dependent tRNA unwinding during priming of HIV reverse transcription", PNAS vol. 96, p. 459-464, Jan. 1999.
Chen, et al. "Enzyme Engineering for Nonaqueous Solvents: Random Mutagenesis to Enchance Activity of Subtilisin E in Polar Organic Media"; Bio/Technology 9, 1073-1077 (1991)—Abstract.
Chen, et al. "Enzymes in Nonaqueous Solvents: Applications in Carbohydrate and Peptide Preparation", Methods in Biotechnology, vol 15, 373-374 (2001).
Chen et al., "Total Synthesis of Naturally Occurring Prostaglandin F2a on a Non-Cross-Linked Polystyrene Support", Tetrahedron Letters,39, (1998), 3943-3946.
Chen et al., "Template-directed synthesis on Oligodeoxycylidylate and Pulydeoxycylidylate templates" J. Mol. Biol. 1985, 181, 271.
Cheng et al., "Novel Solution Phase Strategy for the Synthesis of Chemical Libraries Containing Small Organic Molecules", J. Am. Chem. Soc., vol. 118, 2567-2573, 1996.
Chorghade, "Drug Discovery and Development", 2006, ISBN-13: 978-0-471-39848-6, Published by John Wiley & Sons, Inc., Hoboken, New Jersey.
Chu et al. "Ligation of oligonucleotides to nucleic acids or proteins via disulfide bonds." Nucleic Acids Research. vol. 16. No. 9, pp. 3671-3691 (1998).
Clark et al., "Design, Synthesis and Selection of DNA-encoded Small-molecules Libraries", Nat. Chem. Biol., vol. 5, No. 9, 647-772, 2009.
Clark "Selecting chemicals: the emerging utility of DNA-encoded libraries", Molecular Discovery Research, GlaxoSmithKline, Waltham, MA, USA. Current Opinion in Chemical Biology, 14(3), 396-403, (2010).
Coe et al., "Solution-phase combinatorial chemistry", Molecular Diversity, 4:31-38, 1999.
Colombo et al. "Synthesis of lenein-enkephalin and methionineenkephalin . . . ", Hoppe-Seyler's Z.Physiol.Chem. vol. 363 (1981).
Constantino, L et al. "Privleged structures as leads in medicinal chemistry", Curr Med Chem 13, 65, (2006).
Cotton, et al. "Reactivity of cytosine and thymine in single-base-pair mismatches with hydroxylamine and osmium tetroxide and its application to the study of mutations", Proc Natl Acad Sci (USA), 85, 4397-401 (1988).
Cousins et al., "Identification and Isolation of a Receptor for N-Methyl Alkylammonium Salts: Molecular Amplification in a Pseudo-peptide Dynamic Combinatorial Library". Angew. Chem. Int. Ed., 2001, 40. No. 2. 423-427.
Curran, "Strategy-Level Separations in Organic Synthesis: From Planning to Practise", Angew. Chem. Int. Eb., vol. 37, 1174-1196, 1998.
Czarnik, et al. "Encoding methods for combinatorial chemistry", Current Opinion in Chemical Biology, vol. 1. ISS 1, p. 60-66 (Jun. 1997).
Czarnik "Encoding strategies in combinatorial chemistry", Proc. Natl. Acad. Sci. USA, vol. 94, pp. 12738-12739 (Nov. 1997).
Czlapinski etal. "Nucleic acid template-directed assembly of metallosalen-DNA conjugates," J. Am. Chem Sco., Sep. 5, 2001: 123(35):8618-9 published on the web Aug. 10, 2001.
Declaration by Dr. Dennis Benjamin (including curriculum vitae), (2013).
Degn, et al. "Enzyme Activity in Organic Solvent as a Function of Water Activity Determined by Membrane Inlet Mass Spectrometry"; Biotechnology Technique vol. 6; No. 2; pp. 161-164 (Mar./Apr. 1992).
Denapoli, et al. "PEG-supported Synthesis of Cylic Oligodeoxyribonucleotides", Nucleosides & Nucleotides, vol. 12, No. 1 (1993).
"The Development of Amplifiable and Evolvable Unnatural Molecules", David R. Liu, Harvard Univ. Cambridge MA Dept of Chemistry and Chemical Biology, Report dated Aug. 4, 2003, No. A104614, approved for public release.
"DNA Phosphoramidites & CPG's"; http://www.qualitysystems.com.tw/proligo/dna%20phosphoamidites%20&%20cpg's.htm Dec. 2, 2010.
Dewitt SH et al., "Diversomers": an approach to nonpeptide, nonoligomeric chemical diversity. Proc. Natl. Acad. Sci, USA, vol. 90, pp. 6909-6913, Aug. 1993.
DNA-templated synthesis as a basis for the evolution of synthetic molecules. Liu DR. Gartner ZJ, Kanan MW, Calderone CT Abstracts of Papers of the American Chemical Society 225:612-ORGN, Part 2, Mar. 2003.
"DNA-Templated Functional Group Transformations Enable Sequence-Programmed Synthesis Using Small-Molecule Reagentes" Sakurai, K.; Snyder, T.M.; Liu, D.R. J. Am. Chem, Soc. 127. 1660-1661 (2005).
"DNA-Templated Organic Synthesis: Nature's Strategy for Controlling Chemical Reactivity Applied to Synthetic Molecules" Li, X.; Liu, D.R. Angew. Chem. Int. Ed. 43, 4848-4870 (2004).
"DNA-Templated Organic Synthesis and Selection of a Library of Macrocycles" Gartner, Z.J.; Tse, B.N.; Grubina, R.; Doyon J.B., Snyder, T.M.; Liu, D.R. Science 305, 1601-1605 (2004).
"Dokl Akad Nauk SSSR", vol. 258, 1242-1245, Krynetskya NF Tumanov YV (1981).
Dolinnaya, et al. "Chemical ligation as a method for the assembly of double-stranded nucleic acids: Modifications and local structure studies", Russian Chemical Bulletin, vol. 45, No. 8 (1996).

(56) References Cited

OTHER PUBLICATIONS

Dolinnaya, et al. "Structural and kinetic aspects of chemical reactions in DNA duplexes. Information on DNA local structure obtained from chemical ligation data", Nucleic Acids Research, vol. 19, No. 11, 3073-3080 (1991).
Dolle, "Comprehensive Survey of Combinatorial Library Synthesis: 2000", Journal of Combinatorial Chemistry, 2001, vol. 3, No. 6, pp. 477-517.
Dolle, "Comprehensive Sutvey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Douglas, et al., "Polymer-supported solution synthesis of oligosaccharides", J. Am. Chem. Soc., vol. 113 (1991).
Dower, et al., "In vitro selection as a powerful tool for the applied evolution of proteins and peptides". Current Opinion in Chemical Biology, 2002, 6:390-398.
Doyon, et al. "Highly sensitive in vitro selections for DNA-linked synthetic small molecules with protein binding affinity and specificity", J. Am. Chem. Soc, Sep. 16, 2003, pp. 1-2 and S1-S8.
Drabovich, et al. "Selection of Smart Small-Molecule Ligands: the Proof of Principle", Analytical Chemistry, vol. 81, No. 1, 490-494 (2009).
Drews "Drug Discovery: A Historical Persnective", Science vol. 287, pp. 1960-1964 (2000).
Dreyer, et al. "Enzyme Catalysis in Nonaqueous Media: Past, Present and Future" in Patel (ed.), "Biocatalysis in the Pharmaceutical and Biotechnology Industries", 819-820 (2006).
Ecker, et al. "Rational screening of oligonucleotide combinatorial libraries for drug discovery", Nucleic Acids Research, vol. 21, No. 8, pp. 1853-1856 (1993).
Elghaniam, et al. "Selective colorimetric detection of polynucleotides based on the distance-dependent optical properties of gold nanoparticles", Science, vol. 277, Aug. 22, 1997.
Eliman, et al. "Biosynthetic method for introducing Unnatural Amino acids site specifically into proteins". Methods Enzymol. 202, 301-336 (1992).
Ellman et al., "Biosynthetic method for introducing Unnatural Amino acids site specifically into proteins". Methods Enzymol, 202, 302-225 (1992).
Fack, et al. "Heteroduplex mobility assay (HMA) pre-screening: An improved strategy for the rapid identification of inserts selected from phage-displayed peptide libraries", Molecular Diversity, vol. 5, No. 1; pp. 7-12 (2000).
Fegan et al. "Rigid cyanhie dye nucleic acid labels", Chem Common May 7; (17) 2004-6 (2008).
Ficht, et al. "As Fast and Selective as Enzymatic Ligations: Upaired Nucleobases Increase the Selectivity of DNA-Controlled Native Chemical PNA Ligation"; ChemBioChem: vol. 6, Issue 11, pp. 2098-2103 (2005).
"Finding reactions nt a haystack: Try'em all, see what works" Meeting American Chemical Society, Sep. 10, 2004, vol. 305, Science. Brenner, Sydney and Richard A. Lerner. "Encoded Combinatorial Chemistry," Proc. Natl. Acad. Sci, USA, vol. 89, pp. 5381-5383, Jun. 1992.
Fredriksson, et al. "Protein detection using proximity-dependent DNA ligation assays", Nature Biotechnology, vol. 20, p. 473-477 (May 2002).
Frutos AG et al., "Demonstration of a word design strategy for DNA computing on surfaces", Nucleic Acids Research, 1997, vol. 25, No. 23, 4748-4757.
Frutos et al. "Enzymatic Ligation Reactions of DNA 'Words' on Surfaces for DNA Computing", J. Am. Chem. Soc., vol. 120, No. 40, 10277-10282, 1998.
Fujimoto et al. "Template-directed photoreversible ligation of deoxyoligonucleotides via 5-Vinyldeoxyurideine" J. Am. Soc. 2000, 122, 5646-5647.
Fujimoto, et al., "Template-directed reversible photocircularization of DNA via 5-vinyldeoxycytidine", Tetrahedron Letters, vol. 41:33, pp. 6451-6454, 2000.
Fujimoto, et al., "Template directed photochemical synthesis of branched oligodeoxynucleotides via 5-carboxyvinyldeoxyuridine", Tetrahedron Letters,vol. 41:49, pp. 9437-9440, 2000.
Furka, A, "Combinatorial Chemistry: 20 years on . . . ", Drug Discovery today vol. 7, No. 1, p. 1-4 (2002).
Furka, et al. "Combinatorial Libraries by Portioning and Mixing", Combinatorial Chemisuy & High Throughput Screening, 2, 105-122 (1999).
Furka et al., "General method fbr rapid synthesis of multicomponent peptide mixtures", Int. J. Peptide Proieln Res., 37, 1991, 487-493.
Furlan, Rle et al. "Molecular amplification in a dynamic combinatorial library using non-covalent interactions". Chem. Commum., 2000. 1761-1762.
Gait, "Chapter 1: An Introduction to Modern Methods of DNA Synthesis",Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gallop et al., "Applications of Combinatorial Technologies to Drug Discovery, 1. Background and Peptide Combinatorial Libraries", Journal of Medicinal Chemistry, 1994, vol. 37, No. 9, pp. 1233-1251.
Gartner et al., "Expanding the Reaction Scope of DNA-Templated Synthesis", Angew. Chem. Int. Ed., vol. 41, No. 10, 1796-1800, 2002.
Gartner Z.J et al., "The generality of DNA-templated synthesis as a basis for evolving non-natural small molecules", Journal of the American Society, (Jul. 18, 2001), vol. 23, No. 28, pp. 6961-6963.
Gartner, ZJ et al., Two enabling architectures for DNA-templated organic synthesis, Angew. Chem. Int. Ed. 2003, vol. 42, No. 12, 1370-1375.
Gartner, Z.J. et al., "Multistep small-molecule synthesis programmed by DNA templates". J. Am. Chem. Soc. vol. 124, No. 35 2002. 10304-10306 (including, Supporting Information, pp. 1-4), (2002).
Gartner, et al., "Expanding the reaction scope of DNA-templated synthesis", Angew Chem. Int. Ed., vol. 41, No. 10, pp. 1796-1800, 2002.
Geysen, et al. "Combinatorial Compound Libraries for Drug Discovery: An Ongoing Challenge", Nature Reviews, Drug Discovery, vol. 2, p. 222-223, (Mar. 2003).
Giebel, L.B. et al. "Screening of Cyclic Peptide Phage Libraries Identifies Ligands That Bind Streptavidin with High Affinities", Biochemistry: vol. 34, No. 47; 15430-15435, (1995).
Glen Research Report, "Advances in RNA Synthesis and Structural Analysis", vol. 11, No. 2, Dec. 1998.
Gordon, EM et al., "Applications of combinatorial technologies to drug discovery. 2. Combinatorial organic synthesis, library screening strategies, and future directions". Journal of Medicinal Chemistry, vol. 37, No. 10, May 13, 1994.
Gorin, et al., "Reactivity-Dependent PCR: Direct, Soiution-Phase in Vitro Selection for Bond Formation", J. Am. Chem. Soc. 131, pp. 9189-9191 (2009).
Grange, et al. "Detection of point mutations in type I collagen by RNase digestion of RNA/RNA hybrids", Nucleic Acids Research 18: 4227-36 (1990).
Gruen, et al., "An In Vivo Selection System for Homing Endonuclease Activity", Nucleic Acids Research 30, e29 (2002).
Gryaznov SM, Letsinger RL. "Template controlled coupling and recombination of oligonucleotide blocks containing thiophosphoryl groups". Nucleic Acids Res. Mar. 25, 1993; 21(6):1403-8.
Gryaznov SM, Schultz R, Chaturvedi SK, Letsinger RL. "Enhancement of selectivity in recognition of nucleic acids via chemical autoligation". Nucleic Acids Res. Jun. 25, 1994; 22(12):2366-9.
Gryaznov, et al., "Chemical Ligation of oligoratcleotides in the presence and absence of a template", J. Amer. Chem. Sco., vol. 115, pp. 3808-3809, 1993.

(56) References Cited

OTHER PUBLICATIONS

Guillen Schlippe et al., "In Vitro Selection of Highly Modified Cyclic Peptides That Act as Tight Binding Inhibitors", J. Am. Chem. Soc., 2012, 134, 10469-10477.
Gumport, et al. "T4 RNA Ligase as a Nucleic Acids Synthesis and Modification Reagent", Elsevier North Holland, Inc., 314-345 (1981).
Guo, et al. "Preparation of Encoded Combinatorial Libraries for Drug Discovery", Methods in Molecular Biology, Combinatorial Library Methods and Protocols, pp. 23-29 (2002).
Halpin et al., DNA display I. Sequence-encoded routing of DNA populations. PLoS Biol. Jul. 2004; 2(7)E173, Epub Jun. 22, 2004.
Halpin et al., DNA display II. Genetic manipulation of combinatorial chemistry libraries for small-molecule evolution. PLoS Biol. Jul. 2004; 2(7)E174, Epub Jun. 22, 2004.
Halpin et al., DNA display III. Solid-phase organic synthesis on unprotected DNA. PLoS Biol. Jul. 2004; 2(7)E175, Epub Jun. 22, 2004.
Han et al., "Liquid-phase combinatorial synthesis", Proc. Natl. Acad. Sci. USA, vol. 92, pp. 6419-6423, Jul. 1995.
Hansen, M. "A Yoctoliter-scale DNA reactor for small-molecule evolution", J Am Chem Soc. 131, 1322 (2009).
Harada, et al. "In vitro selection of optimal DNA substrates for t4 RNA ligase", Proc. Natl. Acad. Sci. USA, vol. 90, pp. 1576-1579 (Feb. 1993).
Harada "In vitro selection of optimal DNS substrates for ligation by a water-soluble carbodiimide", J Mol Evol., 38, 6, 558-560 (1994).
Harada, et al. "Unexpected substrate specificity of T4 DNA ligase revealed by in vitro selection", Nucleic Acids Research, vol. 21, No. 10, 2287-2291 (1993).
Harrison et al., "Synthesis and Hybridization Analysis of a Small Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Herpin, et al. "Synthesis of a 1000 member 1, 5-Benzodiazepine-2-one Library by the Directed Sorting Method", J. Comb. Chem., 2, 513-521 (2000).
Herrlein MK, Letsinger RL. "Selective chemical autoligation on a double-stranded DNA template". Nucleic Acids Res. Nov. 25, 1994; 22(23):5076-8.
"Highly Sensitive In Vitro Selections for DNA-Linked Synthetic Small Molecules with Protein Binding Affinity and Specificity" Doyon J.B.; Snyder, T.M.; Liu D.R. J. Am. Chem. Soc. 125. 12372-12373 (2003).
Higgins, et al. "Addition of Oligonucleotides to the 5'-Terminus of DNA by T4 RNA Ligase", Nucleic Acids Research, 6(3): 1013-1024 (1979).
Higgins, et al. "DNA-joining Enzymes: A Review", Methods in Enzymology, vol. 68, pp. 50-71 (1979).
Hill et al., "Diels-Alder Bioconjugation of Diene-Modified Oligonucleotides", J. Org. Chem., vol. 66, 5352-5358, 2001.
Hinton, et al. "T4 RNA Ligase Joins 2'-Deoxyribonucleoside 3', 5'-Bisphosphates to Oligodeoxyribonucleotides", Biochemistry vol. 17, No. 24, pp. 5091-5097 (1978).
Holmes, CP "Model Studies for New o-Nitrobenzyl Photolabile Linkers: Substituent Effects on the Rates of Photochemical Cleavage", J. Org. Chem. 62, 2370-2380 (1997).
Housby, et al. "Fidelity of DNA ligation: a novel experimental approach based on the polymerisation of libraries of oligonucleotides", Nucleic Acids Research, vol. 26, No. 18, pp. 4259-4266 (1998).
Hsu "Detection of DNA point mutations with DNA mismatch repair enzymes" Carcinogencsis 15:1657-62 (1994).
Inoue et al., Oligomerization of (Guanosine 5'phosphor-)-2-methylimidazolide on Poly(C), J. Mol. Biol. (1982), 162, 201-217.
Inoue et al., "A nonenzymatic RNA polymerase model", Science 1983, 219. p. 859-862.
Itakura et al., "Expression in *Escherichia coli* of a Chemically Synthesized Gene for the Hormone Somatostatin", Science, vol. 198, 1056-1063, 1977.
Ito et al. Tag-reporter and Resin Capture ± Release Strategy in Oligosaccharide Synthesis. Chemistry—A European Journal 8(14):3077-3084 (2002).
James, et al. "The Fidelity of Template-Directed Oligonucleotide Ligation and the Inevitability of Polymerase Function", Origins of Life and Evolution of the Biosphere 29, Kluwer Academic Publishers; pp. 375-390, (1999).
Janda, "Tagged Versus Untagged Libraries: Methods for the Generation and Screening of Combinatorial Chemical Libraries," PNAS USA, vol. 91, 10779-10785, Nov. 1994.
Jäschke, et al. "Evolution of DNA and RNA as catalysts for chemical reactions"; Current Opinion in Chemical Biology 4; pp. 257-262 (2000).
Jäschke, et al. "Synthesis and properties of oligodeoxyribonucleotide-polyethylene glycol conjugates", Nucleic Acids Research, vol. 22, No. 22, pp. 4810-4817 (1994).
Jones, et al. "Enzymes in organic synthesis 22. Effects of organic solvents on horse liver alcohol dehyrogense-catalyzed reduction"; Can. J. Chem. 60 pp. 335-338 (1982).
Kahn, "DNA-ligases": http://adnadn.umd.edu/biochem/kahn/molmachines/replication/DNA%20ligase.htm downloaded Dec. 10, 2009.
Kanagawa, "Bias and Artifacts in Multitemplate Polymerase Chain Reactions (PCR)," Journal of Bioscience and Bioengineering, vol. 96, No. 4, pp. 317-323 (2003).
Kanan, et al. "Reaction Discovery Enabled by DNA-Templated Synthesis and In Vitro Selection", Suppletmentary Information, pp. 1-20. (2004).
Kanan et al. "Reaction discovery enabled by DNA-templated synthesis and in vitro selection" Nature, vol. 431, Sep. 30, 2004, pp. 545-549.
Keiler, et al., "Role of peptide tagging system in degradation of proteins synthesized from damaged messenger RNA", Journal of Biological Chemistry, vol. 243, No. 6, pp. 1012-1015, 1968.
Keiler et al. "Role of a peptide tagging system in degradation of proteins synthesized from damaged messenger RNA", Science. Feb. 16, 1996; 271(52521):990-3.
Kelemen et al., "Hypersensitive Substrate for Ribonucleases", Nucl. Acids. Res., vol. 27, No. 18, 3696-3701, 1999.
Kerr, et al. "Encoded Combinatorial Peptide Libraries Containing Non-Natural Amino Acids", J. Am. Chem. Sco. 115, 2529-2531 (1993).
Kempe et al., Chemical and Enzymatic Biotin-labeling of Oligodeoxyribonucleotides, Nucl. Acids Res., vol. 13, No. 1, 45-57, 1985.
Kinoshita, et al. "Enzymatic Synthesis of Code Regions for Encoded Combinatorial Chemistry", Nucleic Acids Symposium Series, 34: 201-202 (1995).
Kinoshita et al., "Enzymatic Synthesis of Sequencing Primers Based on a Library of Tetramers", Chem. Express, No. 2, 149-152, 1992.
Kinoshita et al., "Strand Ligation in a Double-Stranded DNA by T4 RNA Ligase", Department of Functional Materials Science, Saitama University, Urawa, Japan. Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Kleiner et al., "Small-molecule discovery from DNA-encoded chemical libraries", Chem. Soc. Rev., 2011, 40, pp. 5707-5717.
Klekota B et al., "Selection of DNA-Binding Compounds via Multistage Molecular Evolution". Tetrahedron 55 (1999) 11687-11697.
Klibanov, "Why are enzymes less active in organic solvent than water?"; Trends in Biotechnology; vol. 15, Issue 3, 97-101; 1 (Mar. 1997)—Abstract.

(56) References Cited

OTHER PUBLICATIONS

Koivunen, E. et al. "Phage Libraries Displaying Cyclic Peptides with Different Ring Sizes: Ligand Specificities of the RGD-Directed Integrins", Bio/Technology: vol. 13, 265-270, (1995).
Krishna, "Developments and trends in enzyme catalysis in nonconventional media", Biotechnology Advances; vol. 20; Issues 3-4; pp. 239-267 (Nov. 2002)—Abstract.
Krug, et al. "Reversal of T4 RNA Ligase", Biochemistry vol. 21, No. 8, pp. 1858-1864 (1982).
Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.
Kurz, M et al. Psoralen photo-crosslinked mRNA-puromycin conjugates; a novel template for the rapid and facile preparation of mRNA-protein fusions. Nucleic Acids Res. Sep. 15, 2000; 28(18):E83.
Kurz et al. "cDNA—protein fusions: covalent protein—gene conjugates for the in vitro selection of peptides and proteins", Chembiochem—A European Journal of Chemical Biology, Wiley VCH, Weinheim, DE, vol. 2, No. 9, pp. 666-672, XP002332971, ISSN: 1439-4227 (Sep. 3, 2001).
Ladner, R.C. "Constrained peptides as binding entities", Elsevier Science Ltd., Trends in Biotechnology: vol. 13, 426-430, (1995).
Lebl, "Parallel Personal Comments on "Classical" Papers in Combinatorial Chemistry", J. Comb. Chem. I, pp. 3-24 (1999).
Lehman, I.R. "DNA ligase: Structure, Mechanism, and Function; The joining of DNA chains by DNA ligase is an essential component of DNA repair, replication, and recombination", Science vol. 186; pp. 790-797 (1974).
Leitzel JC, Lynn DG "Template-directed ligation: from DNA towards different versatile templates". Chem Rec. 2001; 1(1):53-62. Published online Jan. 30, 2001.
Leitzel, et al., "Template-directed ligtion: from DNA towards different versatile templates", Chem Rec., vol. 1(1), pp. 53-62, 2001.
Letsinger et al., "Chemical igation of oligonucleotides in the presence and absence of a template". J. Amer. Chem. Soc. 1993, 115, 3808-9.
Letsinger et al "Chemical and photochemical ligation of oligonucleotide blocks". Nucleosides and nucleotides. 16(5&6), 643-652 (1997).
Lewis et al "Ligation of oligonucleotides by pyrimidine dimers—a missing 'link' in the origin of life?" Nature, 298(5872):393-6 (Jul. 22, 1982).
Li et al., "Steroselectivity in DNA-templated organic synthesis and its origins", J. Am. Chem. Soc., vol. 125, No. 34, 2003,10188-10189.
Li et al., "DNA-catalyzed polymerization," J. Am. Chem. Soc. , Feb. 6, 2002; 124(5):746-7.
Li et al., "Kinetics of RNA Degradation by Specific Base Catalysis of Transesterificatioin Involving the 2'-Hydroxyl Group", J. Am. Chem. Soc., 1999, 121, pp. 5364-5372.
"Ligase", Answers.com: http://www.answers.com/topic/ligase, [accessed Dec. 10, 2009].
Lim et al. "Synthesis of DNA Dumbbells: Chemical vs. Enzymatic Ligation of Self-Complementary Oligonucleotides", Abstract only, Nucleotides and Nucleic Acids; vol. 16, Issue 1 & 2 pp. 41-51 (Jan. 1997).
Lindström, et al. "An orthogonal oligonucleotide protecting group strategy that enables assembly of repetitive or highly structured DNAs"; Nucleic Acids Research 30(19), e101; 2002 Oxford University Press (Oct. 1, 2002).
Lipinski et al., "Experimental and computational approaches to estimate solubility and permeability in drug discovery and development settings", Adv. Drug Deliv. Rev., vol. 46, 2001, pp. 3-26.
Lipinski, "Lead- and drag-like compounds: the rule-of-five revolution", Drug Discovery Today: Technologies, vol. 1, No. 4, 2004, pp. 337-341.

Liu et al., "Engineering a tRNA and aminoacyl-tRNA synthetase for the site specific incorporation of unnatural amino acids into proteins in vivo". Proc Natl Acad Sci U S A. Sep. 16, 1997; 94(19): 10092-7.
Liu D. "Expanding the reaction scope of DNA-templated synthesis Angew". Chem. Int. Ed. 2002, 41, No. 10 pp. 1796-1800. Published May 15, 2002.
Liu et al. "Progress toward the evolution of an organism with an expanded genetic code", Proc Natl Acad Sci USA. Apr. 27, 1999; 96(9):4780-5.
Liu et al "Template-directed photoligation of oligodeoxyribonucleotides via 4-thiothymidine", Nucleic Acids Res., Jul. 1, 1998, 26(13)33-34.
Liu et al "Template-directed photoligation of oligodeoxyribonucleotides via 4-thiothymidine", Nucleic Acids Res. Jul. 1, 1998; 26(13):3300-4.
Liu et al., "Optimized synthesis of RNA-protein fusions for in vitro protein selection". Methods Enzymol. 2000; 318:268-93.
Liu, "The Chemistry of Molecular Evolution," website of Dr. D.R. Liu, Publicly available Oct. 15, 2000. http://web.archive.org/web/20001015144553/http://evolve.havard.edu.
Liu, "The Chemistry and Chemical Biology of Molecular Evolution," website of Dr. D.R. Liu, publicly available Mar. 1, 2001, http://web.archive.org/web/20010301175107/http://evolve.havard.edu.
Liu, "The Chemistry and Chemical Biology of Molecular Evolution," website of Dr. D.R. Liu, publicly available Nov. 20, 2002. http://web.archive.org/web/20021129131743/http://evolve.havard edu.
Liu, "The Chemistry and Chemical Biology of Molecular Evolution," website of Dr. D.R. Liu, publicly available Oct. 15, 2003. http://web.archive.org/web/20031216020734/http://evolve.havard edu.
Liu "The Chemistry and Chemical Biology of molecular Evolution", Liu Group Research Summary from the website of Professor David R. Liu, obtained from the website in Feb. 2005.
Liu, et al. "Denaturing high performance liquid chromatography (DHPLC) used in the detection of germline and somatic mutations", Nucleic Acids Research, vol. 26, pp. 1396-1400 (1998).
Liu, "Development of Amplifiable and Evolvable Unnatural Molecules", website of Dr. D. R. Liu, publicly available Mar. 11, 2000. http://web.archive.org/web/20000311112631/http://evolve.havard.edu.
Lobanov Trends in Biotechnology, vol. 20, No. 2, pp. 86-87 (Feb. 2002).
Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).
Loughlin, "Biotransformations in organic synthesis"; Bioresource Technology 74, pp. 49-62 (2000).
Lowe, et al. "Combinatorial Libraries for Studying Molecular Recognition", URL: iupac.org.symposia/proceedings/phuket97/lowe.html, downloaded in Jun. 2005.
Loweth, CJ et al., "DNA-based assembly of gold nanocrystals", Angew. Chem. Int. Ed. 1999, 1808-1812.
Luebke et al. "Nonenzyme ligation of double-helical DNA by alternate-strand triple helix formation"; Nucleic Acids Research; vol. 20, No. 12; pp. 3005-3009 (1992).
Luo, P et al., "Analysis of the structure and stability of a backbone-modified oligonucleotide: implications for avoiding product inhibition in catalytic template-directed synthesis". J. Am. Chem. Soc. 1998, 120, 3019-3031.
Luther, A. et al., "Surface-promoted replication and exponential amplification of DNA analogues". Nature, vol. 396, No. 19, 1998, 245-248.
Ma et al., "In vitro selection of Unnatural Cyclic Peptide Libraries via mRNA Display", Book Ribosome Display and Related Technologies, ch. 21, pp. 367-390, (2003).
Maclean et al., "Glossary of Terms Used in Combinatorial Chemistry", Pure Appl. Chem., vol. 71, No. 12, pp. 2349-2365, 1999.
Maclean et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).
Magliery, et al. "Expanding the Genetic Code In Vitro and In Vivo", The Genetic Code and the Origin of Life, Ed. Ribas de Pouplana, L. Landes Bioscience, in Press (2004).

(56) References Cited

OTHER PUBLICATIONS

Makara et al. "Improving Success rates for lead generation using affinity binding technologies", Current Opinion in Biotechnology 16:666-673 (2005).
Mannocci, "DNA-Encoded affinity maturation libraries", Proc Natl Acad Sci USA 105, 17670 (2008).
Mannocci "DNA-Encoded Chemical Libraries", Diss ETH No. 18153 (2009).
Margulies et al., "Genome sequencing in microfabricated high-density picolitre reactors", Nature 437, 376 (2005).
Mashal, et al. "Detection of mutations by cleavage of DNA heteroduplexes with bacteriophage resolvases", Nature Genetics 9:177-83 (1995).
Matsuda, et al. "Low Fidelity DNA Synthesis by Human DNA Polymerase•?", Nature, 404: 1011-1013 (Apr. 27, 2000).
Matsuura K. et al., "Construction of glycol-clusters by self-organization of site-specifically glycosylated oligonucleotides and their cooperative amplification of lectin-recognition.", Journal of the American Chemical Society, (Jan. 17, 2001), vol. 123, No. 2, pp. 357-358.
McCoy, et al. "T4 Ribonucleic Acid Ligase Joins Single-Strand Oligo(deoxyribonucleotides)", Biochemistry vol. 19, No. 4, 635-642 (1980).
McGregor, et al. "Interaction-Dependent PCR: Identification of Ligand-Target Pairs from Libraries of Ligands and Libraries of Targets in a Single Solution-Phase Experiment", J. Am. Chem. Soc. 132, pp. 15522-15524 (2010).
Meier et al, "Combinatorial Methods, Automated Synthesis and High-Throughput Screening in Polymer Research: the Evolution Continues", Macromol. Rapid Commun., 2004, 25, 21-33.
Melkko et al. "Lead discovery by DNA-encoded chemical libraries", Drug Discovery Today. vol. 12, No. 11/12, pp. 465-471 (Jun. 2007).
Mendel, D. "Site-directed mutagenesis with an expanded genetic code". Annu. Rev. Biophys, Biomol. Struc. 1995. 24:435-62.
Mendel, D. "Site-directed mutagenesis with an expanded genetic code". Annu. Rev. Biophys, Biomol. Struc. 1995. 24:463-93.
Miller "DNA as a template for reaction discovery", Nature Biotechnology, vol. 22, No. 11, pp. 1378-1379 (Nov. 2004).
Millward, S.W. et al. "A General Route for Post-Translational Cyclization of mRNA Display Libraries", Journal of the American Chemical Society: vol. 127, 14142-14143, (2005).
Millward, S.W. et al. "Design of Cyclic Peptides That Bind Protein Surfaces with Antibody-Like Affinity", ACS Chemical Biology: vol. 2, No. 9, 625-634, (2007).
Mirkin CA. "Programming the assembly of two- and three-dimensionial architectures with DNA and nanoscale inorganic building blocks", Inorg Chem. May 29, 2000;39(11):2258-72.
Moore et al. "Site-Specific Modification of Pre-mRNA: The 2'-Hydroxyl Groups at the Splice Sites", Science, vol. 256, 992-997, 1992.
Mudrakovskaya, et al. "Solid-Phase Enzymatic Synthesis of Oligoribonucleotides", Biorg Khim vol. 17, No. 6, pp. 469-472 (1991).
Mutter, M. et al. "Functionalized polyethylene glycols and polypeptides in organic synthesis and catalysis", Reactive Polymers, vol. 6, pp. 99-107 (1987).
Myers, et al. "Detection of single base substitutions by ribonuclease cleavage at mismatches in RNA:DNA duplexes" Science 230:1242-6 (1985).
Nazarenko et al., "A closed tub format for amplification and detection of DNA based on energy transfer", Nucleic Acids Research, 1997, vol. 25, No. 12, p. 2516-2521.
Needels, CM, et al. "Generation and screening of an oligonucleotide-encoded synthetic peptide library", Proc. Natl. Acad. Sci., USA, vol. 90, pp. 10700-10704. (Nov. 1993).
Nemoto et al., "In vitro virus: bonding of mRNA bearing puromycin at the 3'terminal end to the C-terminal end of its encoded protein on the ribosome in vitro", FEBS Lett. Sep. 8, 1997; 414(2):405-8.
Nestler et al. "A General Method for Molecular Tagging of Encoded Combinatorial Chemistry Libraries", J. Org. Chem., 59, 4723-4724 (1994).
Ni et al., "Versatile Approach to Encoding Combinatorial Organic Syntheses Using Chemically Robust Secondary Amine Tags", J. Med. Chem. 1996, 39, 1601-1608.
Nicolaou et al., "Radiofrequency Encoded Combinatorial Chemistry", Angew. Chem. Int. Ed. Engl., 1995, 34, No. 20, pp. 2289-2291.
Nielsen "Combinatorial chemistry and automation", DDT, vol. 1, No. 11, pp. 458-460 (Nov. 1996).
Nielsen et al., "Synthetic methods for the implementation of encoded combinatorial chemistry". J. Am. Chem. Soc. 1993, 115, 9812-9813, with supplementary Materials (pp. 1-7).
Nielsen et al., "Towards Chemical Implementation of Encoded Combinatorial Libraries", Methods: A Companion to Meth in Enzymol., vol. 6, 361-371, 1994.
Nikolaiev et al. "Peptide-Encoding for structure determination of nonsequenceable polymers within libraries synthesized and tested on solid-phase supports", Peptide Research, vol. 6, No. 3, pp. 161-170 (1993).
Nishigaki et al. "Y-ligation: an efficient method for ligating single stranded DNAs and RNAs with T4 RNA ligase", Department of Functional Materials Science, Saitama University, Urawa, Japan. Molecular Diversity vol. 4(3), 187-190 (2000).
Noren et al., "A General Method for Site-Specific Incorporation of Unnatural Aminoacids into Proteins", Science, American Association for the advancement of science. Washington, DC, vol. 244, 1989, pp. 182-188.
"Nucleic Acid-Templated Synthesis as a Model System for Ancient Translation" Calderone, C.T. and Liu, D.R. Curr. Opin. Chem. Biol. 8, 645-653 (2004).
"The Nucleus", Jan. 2004, vol. LXXXII, No. 5. R. Grubina; "Summer Research Report: R. Grubina on DNA Templated Synthesis for Small Molecule Library", p. 10-14.
O'Donovan et al. "Blind analysis of denaturing high-performance liquid chromatography as a tool for mutation detection", Genomics. 52:4449 (1998).
Ohlmeyer et al., Complex synthetic chemical libraries indexed with molecular tags. Proc. Natl. Acad. Sci, USA, vol. 90, pp. 10922-10926, Dec. 1993, Chemistry.
"Organic Chemistry", Wikipedia, [accessed Dec. 10, 2009]: http://en.wikipedia.org/wiki/organic-chemistry (10 pages).
"Orthogonal Protectioni Protecting Group", Wikipedia: http://en.Wikipedia.org/wiki/protecting-group#Orthogonal-protection [accessed Apr. 15, 2010].
Otto, S. et al., "Recent developments in dynamic combinatorial chemistry". Current opinion in Chemical Biology 2002, 6:321-327.
Pavia, Mr. "The Chemical generation of molecular diversity". http//www.netsci.org/Science/Combichern/feature01.html.
Persichetti, et al. "Cross-Linked Enzyme Crystals (CLECs) of Thermolysin in the Synthesis of Peptides", Journal of the American Chemical Society, 117: 2732-2737 (1995).
Piccirilli, "RNA seeks its marker", Nature vol. 376, Aug. 17, 1995, p. 548-49.
Pochet, et al. "Solid-Supported Ligation Primer", Nucleic Acids Research, 16(4): 1619 (1988).
Polsky-Cynkin et al. "Use of DNA immobilized on platic and agarose supports to detect DNA by sandwich by hybridization", Clin. Chem. 31(9): 1438-43 (Sep. 1985).
Porco, Jr. "Synthesis Undressed", Nature 446, 383-5 (Mar. 22, 2007).
Purmal, et al. "A new affinity reagent for the site-specific, covalent attachment of DNA to active-site nucleophiles: application to the EcoRI and Rsrl restriction and modification enzymes", Nucleic Acids Research; vol. 20, No. 14; Oxford University Press; pp. 3713-3719 (1992).
Ramström, O. et al. "In situ generation and screening of a dynamic combinatorial carbohydrate library against concanavalin A". ChemBioChem, 2000, 1, 41-48.
Rembold et al., "Single-strand regions of Poly(G) act as templates for oligo(C) synthesis" J. Mol. Evol. 1994, 38, 2005.

(56) References Cited

OTHER PUBLICATIONS

Roberts, et al. "RNA-peptide fusions for the in vitro selection of peptides and proteins", Proc Natl Acad Sci USA, Nov. 11, 1997; 94 (23):12297-302.
Roberts, et al., "Simultaneous selection, amplification and isolation of a pseudo-peptide receptor by an immoblisied N-methyl ammonium ion template". Chem. Commun. 2002, 938-939.
Roberts, et al., "RNA-peptide fusions for the in vitro selection of peptides and protein". Proc Natl Acad Sci USA. Nov. 11, 1997; 94(23):12297-302.
Robertson, "Direct Evolution Process for Robust Enzyme Catalysis in Organic Solvents"; Report date: Sep. 1996. pp. 1-14.
Robinson "A Synthesis of Tropinone", Journal of the Chemical Society Transactions. vol. 111, pp. 762-768, (1917).
Rodriguez et al., "Template-directed extension of a guanosine 5'-phosphate covalently attached to an oligodeoxycytidylate template", J. Mol Evol (1991) 33:477-482.
Romaniuk, et al. "Joining of RNA molecules with RNA ligase", Methods in Enzymology, vol. 100, pp. 52-59 (1983).
Rosenbaum, DM et al., "Efficient and sequence-specific DNA-templated polymerization of peptide nucleic acid aldehydes". J. Am. Chem. Soc. vol. 125, No. 46, 2003, 13924-13925.
Roux, "Optimization and troubleshooting in PCR", PCR Methods Appl., vol. 4, No. 5, S185-S194, 1995.
Saiki et al. "Genetic analysis of amplified DNA with immobilized sequence-specific oligonucleotide probes" PNAS 86(16): 6230-6234 (1989).
Sales J et al. "Biosynthetic Polydeoxynucleotides as Direct Templates for Polypeptide Synthesis". J. of Biological Chemistry, vol. 243, No. 6, 1968, p. 1012-1015.
Sarmento, et al. "Cardosins A and B, Two New Enzymes Available for Peptide Synthesis", Journal of Molecular Catalysis B: Enzymatic, 5: 327-330 (1998).
Scheuermann et al. "DNA-encoded chemical libraries: A tool for drug discovery and for chemical biology", ChemBioChem 0000, 00, 1-8 (2010).
Scheuermann et al., "DNA-encoded chemical libraries", Journal of Biotechnology 126 568-581 (2006).
Schmidt et al. "Information transfer from peptide nucleic acids to RNA by template-directed syntheses". Nucleic Acids Res. Dec. 1, 1997;25(23):4792-4796.
Schmidt, et al., "Information transfer from peptide nucleic acids to RNA by template-directed syntheses", Nucleic Acids Res., vol. 25(23), pp. 4797-4802, Dec. 1, 1997.
Schmitz et al., "Solid-Phase Enzymatic Synthesis of Oigonucleotides", Org. Lett., 1(11): 1729-1731 (1999).
Schoenlber et al. "Photochemical release of amines by C,N-bond cleavage", Synlett 501-504 (2003).
Schultz et al. "The Combinatorial Library: A Multifunctional Resource", Biotechnol. Prog. 12, 729-743 (1996).
Schwartz, "Template-directed synthesis of novel, nucleic acid-like structures", Science 1985, 228,585-7.
Seelig et al., "Site-Specific Modification of Enzymatically Synthesized RNA: Transcription Initiation and Diels-Alder Reaction," Tetrahed. Lett., vol. 38, 7729-7732, 1997.
Seo et al., "Click Chemistry to Construct Fluorescent Oligonucleotides for DNA Sequencing", J. org. Chem., vol. 68, 609-612, 2003.
Shabarova, et al. "Chemical ligation of DNA: the first non-enzymatic assembly of a biologically active gene", Nucl. Acids Res., 19:4247-51 (1991).
Sharifian "Errors induced during PCR amplification", May 30, 2010.
Sherlin et al., "Chemical and Enzymatic Synthesis of tRNAs for High-throughput Crystallization", RNA, vol. 7, 1671-1678, 2001.
Shchepinov, et al. "Trityl tags for encoding in combinatorial synthesis", Tetraheddron 56 2713-2724 (2000).
Shuman "DNA ligases: Progress and Prospects"; jbc.org/content/284/26/17365. full downloaded Feb. 10, 2009.

Smith, et al., "DNA-guided assembly of proteins as a pathway to an assembler", http://www.wadsworth.org/albcon97/abstract/krummena.htm, The 1997 Albany Conference: Biomolecular Motors and Nanomachines.
Snyder "Ordered multistep synthesis in a single solution directed by DNA templates", Angew Chem Int Ed Engl 44, 7379 (2005).
Sokolova et al. "Chemical reactions within DNA duplexes; Cyanogen bromide as an effective oligodeoxyribonucleotide coupling agent"; FEBS letters, vol. 232, No. 1, pp. 153-155 (May 1988).
Starck et al., "The Puromycin Route to Assess Stereo- and Regiochemical Constraints on Peptide Bond Formation in Eukaryotic Ribosomes", J. Am. Chem. Soc., 2003, 125, 8090-8091.
Still, "Career-In-Review (CIR)", BJ Wright, Synthesis Literacy Group, Columbia University Chemistry, Mar. 30, 2007.
Storhoff et al. "Programmed Materials Synthesis with DNA". Chem Rev. Jul. 14, 1999:99(7):1849-1862.
Strachan et al., "Human Molecular Genetics", 2nd edition, textbook published by Wiley-Liss, 1999.
Studer et al., "Fluorous Synthesis: A Fluorous-Phase Strategy for Improving Separation Efficiency in Organic Synthesis", 1997, Science 275, pp. 822-826.
Summerer D., et al., "DNA-templated synthesis: more versatile than expected.", Angewandte Chemie, (Jan. 4, 2002), vol. 41, No. 1., pp. 89-90.
Tabor "DNA-ligases"; Current Protocols in Molecular Biology 3.14.1-3.14.4 (1987).
Tabuchi et al., "An Efficient Ligation Method in the Making of an in vitro Virus for in vitro Protein Evolution," Biol., Proced. Online, vol. 4, No. 1, 49-54, 2002.
Takemori et al. "Stabilization of Enzyme Activity by an Organic Solvent", Abstract only, Nature 215, 417-419 (Jul. 22, 1967).
Tamura et al."Oligonucleotide-directed peptide synthesis in a ribosome- and ribozyme-free system", Proc Natl Acad Sci USA. Feb. 13, 2001; 98(4):1393-7.
Tan et al. "Natural-product inhibitors of human DNA ligase I", Biochemical Journal 314: 993-1000 (1996).
Tan et al. "Ligand discovery using encoded combinatorial libraries", Current Opinion in Drug Discovery & Development, 3(4), p. 439-53 (Jul. 2000).
Tanaka, K. et al., "Synthesis of a novel nucleoside for alternative DNA base pairing through metal complexation", J. Org. Chem. 1999, 64, 5002-5003.
Terrett et al., "Combinatorial Synthesis—The Design of Compound Libraries and their Application to Drug Discovery", Tetrahedron, 1995, vol. 51, No. 30., pp. 8135-8173.
Tessier et al. "Ligation of Single-Stranded Oligodeoxyribonucleotides by T4 RNA Ligase", Analytical Biochemistry 158, 171-178 (1986).
"Translating DNA into synthetic Molecules", David R. Liu, PLoS Biology, Jul. 2004, vol. 2, Iss. 7, p. 905-6.
"Translation of DNA into Synthetic N-Acyloxazolidines" Li, X.; Gartner, Z.J.' Tse, B.N. Liu, D.R. J. Am. Chem. Soc. 126,5090-5092 (2004).
Tse "Translation of DNA into a library of 13,000 synthetic small-molecule macrocycles suitable for in vitro selection", J Am Chem Soc 130, 15611 (2008).
Uhlenbeck et al. "T4 RNA Ligase", The Enzymes, vol. XV, pp. 31-58 (1982).
Unknown "Science & Technology: Concentrates", Chem. & Eng. news 82 [40] 31 (2004).
Vágner, et al. "Enzyme-mediated spatial segregation on individual polymeric support beads: Application to generation and screening of encoded combinatorial libraries", Proc. Natl. Acad. Sci. USA, vol. 93, pp. 8194-8199, (Aug. 1996).
Vaisman et al. "Human DNA polymerase, promiscuous mismatch extension", JBC 276: 30615-30622 (2001).
Verma et al., "Modified Oligonucleotides: Synthesis and Strategy for Users", Annu. Rev. Biochem., vol. 67, 99-134, 1998.
Visscher et al."Template-directed oligomerization catalyzed by a polynucleotide analog". Science. Apr. 21, 1989; 244(4902):329-31.
Visscher, J. and Alan W. Scwartz. "Template-Directed Synthesis of Acyclic Oligonucleotide Analogues," J Mol Evol (1988) 28:3-6.

(56) References Cited

OTHER PUBLICATIONS

Visscher J. et al., Temple-directed synthesis of acyclic oligonucleotide analogues, Journal of Molecular Evolution. (1998), vol. 28, No. ½, pp. 3-6.
Visscher et al. "Oligomerization of deoxynucleoside-bisphosphate dimers; template and linkage specificity". Orig Life Evol Biosph. 1989; 19(1):3-6.
Vratskikh et al. "Solid-phase synthesis of oligoribonucleotides using T4 RNA ligase and T4 polynucleotide kinase", Biochimie 77, 227-232 (1995).
Wagner et al. "Mutation detection using immobilized mismatch binding protein (MutS)" Nucleic Acids Research 22, 3944-3948 (1995).
Walder et al. "Complementary carrier peptide synthesis: general strategy and implications for prebiotic origin of peptide synthesis", Proc Natl Acad Sci USA. Jan. 1979; 76(1):51-5.
Walder, Joseph A. et al. "Complementary carrier Peptide Synthesis: General Strategy and Implications for Prebiotic Origin of Peptide Synthesis," Department of Chemistry, and Department of Biochemistry and Molecular Biology, Northwestern University, Evanston, Illinois 60201.
Walder et al., "Complementary carrier peptide synthesis: general strategy and implications for prebiotic origin of peptide synthesis", Proc Natl Acad Sci USA, vol. 76(1), pp. 51-55, 1979.
Wang et al. "A new functional suppressor tRNA/aminoacyl-tRNA synthetase pair for the in vitro incorporation of unnatural amino acids into proteins" J. Am. Chem. Soc 2000, 122, 5010-5011 Pub. Apr. 5. 2000.
Wang et al. "Circular RNA oligonucleotides. Synthesis, nucleic acid binding properties, and a comparison with circular DNAs"; Nucleic Acids Research, 1994, vol. 22, No. 12; Oxford University Press; pp. 2326-2333 (1994).
Washington et al. "Mismatch extension ability of yeast and human DNA polymerase n", JBC 276: 2263-2266 (2001).
Waybright et al. "Oligonucleotide-directed assembly of materials: defined oligomers". J Am Chem Soc. Mar. 7, 2001;123(9):1828-33. Pub. on web Feb. 7, 2001.
Website: "Combinatorial chemistry", http://www.ukessays.co.uk/essays/chemistry/combinatorial-chemistry.php, Oct. 29, 2012, pp. 1-11.
http://en.wikipedia.orgiwiki/Scaffold-protein (2005).
Website of Dr. D. R. Liu, publicly available Mar. 11, 2000.
Website of Dr. D. R. Liu, publicly available Oct. 15, 2000.
Website of prof. David R. Liu, publicly available Feb. 15, 2001.
Website of Dr. D. R. Liu, publicly available Mar. 1, 2001.
Website of prof. David R. Liu, publicly available Mar. 31, 2001.
Website of Dr. D. R. Liu, publicly available Apr. 19, 2001.
Website of Dr. D. R. Liu, publicly available Sep. 23, 2001.
Website of prof. David R. Liu, publicly available Nov. 30, 2001.
Website of prof. David R. Liu, publicly available Jun. 4, 2002.
Website of prof. David R. Liu, publicly available Aug. 2, 2002.
Website of Dr. D. R. Liu, publicly available Sep. 24, 2002.
Website of prof. David R. Liu, publicly available Oct. 17, 2002.
Website of Dr. D. R. Liu, publicly available Nov. 20, 2002.
Website of prof. David R. Liu, publicly available Nov. 29, 2002.
Website of prof. David R. Liu, publicly available Feb. 8, 2003.
Website of prof. David R. Liu, publicly available Mar. 27, 2003.
Website of prof. David R. Liu, publicly available Apr. 23, 2003.
Website of prof. David R. Liu, publicly available Jun. 6, 2003.
Website of prof. David R. Liu, publiciy available Aug. 1, 2003.
Website of Dr. D. R. Liu, publicly available Oct. 15, 2003.
Website of prof. David R. Liu, publicly available Dec. 16, 2003.
Website of prof. David R. Liu, publicly available Feb. 10, 2004.
Weiss et al. "Enzymatic Breakage and Joining of Deoxyribonucleic Acid, I. Repair of Single-Strand Breaks in DNA By an Enzyme System From *Escherichia coli* Infected With T4 Bacteriophage" PNAS 57, (4): 1021-1028 (1967).
Weizman, H. et al., "2-2Bipyridine ligandoside: a novel building block for modifying DNA with intra-duplex metal complexes", J. Am. Chem. Soc. 2001, 123, 3375-3376.

Wermuth et al., "Glossary of Terms Used in Medical Chemistry", Pure & Appl. Chem, 1998, vol. 70, No. 5, pp. 1129-1143.
Whitesides et al. "Enzymes as Catalysts in Organic Synthesis", Aldrichimica Acta., vol. 16, No. 2, pp. 27-34, (1983).
Winzeler et al. "Fluorescence-based expressioin monitoring using microarrays", Methods Enzymol. 306: 3-18 (1999).
Woiwode et al., "Synthetic Compound Libraries Displayed on the Surliace of Encoded Bacteriophage", Chem. Biol., vol. 847-858. Sep. 2003.
Wojczewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series Book 12, Pergamon, Elsevier Science Lrd. (Oxford, England) 1994, pp. Xiii-xv, 1-40, and 329-334.
Wong et al. "Branch capture reactions: displacers dervied from assymmetric PCR"; 1991 Oxford University Press; Nucleic Acids Research; vol. 19; No. 9; pp. 2251-2259 (1991).
www.wikipedia.org/wiki/DNA-encoded chemical library Oct. 2, 2012, pp. 1-12.
http://www2.umt.edu/medchem/teaching/medchem/mclect14.htm, Thompson C. M., Medicinal Chemistry, lecture 14, Pharmaceutical Sciences 621 & Chemistry 569, (2005).
Xu et al. "A Novel 5'-Iodonucleoside Allows Efficient Non-enzymatic Ligation of Single-Stranded and Duplex DNA", Abstract, Glen Research Catalog, Tetrahedron Letters 38:5595-5598 (1997).
Xu et al. "High sequence fidelity in a non-enzymatic DNA autoligation reaction", Nucleic Acids Research, vol. 27, No. 3; pp. 875-881 (1999).
Xu et al. "Rapid and Selective selenium-mediated autoligation of DNA strands," J. Am. Chem. Soc. 2000, 122, 9040-1 Pub. on web. Aug. 31, 2000.
Xu et al "Nonenzymatic autoligation in direct three-color detection of RNA and DNA point mutations," Nat. Biotechnol. Feb. 2001; 19(2):148-52.
Xu et al, "Rapid and Selective selenium-mediated autoligation of DNA strangs," J. Am. Chem. Soc. vol. 112, pp. 9040-9041, 2000.
Ymane et al., "Discrimination between D- and L-Tyrosyl Transfer Ribonucleic Acids in Peptide Chain Elongationi", Biochemistry, vol. 20, No. 25, Dec. 8, 1981, pp. 7059-7064.
Zhan ZJ and Lynn, DG "Chemical Amplification through template-directed synthesis", J. Am. Chem. Soc. 1997, 119, 12420-1.
Zhang et al., Solution-Phase Preparation of a 560-Compound Library of Individual Pure Mappicine.
Analogons by Fluorous Mixture Synthesis , J. Am. Chem. Soc., vol. 124, 10443-10450, 2002.
Zhu et al. A Primer-dependcnt Polymerase Function of Pseudomonas aeruginosa ATP-dependent DNA ligase (LigD). Journal of Biological Chemistry 280(1): 418-427 (2005).
Zuckerman, RN et al., "Discovery of nanomolar ligands for 7-transmembrane G-protein-coupled receptors from a diverse N-(substituted) glycine peptoid library". J. Med. Chem. 1994, 37, 2678-2685.
Office Action in European application No. 07114663.3, dated Sep. 12, 2011.
Response to European Search Report in European application No. 10184311.8, dated Feb. 6, 2012.
Response to Office Action in European application No. 08169346.7, dated Feb. 10, 2012.
Office Action in European application No. 081699346.7, dated Feb. 24, 2012.
Annex to Office Action in European application No. 08169346.7, dated Feb. 24, 2012.
Response to Office Action in European application No. 09154197.9, dated Aug. 5, 2011.
Office Action in European application No. 09154197.9, dated Sep. 12, 2011.
Annex to Office Action in European application No. 09154197.9, dated Sep. 12, 2011.
European Search Report in European application No. 10183942.1, dated Feb. 6, 2012.

(56) References Cited

OTHER PUBLICATIONS

European Search Opinion in European application No. 10183942.1, dated Feb. 6, 2012.
Communication re partial European Search Report in European application No. 10184069.2, dated Feb. 10, 2012.
Partial European Search Report in European application No. 101840069.2, dated Feb. 3, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6 dated Oct. 7, 2011.
Response to Partial European Search Report in European application No. 10192717.6, dated Dec. 8, 2011.
European Search Report in European application No. 10192717.6, dated Jan. 25, 2012.
European Search Opinion in European application No. 10192717.6, dated Jan. 25, 2012.
International Search Report in PCT/DK2011/000031, dated Aug. 23, 2011.
Opposition against EP 1558744 filed by Strawman Limited on Mar. 12, 2012.
Opposition against EP 1558744 filed by HGF on Mar. 14, 2012.
Annex I: Vipergen Technology Paper—The YoctoRector drug discover technology platform. 2 pages.—No Date.
Australian Patents Act 1990—Section 32 Regulation 3.6, (Request for a Determination of Dispute between Applicants) and 3.7 Application to Commissioner for Declaration of an Eligible Person.—No Date.
Office Action in European patent application No. 10184311.8, dated Mar. 19, 2012, with Annex.
Office Action in Israel patent application No. 207672, dated Jan. 15, 2012, with English translation.
Response to OA in Israel patent avplication No. 207672, dated Jun. 14, 2012.
Office Action in Israel patent application No. 207673. dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application. No. 200380104764.5, dated Jul. 16, 2012.
Office Action in Japanese patent application No. P2010-226107, dated Jul. 10, 2012, with English translation.
Office Action in European patent application. No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
IPER International Preliminary Examination Report from PCT No. PCT/DK02/00419 dated Jan. 28, 2004.
Response to Office Action in EP 07114663.3 dated May 17, 2013.
3rd Office Action in European patent application No. 07114663.3 dated Jun. 3, 2013.
Response to 1st Office Action of Mar. 19, 2012 in EP 10184311.8 submitted Jan. 18, 2013.
2nd Office action dated Feb. 6, 2013 in EP 10184311.8.
Response to 2nd Office Action of Feb. 24, 2012 in EP 08169346.7 submitted Dec. 21, 2012.
3rd Office Action dated Jan. 29, 2013 in EP 08169346.7.
Response to 4th Office Action dated Jun. 9, 2011 in EP 03766117.0 submitted Mar. 14, 2012.
5th Office Action from European Appilication No. 03766117.0 dated May 31, 2012.
Office Action from European Application No. 03766117.0 dated Mar. 26, 2013.
Decision to Grant dated Oct. 10, 2013 re European patent application No. 09154197.9.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
Response to ESR re European Patent Application No. 10183942.1 submitted Jan. 9, 2013.
1st Office Action for European Patent Application No. 10183942.1 dated Feb. 11, 2013.
European Search Report dated Jun. 6, 2012 re EP 10184069.2.
Response dated Apr. 12, 2013 to European Search Report issued in European Patent Application No. 10184069.2.
Office Action for European Patent Application No. 10184069.2 dated Jul. 3, 2013.
Office Action in European patent application No. 10192716.8 dated Jul. 3, 2013.
Response to identify subject matter for search Response to ESR dated Jan. 25, 2012 submitted Dec. 5, 2012.
Invitation to identify subject matter for search Office Action dated Jul. 16, 2013 re European patent application No. 10192717.6.
European Office Action from EP 09765460.2 dated May 7, 2012.
Response to office action re 09765460.2 submitted Feb. 22, 2013.
Communication pursuant to Rule 161(1) and 162 for European Application No. 11720372.9 dated Dec. 12, 2012.
Notice of Acceptance for Australian Application No. 2003273792 dated Jun. 22, 2011.
Office action dated Aug. 20, 2012 re Canadian patent application No. 2,544,153.
Notice of Allowance dated Sep. 3, 2012 re Chinese patent application No. 200380104764.5.
Office Action in Israeli patent application No. 207672 dated May 28, 2013.
Office Action in Israeli patent application No. 207673 dated May 28, 2013.
Office Action dated Jan. 29, 2013 re Japanese patent application No. 2010-226107.
Decision of dismissal of amendment dated Aug. 20, 2013 re Japanese patent application No. 2010-226107.
Non-final Rejection dated Oct. 13, 2005 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Supplemental response submitted Jun. 2, 2010 re U.S. Appl. No. 12/330,709.
Ex parte Quyale Action dated Jul. 27, 2010 re U.S. Appl. No. 12/330,709.
Response of Jan. 10, 2011 to Ex parte Quayle Action re U.S. Appl. No. 12/330,709.
Office Action dated Sep. 17, 2012 re U.S. Appt. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Response submitted Sep. 16, 2011 to non-final rejection rejection re U.S. Appl. No. 10/523,006.
Final rejection dated Feb. 6, 2012 re U.S. Appl. No. 10/523,006.
RCE submitted Aug. 6, 2012 re U.S. Appl. No. 10/523,006.
Response submitted Oct. 11, 2013 re U.S. Appl. No. 10/523,006.
Response after Non-final rejection submitted Oct. 25, 2011 re U.S. Appl. No. 10/539,288.
Final rejection dated Dec. 22, 2011 re U.S. Appl. No. 10/539,288.
Notice of Appeal filed Jun. 18, 2012 re U.S. Appl. No. 10/539,288.
RCE filed Aug. 20, 2012 re U.S. Appl. No. 10/539,288.

(56) References Cited

OTHER PUBLICATIONS

Non final rejection dated Sep. 21, 2012 re U.S. Appl. No. 10/539,288.
Response after Non-final rejection submitted Feb. 28. 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Second amendment after Notice of Appeal submitted Sep. 28, 2009 re U.S. Appl. No. 10/545,795.
Advisory Action dated Oct. 21, 2009 re U.S. Appl. No. 10/545,795.
Interview summary dated Jul. 15, 2010 re U.S. Appl. No. 10/545,795.
Notice of Appeal filed Jul. 27, 2011 re U.S. Appl. No. 10/545,795.
Restriction requirement dated Apr. 24, 2012 re U.S. Appl. No. 13/179,283.
Response submitted Jul. 23, 2012 to restriction requirement re U.S. Appi. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Examiner's amendment communication dated May 12, 2011 re U.S. Appl. No. 10/525,817.
Notice of Allowance dated Oct. 14, 2011 re U.S. Appl. No. 10/525,817.
Notice of Allowance dated Jan. 19, 2012 re U.S. Appl. No. 10/525,817.
RCE dated Mar. 19, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
RCE dated Jul. 28, 2011 re U.S. Appl. No. 11/402,957.
Third Notice of Allowance dated Oct. 31, 2011 re U.S. Appl. No. 11/402,957.
RCe dated Dec. 12, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Response submitted Oct. 7, 2011 to Restriction Requirement re U.S. Appl. No. 10/589,551.
Non-final rejection dated Oct. 2011 re U.S. Appl. No. 10/589,551.
1st Restriction requirement of Oct. 5, 2011 re U.S. Appl. No. 12/095,778.
Response dated Mar. 5, 2012 to 1st Restriction Requirement re U.S. Appl. No. 12/095,778.
2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Non-final rejection dated Oct. 8, 2013 re U.S. Appl. No. 12/095,778.
Decision to Grant from European Application No. EP 02740409.4 dated Jul. 26, 2007.
European Office Action from European Application No. EP02740409.4 dated Sep. 1, 2005.
Reply to European Office AcEion from European Application No. EP 02740409.4 dated Jun. 16, 2006.
Intent to Grant from European Application No. EP 02740409.4 printed Oct. 13, 2006.
Extended European Search Report from European Application. No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 dated Apr. 6, 2005.
Response to Restriction Requirement from U.S. Appl. No. 10/175,539 dated May 6, 2005.
Office Action (Non-Final Rejection) from U.S. Appl. No. 10/175,539 dated May 13, 2005.
Response to Office Action (Non-Final Rejection) from U.S. Appl. No. 10/175,539 dated Apr. 13, 2006.
Office Action (Non-Final Rejection) from U.S. Appl. No. 10/175,539 dated May 14, 2007.
Response to Office Action (Non-Final Rejection) from U.S. Appl. No. 10/175,539 dated Sep. 13, 2007.
Office Action (Final Rejection) from U.S. Appl. No. 10/175,539 dated May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 dated Nov. 27, 2007.
Response to Ex Pate Quayle Action from U.S. Appl. No. 11/175,539 filed Feb. 27, 2008.
Notice of Allowance from U.S. Appl. No. 10/175,539 dated May 30, 2008.
Issue Notification U.S. Appl. No. 10/175,539 dated Jun. 1, 2010.
Office Action (Non-Final Rejection) from U.S. Appl. No. 12/330,709 dated Oct. 27, 2009.
Response to Office Action (Non-Final Rejection) from U.S. Appl. No. 12/330,709 filed Apr. 21, 2010.
Notice of Allowance from U.S. Appl. No. 12/330,709 dated Mar. 3, 2011.
Request for Continued Examination and supplemental IDS from U.S. Appl. No. 12/330,709 filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 10, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 dated Apr. 13, 2010.
1st Office Action from European Application No. 08169346.7 dated Apr. 19, 2011.
Response filed in European Application No. 08169346.7 dated Mar. 23, 2011.
International Search Report for PCT Application No. PCT/DK03/00172 dated Nov. 3, 2003.
Office Action (Non-Final) for U.S. Appl. No. 10/507,121 dated Feb. 8, 2007.
Response to Office Action for U.S. Appi. No. 10/507,121 dated Jun. 7, 2007.
Office Action (Final Rejection) for U.S. Appl. No. 10/507,121 dated Sep. 7, 2007.

(56) References Cited

OTHER PUBLICATIONS

Request for Continued Examination and supplemental amendment for U.S. Appl. No. 10/507,121 filed Feb. 13, 2008.
Notice of Allowance for U.S. Appl. No. 10/507,121 dated Mar. 20, 2008.
Issue Notification for U.S. Appl. No. 10/507,121 dated Jul. 30, 2008.
Office Action (Non-Final) from U.S. Appl. No. 12/179,323 dated Jan. 27, 2010.
Response to Office Action from U.S. Appl. No. 12/179,323 filed Jun. 24, 2010.
Office Action (Final Rejection) for U.S. Appl. No. 12/179,323 dated Sep. 15, 2010.
Notice of Appeal from U.S. Appl. No. 12/179,323 filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 dated Feb. 18, 2004.
1st Restriction Requirement from U.S. Appl. No. 10/523,006 dated Apr. 4, 2008.
Response to 1st Restriction Requirement from U.S. Appl. No. 10/523,006, filed Oct. 1, 2008.
2nd Restriction Requirement from U.S. Appl. No. 10/523,006 dated Dec. 9, 2009.
Response to 2nd Restriction Requirement from U.S. Appl. No. 10/523,006 filed May 5, 2010.
3rd Restriction Requirement from U.S. Appl. No. 10/523,006 dated Aug. 3, 2010.
Response to 3rd Restriction Requirement from U.S. Appl. No. 10/523,006, filed Feb. 1, 2011.
Office Action (Non-Final) from U.S. Appl. No. 10/523,006 dated Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 dated Jun. 22, 2004.
Restriction Requirement for U.S. Appl. No. 10/539,288 dated Aug. 2, 2010.
Response to Restriction Requirement for U.S. Appl. No. 10/539,288 filed Jan. 31, 2011.
Office Action (Non-Final) for U.S. Appl. No. 10/539,288 dated Apr. 25, 2011.
1st Office Action for European Application No. 03729909.6 dated May 17, 2006.
Reply to 1st Office Action for European Application No. 03729909.6 dated Mar. 9, 2007.
2nd Office Action for European Application No. 03729909.6 dated Sep. 22, 2009.
Reply to 2nd Office Action for European Application No. 03729909.6 dated May 6, 2010.
International Search Report for PCT Application No. PCT/DK03/00417 dated Feb. 10, 2004.
Restriction Requirement for U.S. Appl. No. 10/518,056 dated Jan. 4, 2008.
Response to Restriction Requirement for U.S. Appl. No. 10/518,056 filed Jun. 2, 2008.
Office Action (Non-Final) for U.S. Appl. No. 10/518,056 dated Oct. 8, 2008.
Reply to Office Action for U.S. Appl. No. 10/518,056 filed Feb. 17, 2009.
Office Action (Final Rejection) for U.S. Appl. No. 10/518,056 dated May 27, 2009.
Notice of Appeal for U.S. Appl. No. 10/518,056 dated Oct. 27, 2009.
Amendment After Appeal for U.S. Appl. No. 10/518,056 filed Nov. 17, 2009.
Advisory Action for U.S. Appl. No. 10/518,056 dated Jan. 7, 2010.
Request for Continued Examination and IDS for U.S. Appl. No. 10/518,056 filed Mar. 22, 2010.
1st Office Action for European Application No. 04713515.7 dated Oct. 19, 2006.
Reply to 1st Office Action for European Application No. 04713515.7 dated Aug. 20, 2007.
2nd Office Action for European Application No. 04713515.7 dated Mar. 31, 2008.
Reply to 2nd Office Action for European Application No. 04713515.7 dated Dec. 5, 2008.
3rd Office Action for European Application No. 04713515.7 dated Sep. 6, 2010.
Reply to 3rd Office Action for European Application No. 04713515.7 dated Jun. 21, 2011.
International Search Report for PCT Application No. PCT/DK2004/000116 dated Aug. 23, 2004.
Office Action (Non-Final) for U.S. Appl. No. 10/545,795 dated Mar. 31, 2008.
Response filed for U.S. Appl. No. 10/545,795 filed Sep. 30, 2008.
Office Action for U.S. Appl. No. 10/545,795 dated Jan. 27, 2009.
Notice of Appeal filed for U.S. Appl. No. 10/545,795 filed Jul. 27, 2009.
Amendment after Appeal for U.S. Appl. No. 10/545,795 filed Sep. 28, 2009.
Office Action (Advisory Action) for U.S. Appl. No. 10/545,795 dated Sep. 29, 2009.
Request for Continued Examination and IDS for U.S. Appl. No. 10/545,795 filed Oct. 27, 2009.
Office Action (Non-Final) for U.S. Appl. No. 10/545,795 dated Nov. 16, 2009.
Office Action (Non-Final) for U.S. Appl. No. 10/545,795 dated Mar. 30, 2010.
Office Action (Interview Summary) for U.S. Appl. No. 10/545,795 dated Jul. 30, 2010.
Response filed for U.S. Appl. No. 10/545,795filed Aug. 30, 2010.
Office Action (Final rejection) for U.S. Appl. No. 10/545,795 dated Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.

(56) References Cited

OTHER PUBLICATIONS

International Search Report for International Application No. PCT/DK2004/000117 dated Aug. 19, 2004.
Restriction Requirement for U.S. Appl. No. 10/546,538 dated Jul. 31, 2008.
Response to Restriction Requirement for U.S. Appl. No. 10/546,538 filed Dec. 24, 2008.
Office Action (Non-Final) for U.S. Appl. No. 10/546,538 dated Jun. 10, 2009.
Response to Office Action for U.S. Appl. No. 10/546,538 filed Dec. 9, 2009.
Office Action (Final Rejection) for U.S. Appl. No. 10/546,538 dated Jun. 8, 2010.
Response to Office Action (Notice of Appeal) for U.S. Appl. No. 10/546,538 filed Dec. 8, 2010.
Office Action (Communication re: Appeal) for U.S. Appl. No. 10/546,538 dated Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 dated Sep. 15, 2010.
International Search Report for International Application No. PCT/DK2004/000195 dated Dec. 27, 2004.
Restriction Requirement for U.S. Appl. No. 10/549,619 dated Apr. 21, 2008.
Response to Restriction Requirement for U.S. Appl. No. 10/549,619 filed Sep. 22, 2008.
Office Action (Non-Final) for U.S. Appl. No. 10/549,619 dated Apr. 28, 2009.
Response to Office Action for U.S. Appl. No. 10/549,619 filed Oct. 26, 2009.
Office Action (Interview Summary) for U.S. Appl. No. 10/549,619 dated Mar. 3, 2010.
Amendment filed for U.S. Appl. No. 10/549,619 filed Oct. 21, 2010.
Notice of Allowance for U.S. Appl. No. 10/549,619, dated Jul. 7, 2010.
Amendment After Allowance for U.S. Appl. No. 10/549,619 filed Oct. 6, 2010.
Issue Notification for U.S. Appl. No. 10/549,619 mailed Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after ESP for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
International Search Repori for International Application No. PCT/DK03/00739 dated Aug. 30, 2004.
Restriction Requirement for U.S. Appl. No. 10/525,817 dated May 9, 2007.
Response to Restriction Requirement for U.S. Appl. No. 10/525,817, filed Sep. 10, 2007.
Restriction Requirement for U.S. Appl. No. 10/525,817 dated Nov. 28, 2007.
Response to Restriction Requirement for U.S. Appl. No. 10/525,817 filed Feb. 28, 2008.
Restriction Requirement for U.S. Appl. No. 10/525,817 dated Jul. 7, 2009.
Response to Restriction Requirement for U.S. Appl. No. 10/525,817 filed Oct. 5, 2009.
Office Action (Non-Final) for U.S. Appl. No. 10/525,817 dated Apr. 1, 2010.
Supplemental Office Action for U.S. Appl. No. 10/525,817 dated Apr. 5, 2010.
Response filed for U.S. Appl. No. 10/525,817 filed Jul. 27, 2010.
Office Action (Non-Final) for U.S. Appl. No. 10/525,817 dated Jan. 5, 2011.
Office Action (Interview Summary) for U.S. Appl. No. 10/525,817 dated Jul. 1, 2011.
Response filed for U.S. Appl. No. 10/525,817 filed Jul. 5, 2011.
Resiriction Requirement for U.S. Appl. No. 11/402,957 dated Jun. 25, 2008.
Response to Resiriction Requirement for U.S. Appl. No. 11/402,957 filed Aug. 25, 2008.
Office Action (Non-Final) for U.S. Appl. No. 11/402,957 dated Nov. 28, 2008.
Response, filed for U.S. Appl. No. 11/402,957 filed May 15, 2009.
Office Action (Non-Final) for U.S. Appl. No. 11/402,957 dated Jul. 6, 2009.
Response filed for U.S. Appl. No. 11/402,957 filed Dec. 7, 2009.
Office Action (Final Rejection) for U.S. Appl. No. 11/402,957 dated Feb. 16, 2010.
Response filed for U.S. Appl. No. 11/402,957 filed Jul. 28, 2010.
Notice of Appeal filed for U.S. Appl. No. 11/402,957 filed Aug. 16, 2010.
Notice of Allowance for U.S. Appl. No. 11/402,957 dated Sep. 2, 2010.
Request for Continued Examination filed for U.S. Appl. No. 11/402,957 filed Dec. 2, 2010.
Second Notice of Allowance for U.S. Appl. No. 11/402,957 dated Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.

(56) References Cited

OTHER PUBLICATIONS

Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 dated Feb. 14, 2005.
Restriction Requirement for U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644 filed Jan. 19, 2011.
Office Action (Non-Final) for U.S. Appl. No. 10/572,644 dated Oct. 29, 2009.
Response to Office Action for U.S. Appl. No. 10/572,644 filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000199 dated Jan. 23, 2006.
Office Action for U.S. Appl. No. 10/593,868 dated Mar. 30, 2009.
Response to Office Action for U.S. Appl. No. 10/593,868 filed Jul. 28, 2009.
Notice of Allowance for U.S. Appl. No. 10/593,868 dated Nov. 16, 2009.
Amendment after Allowance for U.S. Appl. No. 10/593,868 filed Feb. 16, 2010.
Issue Notification for U.S. Appl. No. 10/593,868 dated Apr. 7, 2010.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2ncl Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for Internationial Application No. PCT/DK2005/000106 dated Sep. 12, 2005.
Restriction Requirement for U.S. Appl. No. 10/589,551 dated Apr. 7, 2011.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 dated May 24, 2011.
Invitation to Identify Subject Matter for European Application No. 10 192 717.6 dated Jun. 1, 2011.
International Search Report for International Application No. PCT/DK2006/000685 dated Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
International Search Report for International Application No. PCT/DK2009/050129 dated Aug. 21, 2009.
Annex I: Vipergen Technology Paper—The YoctoReactor drug discovery technology platform. 2 pages, (Aug. 2008).
Annex II: Vipergen Technology Paper—The YoctoReactor drug discovery technology platform. 2 pages. Aug. 2008.
D. Halpin et al., "DNA Display I. Sequence-Encoded Routing of DNA Populations", Plos Biology, 2(7): 1016-1021 (2004).
D. Halpin et al., "DNA Display II. Genetic Manipulation of Combinatorial Chemistry Libraries for Small-Molecule Evolution", Plos Biology, 2(7): 1022-1030 (2004).
D. Halpin et al., "DNA Display III. Solid-Phase Organic Synthesis on Unprotected DNA", Plos Biology, 2(7): 1031-1038 (2004).

\* cited by examiner

Figure 13
A.
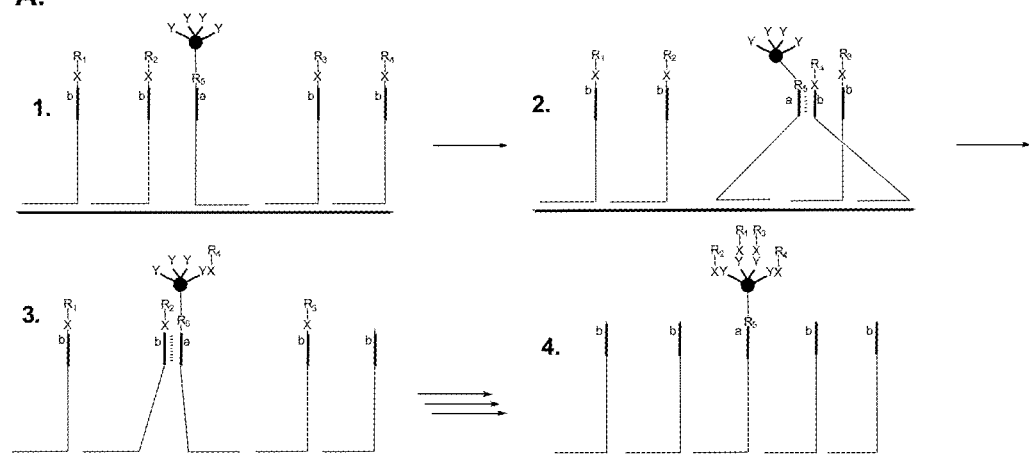
B.
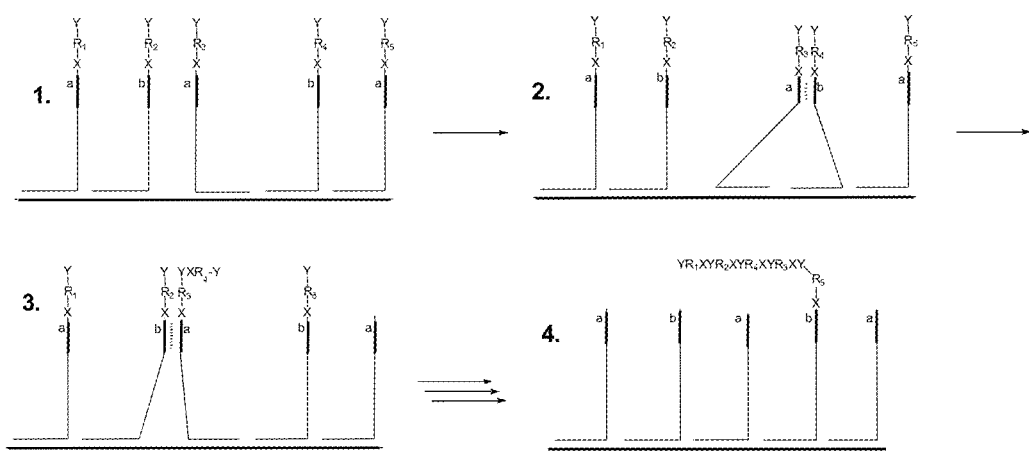

Figure 14 The Zipper box principle.

Fig. 16

Setup A:

| Pos. 3 | Pos. 2 | Pos. 1 | Pos. 0 |
|---|---|---|---|
| AH 36 | AH 258 | AH 276 | AH 51 |
| AH 142 | AH 272 | AH 277 | AH 82 |
| AH 201 | AH 273 |  | AH 133 |
| AH 202 | AH 274 |  | AH 134 |
| AH 203 |  |  | AH 135 |
| AH 240 |  |  | AH 236 |
| AH 255 |  |  | AH 270 |
| AH 261 |  |  | AH 271 |
| AH 262 |  |  |  |
| AH 275 |  |  |  |

AH 140
AH 278

Setup B:

| Pos. 3 | Pos. 2 | Pos. 1 | Pos. 0 |
|---|---|---|---|
| AH 36 | AH 258 | AH 276 | AH 156 |
| AH 142 | AH 272 | AH 277 | AH 251 |
| AH 201 | AH 273 |  | AH 252 |
| AH 202 | AH 274 |  |  |
| AH 203 |  |  |  |
| AH 240 |  |  |  |
| AH 255 |  |  |  |
| AH 261 |  |  |  |
| AH 262 |  |  |  |
| AH 275 |  |  |  |

AH 154
AH 256

AH 249
AH 260

AH 250
AH 263
AH 279

Lane 1: 20,1°C
Lane 2: 25,1°C
Lane 3: 30,6°C
Lane 4: 33,4°C
Lane 5: 38,2°C
Lane 6: 40,9°C
Lane 7: 24,9°C
Lane 8: 27,9°C
Lane 9: 32,8°C
Lane 10: 38,4°C
Lane 11: 43,2°C
Lane 12: 45,9°C Lane 1: 24,9°C
Lane 2: 27,9°C
Lane 3: 32,8°C
Lane 4: 38,4°C
Lane 5: 43,2°C
Lane 6: 45,9°C 1: 9,9°C
2: 15°C
3: 17,6°C
4: 23,3°C
5: 28,3°C
6: 31,7°C
7: 33°C
8: 35,3°C
9: 40,7°C
10: 43,4°C
11: 46,0°C
12: 50,8°C Experiment C and D Experiment A and B Fig. 24
1: 9,9°C
2: 15°C
3: 17,6°C
4: 23,3°C
5: 28,3°C
6: 31,7°C
7: 33°C
8: 35,3°C
9: 40,7°C
10: 43,4°C
11: 46,0°C
12: 50,8°C
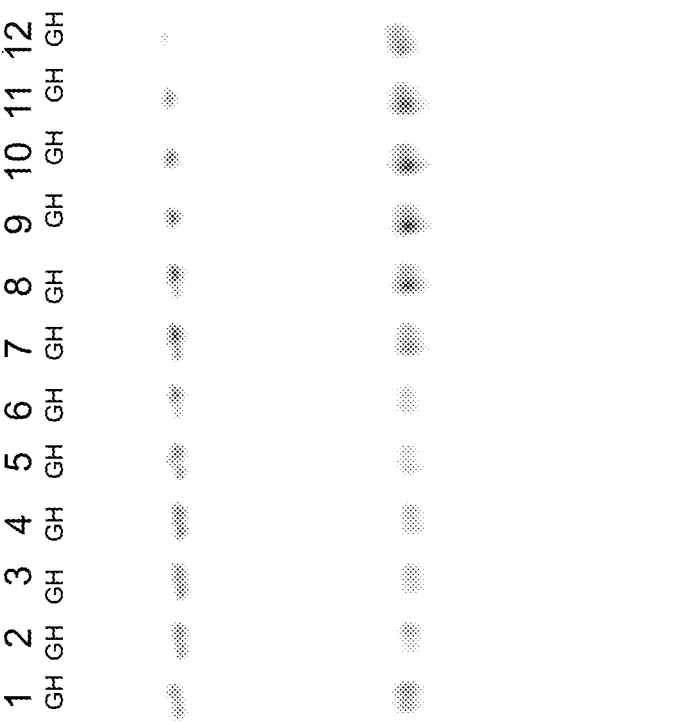
Experiment G and H
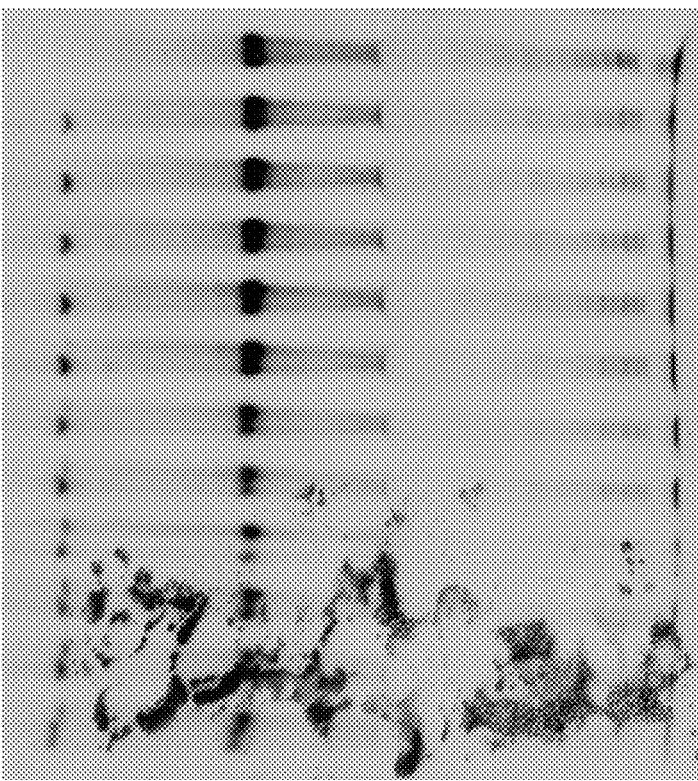
Experiment E and F

SEQUENCE LISTING

<160> NUMBER OF SEQ ID NOS: 63

<210> SEQ ID NO 1
<211> LENGTH: 15
<212> TYPE: DNA
<213> ORGANISM: artificial sequence
<220> FEATURE:
<223> OTHER INFORMATION: Synthetic Building block Ah 1
<220> FEATURE:
<221> NAME/KEY: modified_base
<222> LOCATION: (15)..(15)
<223> OTHER INFORMATION: modified thymine, Carboxy -dT; obtained by
    modification using carboxy modifier C2 dT (obtained from Glen
    Research, catalogue number 10-1035-90)

<400> SEQUENCE: 1
gctactcgta cgagn                                                  15

<210> SEQ ID NO 2
<211> LENGTH: 15
<212> TYPE: DNA
<213> ORGANISM: artificial sequence
<220> FEATURE:
<223> OTHER INFORMATION: Synthetic building block Ah 3

```
<220> FEATURE:
<221> NAME/KEY: modified_base
<222> LOCATION: (15)..(15)
<223> OTHER INFORMATION: modified thymine, base derived from Amino-
      modifier C2 dT (obtained from Glen Research catalogue # 10-1037-
      90)

<400> SEQUENCE: 2
gctactcgta cgagn                                                      15

<210> SEQ ID NO 3
<211> LENGTH: 15
<212> TYPE: DNA
<213> ORGANISM: artificial sequence
<220> FEATURE:
<223> OTHER INFORMATION: Synthetic Building block Ah 5
<220> FEATURE:
<221> NAME/KEY: modified_base
<222> LOCATION: (15)..(15)
<223> OTHER INFORMATION: modified thymine, base derived from Amino
      modifier C6 dT (obtained from Glen Research, catalogue # 10-1039-
      90)

<400> SEQUENCE: 3
gctactcgta cgagn                                                      15

<210> SEQ ID NO 4
<211> LENGTH: 15
<212> TYPE: DNA
<213> ORGANISM: Artificial sequence
<220> FEATURE:
<223> OTHER INFORMATION: Synthetic Building block Ah 2
<220> FEATURE:
<221> NAME/KEY: modified_base
<222> LOCATION: (1)..(1)
<223> OTHER INFORMATION: modified thymine, Carboxy -dT; obtained by
      modification using carboxy modifier C2 dT (obtained from Glen
      Research, catalogue number 10-1035-90)

<400> SEQUENCE: 4
ncacttgcag acagc                                                      15

<210> SEQ ID NO 5
<211> LENGTH: 15
<212> TYPE: DNA
<213> ORGANISM: Artificial sequence
<220> FEATURE:
<223> OTHER INFORMATION: Synthetic Building block Ah 4
<220> FEATURE:
<221> NAME/KEY: modified_base
<222> LOCATION: (1)..(1)
<223> OTHER INFORMATION: modified thymine, base derived from Amino-
      modifier C2 dT (obtained from Glen Research catalogue # 10-1037-
      90)

<400> SEQUENCE: 5
ncacttgcag acagc                                                      15

<210> SEQ ID NO 6
<211> LENGTH: 15
<212> TYPE: DNA
<213> ORGANISM: Artificial sequence
<220> FEATURE:
<223> OTHER INFORMATION: Synthetic Building block Ah 6
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)
```

<400> SEQUENCE: 6
ncacttgcag acagc                                                      15

<210> SEQ ID NO 7
<211> LENGTH: 14
<212> TYPE: DNA
<213> ORGANISM: Artificial sequence
<220> FEATURE:
<223> OTHER INFORMATION: Synthetic Building block Ah 14

<400> SEQUENCE: 7
gctactcgta cgag                                                       14

<210> SEQ ID NO 8
<211> LENGTH: 15
<212> TYPE: DNA
<213> ORGANISM: Artificial sequence
<220> FEATURE:
<223> OTHER INFORMATION: Synthetic Building block Ah 23
<220> FEATURE:
<221> NAME/KEY: modified_base
<222> LOCATION: (15)..(15)
<223> OTHER INFORMATION: modified thymine, Carboxy -dT; obtained by
      modification using carboxy modifier C2 dT (obtained from Glen
      Research, catalogue number 10-1035-90)

<400> SEQUENCE: 8
gctactggca tcggn                                                      15

<210> SEQ ID NO 9
<211> LENGTH: 15
<212> TYPE: DNA
<213> ORGANISM: Artificial sequence
<220> FEATURE:
<223> OTHER INFORMATION: Synthetic Building block Ah 24
<220> FEATURE:
<221> NAME/KEY: misc_feature
<222> LOCATION: (15)..(15)
<223> OTHER INFORMATION: modified thymine, base derived from Amino-
      modifier C2 dT (obtained from Glen Research catalogue # 10-1037-
      90)

<400> SEQUENCE: 9
gctactggca tcggn                                                      15

<210> SEQ ID NO 10
<211> LENGTH: 15
<212> TYPE: DNA
<213> ORGANISM: Artificial sequence
<220> FEATURE:
<223> OTHER INFORMATION: Synthetic Building block Ah 27
<220> FEATURE:
<221> NAME/KEY: modified_base
<222> LOCATION: (1)..(1)
<223> OTHER INFORMATION: modified thymine, base derived from Amino-
      modifier C2 dT (obtained from Glen Research catalogue # 10-1037-
      90)

<400> SEQUENCE: 10
ncacttgcag acagc                                                      15

<210> SEQ ID NO 11
<211> LENGTH: 56
<212> TYPE: DNA
<213> ORGANISM: Artificial sequence
<220> FEATURE:
<223> OTHER INFORMATION: Synthetic Building block Ah 36
<220> FEATURE:
<221> NAME/KEY: modified_base

```
<222> LOCATION: (56)..(56)
<223> OTHER INFORMATION: modified thymine, Carboxy -dT; obtained by
      modification using carboxy modifier C2 dT (obtained from Glen
      Research, catalogue number 10-1035-90)

<400> SEQUENCE: 11
cgacctctgg attgcatcgg tcatggctga ctgtccgtcg aatgtgtcca gttacn        56

<210> SEQ ID NO 12
<211> LENGTH: 56
<212> TYPE: DNA
<213> ORGANISM: Artificial sequence
<220> FEATURE:
<223> OTHER INFORMATION: Synthetic Building block Ah 37
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 12
ngtaactgga ctgtaagctg cctgtcagtc ggtactgacc tgtcgagcat ccagct        56

<210> SEQ ID NO 13
<211> LENGTH: 56
<212> TYPE: DNA
<213> ORGANISM: Artificial sequence
<220> FEATURE:
<223> OTHER INFORMATION: Synthetic Building block Ah 51
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 13
ngtaacacct gtgtaagctg cctgtcagtc ggtactgacc tgtcgagcat ccagct        56

<210> SEQ ID NO 14
<211> LENGTH: 56
<212> TYPE: DNA
<213> ORGANISM: Artificial sequence
<220> FEATURE:
<223> OTHER INFORMATION: Synthetic Building block Ah 67
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 14
ncattgacct gtgtaagctg cctgtcagtc ggtactgacc tgtcgagcat ccagct        56

<210> SEQ ID NO 15
<211> LENGTH: 56
<212> TYPE: DNA
<213> ORGANISM: Artificial sequence
<220> FEATURE:
<223> OTHER INFORMATION: Synthetic Building block Ah 69
<220> FEATURE:
<221> NAME/KEY: modified_base
<222> LOCATION: (3)..(3)
<223> OTHER INFORMATION: modified thymine, base derived from Amino
      modifier C6 dT (obtained from Glen Research, catalogue # 10-1039-
      90)

<400> SEQUENCE: 15
```
agnaacacct gtgtaagctg cctgtcagtc ggtactgacc tgtcgagcat ccagct        56

<210> SEQ ID NO 16
<211> LENGTH: 58
<212> TYPE: DNA
<213> ORGANISM: Artificial sequence
<220> FEATURE:
<223> OTHER INFORMATION: Synthetic Building block Ah 66
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 16
nttgtaactg gactgtaagc tgcctgtcag tcggtactga cctgtcgagc atccagct        58

<210> SEQ ID NO 17
<211> LENGTH: 58
<212> TYPE: DNA
<213> ORGANISM: Artificial sequence
<220> FEATURE:
<223> OTHER INFORMATION: Synthetic Building block Ah 65
<220> FEATURE:
<221> NAME/KEY: modified_base
<222> LOCATION: (58)..(58)
<223> OTHER INFORMATION: modified thymine, base derived from Amino-
      modifier C2 dT (obtained from Glen Research catalogue # 10-1037-
      90)

<400> SEQUENCE: 17
cgacctctgg attgcatcgg tcatggctga ctgtccgtcg aatgtgtcca gttacttn        58

<210> SEQ ID NO 18
<211> LENGTH: 30
<212> TYPE: DNA
<213> ORGANISM: Artificial sequence
<220> FEATURE:
<223> OTHER INFORMATION: Synthetic template Ah 28

<400> SEQUENCE: 18
gctgtctgca agtgaaccga tgccagtagc                                       30

<210> SEQ ID NO 19
<211> LENGTH: 40
<212> TYPE: DNA
<213> ORGANISM: Artificial sequence
<220> FEATURE:
<223> OTHER INFORMATION: Synthetic template Ah 38

<400> SEQUENCE: 19
agctggatgc tcgacaggtc ccgatgcaat ccagaggtcg                            40

<210> SEQ ID NO 20
<211> LENGTH: 50
<212> TYPE: DNA
<213> ORGANISM: Artificial sequence
<220> FEATURE:
<223> OTHER INFORMATION: Synthetic template Ah 7
<220> FEATURE:
<221> NAME/KEY: modified_base
<222> LOCATION: (50)..(50)
<223> OTHER INFORMATION: Biotinylated guanine, Guanine modified with
      Biotin phosphoramidite (obtained from Glen Research, Catalogue
      # 10-1953-95)

<400> SEQUENCE: 20
gctgtctgca agtgaactcg tacgagtagc gacagtcgac atcggtcacn                 50

```
<210> SEQ ID NO 21
<211> LENGTH: 51
<212> TYPE: DNA
<213> ORGANISM: Artificial sequence
<220> FEATURE:
<223> OTHER INFORMATION: Synthetic template Ah 8
<220> FEATURE:
<221> NAME/KEY: modified_base
<222> LOCATION: (51)..(51)
<223> OTHER INFORMATION: Biotinylated guanine, Guanine modified with
      Biotin phosphoramidite (obtained from Glen Research, Catalogue
      # 10-1953-95)

<400> SEQUENCE: 21
gctgtctgca agtgacactc gtacgagtag cgacagtcga catcggtcac n          51

<210> SEQ ID NO 22
<211> LENGTH: 52
<212> TYPE: DNA
<213> ORGANISM: Artificial sequence
<220> FEATURE:
<223> OTHER INFORMATION: Synthetic template Ah 9
<220> FEATURE:
<221> NAME/KEY: modified_base
<222> LOCATION: (52)..(52)
<223> OTHER INFORMATION: Biotinylated guanine, Guanine modified with
      Biotin phosphoramidite (obtained from Glen Research, Catalogue
      # 10-1953-95)

<400> SEQUENCE: 22
gctgtctgca agtgacgact cgtacgagta gcgacagtcg acatcggtca cn         52

<210> SEQ ID NO 23
<211> LENGTH: 80
<212> TYPE: DNA
<213> ORGANISM: Artificial sequence
<220> FEATURE:
<223> OTHER INFORMATION: Synthetic template Ah 11
<220> FEATURE:
<221> NAME/KEY: modified_base
<222> LOCATION: (80)..(80)
<223> OTHER INFORMATION: Biotinylated guanine, Guanine modified with
      Biotin phosphoramidite (obtained from Glen Research, Catalogue
      # 10-1953-95)

<400> SEQUENCE: 23
gctgtctgca agtgacgact gatccagtga catgcgtacc atcgaactcg tacgagtagc     60
gacagtcgac atcggtcacn                                                 80

<210> SEQ ID NO 24
<211> LENGTH: 46
<212> TYPE: DNA
<213> ORGANISM: Artificial sequence
<220> FEATURE:
<223> OTHER INFORMATION: Synthetic template containing a modified
      nucleobase having a carboxylic acid moiety, used in example 12,
      trisamine scaffold building block
<220> FEATURE:
<221> NAME/KEY: modified_base
<222> LOCATION: (46)..(46)
<223> OTHER INFORMATION: modified thymine, Carboxy -dT; obtained by
      modification using carboxy modifier C2 dT (obtained from Glen
      Research, catalogue number 10-1035-90)

<400> SEQUENCE: 24
gacctgtcga gcatccagct tcatgggaat tcctcgtcca caatgn               46

<210> SEQ ID NO 25
```

-continued

```
<211> LENGTH: 16
<212> TYPE: DNA
<213> ORGANISM: Artificial sequence
<220> FEATURE:
<223> OTHER INFORMATION: Synthetic template containing a 5'-Thiol
      modified cytosine nucleobase having a S-triphenylmethyl protected
      thio moiety, used in example 13
<220> FEATURE:
<221> NAME/KEY: modified_base
<222> LOCATION: (1)..(1)
<223> OTHER INFORMATION: modified cytosine, cytosine modified using
      5'-Thiol modifier C6 (obtained from Glen Research, catalogue # 10-
      1926-95)
<220> FEATURE:
<221> NAME/KEY: modified_base
<222> LOCATION: (16)..(16)
<223> OTHER INFORMATION: cytosine modified by connection through biotin
      phosphoramidite (Glen Research 10-1953-95) to base 1 of SEQ ID
      NO:62

<400> SEQUENCE: 25
nattgacctg tctgcn                                                        16

<210> SEQ ID NO 26
<211> LENGTH: 17
<212> TYPE: DNA
<213> ORGANISM: Artificial sequence
<220> FEATURE:
<223> OTHER INFORMATION: Synthetic template containing a 5'-Thiol
      modified cytosine nucleobase having a S-triphenylmethyl protected
      thio moiety, used in example 13
<220> FEATURE:
<221> NAME/KEY: modified_base
<222> LOCATION: (1)..(1)
<223> OTHER INFORMATION: modified cytosine, cytosine modified using
      5'-Thiol modifier C6 (obtained from Glen Research, catalogue # 10-
      1926-95)
<220> FEATURE:
<221> NAME/KEY: modified_base
<222> LOCATION: (17)..(17)
<223> OTHER INFORMATION: guanine modified by connection through biotin
      phosphoramidite (Glen Research 10-1953-95) to base 1 of SEQ ID
      NO:63

<400> SEQUENCE: 26
nattgacctg aaccatn                                                       17

<210> SEQ ID NO 27
<211> LENGTH: 80
<212> TYPE: DNA
<213> ORGANISM: Artificial sequence
<220> FEATURE:
<223> OTHER INFORMATION: Synthetic template used in example 14
<220> FEATURE:
<221> NAME/KEY: modified_base
<222> LOCATION: (1)..(1)
<223> OTHER INFORMATION: Biotinylated thymine, thymine modified with
      Biotin phosphoramidite (obtained from Glen Research, Catalogue
      # 10-1953-95)

<400> SEQUENCE: 27
ncttgcctga acgtagtcgt aggtcgatcc gcgttaccag agctggatgc tcgacaggtc         60
ccgatgcaat ccagaggtcg                                                    80

<210> SEQ ID NO 28
<211> LENGTH: 31
<212> TYPE: DNA
<213> ORGANISM: Artificial sequence
<220> FEATURE:
<223> OTHER INFORMATION: Synthetic oligo Ah 82
<220> FEATURE:
<221> NAME/KEY: modified_base
```

```
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 28
ngtaacacct ggacctgtcg agcatccagc t                                   31

<210> SEQ ID NO 29
<211> LENGTH: 23
<212> TYPE: DNA
<213> ORGANISM: Artificial sequence
<220> FEATURE:
<223> OTHER INFORMATION: Synthetic oligo Ah 201
<220> FEATURE:
<221> NAME/KEY: modified_base
<222> LOCATION: (23)..(23)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 29
tctggattgc atcgggagtt acn                                            23

<210> SEQ ID NO 30
<211> LENGTH: 56
<212> TYPE: DNA
<213> ORGANISM: Artificial sequence
<220> FEATURE:
<223> OTHER INFORMATION: Synthetic oligo Ah 133
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 30
ngtaactcct gtgtaagctg cctgtcagtc ggtactgacc tgtcgagcat ccagct        56

<210> SEQ ID NO 31
<211> LENGTH: 56
<212> TYPE: DNA
<213> ORGANISM: Artificial sequence
<220> FEATURE:
<223> OTHER INFORMATION: Synthetic oligo Ah 134
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 31
ngtaactgct gtgtaagctg cctgtcagtc ggtactgacc tgtcgagcat ccagct        56

<210> SEQ ID NO 32
<211> LENGTH: 56
<212> TYPE: DNA
<213> ORGANISM: Artificial sequence
<220> FEATURE:
<223> OTHER INFORMATION: Synthetic oligo Ah 135
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 32
```
ngtaactggt gtgtaagctg cctgtcagtc ggtactgacc tgtcgagcat ccagct        56

<210> SEQ ID NO 33
<211> LENGTH: 76
<212> TYPE: DNA
<213> ORGANISM: Artificial sequence
<220> FEATURE:
<223> OTHER INFORMATION: Synthetic oligo AH 142
<220> FEATURE:
<221> NAME/KEY: modified_base
<222> LOCATION: (76)..(76)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 33
cgacctctgg attgcatcgg tcatttttt tttttttttt ttttggctga ctgtccgtcg    60
aatgtgtcca gttacn                                                   76

<210> SEQ ID NO 34
<211> LENGTH: 21
<212> TYPE: DNA
<213> ORGANISM: Artificial sequence
<220> FEATURE:
<223> OTHER INFORMATION: Synthetic oligo AH 156
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 34
ngacctgtcg agcatccagc t                                             21

<210> SEQ ID NO 35
<211> LENGTH: 21
<212> TYPE: DNA
<213> ORGANISM: Artificial sequence
<220> FEATURE:
<223> OTHER INFORMATION: Synthetic oligo AH 202
<220> FEATURE:
<221> NAME/KEY: modified_base
<222> LOCATION: (21)..(21)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 35
tctggattgc atcgggttac n                                             21

<210> SEQ ID NO 36
<211> LENGTH: 21
<212> TYPE: DNA
<213> ORGANISM: Artificial sequence
<220> FEATURE:
<223> OTHER INFORMATION: Synthetic oligo AH 203
<220> FEATURE:
<221> NAME/KEY: modified_base
<222> LOCATION: (21)..(21)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 36
tctggattgc atcggttttt n                                             21

<210> SEQ ID NO 37
<211> LENGTH: 30

```
<212> TYPE: DNA
<213> ORGANISM: Artificial sequence
<220> FEATURE:
<223> OTHER INFORMATION: Synthetic oligo AH 236
<220> FEATURE:
<221> NAME/KEY: modified_base
<222> LOCATION: (1)..(1)
<223> OTHER INFORMATION: modified guanine, guanine modified with
      5'-Amino-modifier 5 (obtained from Glen Research, catalogue # 10-
      1905-90)

<400> SEQUENCE: 37
ntaacacctg gacctgtcga gcatccagct                                         30

<210> SEQ ID NO 38
<211> LENGTH: 31
<212> TYPE: DNA
<213> ORGANISM: Artificial sequence
<220> FEATURE:
<223> OTHER INFORMATION: Synthetic oligo AH 240
<220> FEATURE:
<221> NAME/KEY: modified_base
<222> LOCATION: (31)..(31)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 38
cgacctctgg attgcatcgg gcacggttac n                                       31

<210> SEQ ID NO 39
<211> LENGTH: 31
<212> TYPE: DNA
<213> ORGANISM: Artificial sequence
<220> FEATURE:
<223> OTHER INFORMATION: Synthetic oligo AH 249
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 39
nctggacagc tcgtaggtcg tttttttttt t                                       31

<210> SEQ ID NO 40
<211> LENGTH: 21
<212> TYPE: DNA
<213> ORGANISM: Artificial sequence
<220> FEATURE:
<223> OTHER INFORMATION: Synthetic oligo AH 251
<220> FEATURE:
<221> NAME/KEY: modified_base
<222> LOCATION: (1)..(1)
<223> OTHER INFORMATION: modified thymine, base derived from Amino
      modifier C6 dT (obtained from Glen Research, catalogue # 10-1039-
      90)

<400> SEQUENCE: 40
ngacctgtcg agcatccagc t                                                  21

<210> SEQ ID NO 41
<211> LENGTH: 21
<212> TYPE: DNA
<213> ORGANISM: Artificial sequence
<220> FEATURE:
<223> OTHER INFORMATION: Synthetic oligo AH 252
<220> FEATURE:
<221> NAME/KEY: modified_base
<222> LOCATION: (1)..(1)
```

```
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 41
ngacctgtcg agcatccagc t                                              21

<210> SEQ ID NO 42
<211> LENGTH: 27
<212> TYPE: DNA
<213> ORGANISM: Artificial sequence
<220> FEATURE:
<223> OTHER INFORMATION: Synthetic oligo AH 255
<220> FEATURE:
<221> NAME/KEY: modified_base
<222> LOCATION: (27)..(27)
<223> OTHER INFORMATION: modified thymine, base derived from Amino
      modifier C6 dT (obtained from Glen Research, catalogue # 10-1039-
      90)

<400> SEQUENCE: 42
cgacctctgg attgcatcgg tgttacn                                        27

<210> SEQ ID NO 43
<211> LENGTH: 26
<212> TYPE: DNA
<213> ORGANISM: Artificial sequence
<220> FEATURE:
<223> OTHER INFORMATION: Synthetic oligo AH 258
<220> FEATURE:
<221> NAME/KEY: modified_base
<222> LOCATION: (26)..(26)
<223> OTHER INFORMATION: modified thymine, base derived from Amino
      modifier C6 dT (obtained from Glen Research, catalogue # 10-1039-
      90)

<400> SEQUENCE: 43
acgactacgt tcaggcaaga gttacn                                         26

<210> SEQ ID NO 44
<211> LENGTH: 31
<212> TYPE: DNA
<213> ORGANISM: Artificial sequence
<220> FEATURE:
<223> OTHER INFORMATION: Synthetic oligo AH 260
<220> FEATURE:
<221> NAME/KEY: modified_base
<222> LOCATION: (1)..(1)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 44
nctggacagc tcgtaggtcg tttttttttt t                                   31

<210> SEQ ID NO 45
<211> LENGTH: 21
<212> TYPE: DNA
<213> ORGANISM: Artificial sequence
<220> FEATURE:
<223> OTHER INFORMATION: Synthetic oligo AH 261
<220> FEATURE:
<221> NAME/KEY: modified_base
<222> LOCATION: (21)..(21)
<223> OTHER INFORMATION: modified thymine, base derived from Amino
      modifier C6 dT (obtained from Glen Research, catalogue # 10-1039-
      90)

<400> SEQUENCE: 45
cgacctctgg attgcatcgg n                                              21
```

-continued

```
<210> SEQ ID NO 46
<211> LENGTH: 25
<212> TYPE: DNA
<213> ORGANISM: Artificial sequence
<220> FEATURE:
<223> OTHER INFORMATION: Synthetic oligo AH 262
<220> FEATURE:
<221> NAME/KEY: modified_base
<222> LOCATION: (25)..(25)
<223> OTHER INFORMATION: modified thymine, base derived from Amino
      modifier C6 dT (obtained from Glen Research, catalogue # 10-1039-
      90)

<400> SEQUENCE: 46
cgacctctgg attgcatcgg ttacn                                          25

<210> SEQ ID NO 47
<211> LENGTH: 25
<212> TYPE: DNA
<213> ORGANISM: Artificial sequence
<220> FEATURE:
<223> OTHER INFORMATION: Synthetic oligo AH 270
<220> FEATURE:
<221> NAME/KEY: modified_base
<222> LOCATION: (1)..(1)
<223> OTHER INFORMATION: 5'-amino modified guanine, guanine modified
      with 5'-Amino-modifier 5 (obtained from Glen Research, catalogue
      # 10-1905-90)

<400> SEQUENCE: 47
ntaacgacct gtcgagcatc cagct                                          25

<210> SEQ ID NO 48
<211> LENGTH: 27
<212> TYPE: DNA
<213> ORGANISM: Artificial sequence
<220> FEATURE:
<223> OTHER INFORMATION: Synthetic oligo AH 271
<220> FEATURE:
<221> NAME/KEY: modified_base
<222> LOCATION: (1)..(1)
<223> OTHER INFORMATION: 5'-amino modified guanine, guanine modified
      with 5'-Amino-modifier 5 (obtained from Glen Research, catalogue
      # 10-1905-90)

<400> SEQUENCE: 48
ntaactggac ctgtcgagca tccagct                                        27

<210> SEQ ID NO 49
<211> LENGTH: 26
<212> TYPE: DNA
<213> ORGANISM: Artificial sequence
<220> FEATURE:
<223> OTHER INFORMATION: Synthetic oligo AH 272
<220> FEATURE:
<221> NAME/KEY: modified_base
<222> LOCATION: (26)..(26)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 49
acgactacgt tcaggcaaga gttacn                                         26

<210> SEQ ID NO 50
<211> LENGTH: 28
<212> TYPE: DNA
<213> ORGANISM: Artificial sequence
<220> FEATURE:
```

<223> OTHER INFORMATION: Synthetic oligo AH 273
<220> FEATURE:
<221> NAME/KEY: modified_base
<222> LOCATION: (28)..(28)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 50
acgactacgt tcaggcaaga gcgttacn                                      28

<210> SEQ ID NO 51
<211> LENGTH: 31
<212> TYPE: DNA
<213> ORGANISM: Artificial sequence
<220> FEATURE:
<223> OTHER INFORMATION: Synthetic oligo AH 274
<220> FEATURE:
<221> NAME/KEY: modified_base
<222> LOCATION: (31)..(31)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 51
acgactacgt tcaggcaaga gcacggttac n                                  31

<210> SEQ ID NO 52
<211> LENGTH: 28
<212> TYPE: DNA
<213> ORGANISM: Artificial sequence
<220> FEATURE:
<223> OTHER INFORMATION: Synthetic oligo AH 275
<220> FEATURE:
<221> NAME/KEY: modified_base
<222> LOCATION: (28)..(28)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 52
cgacctctgg attgcatcgg gcgttacn                                      28

<210> SEQ ID NO 53
<211> LENGTH: 31
<212> TYPE: DNA
<213> ORGANISM: Artificial sequence
<220> FEATURE:
<223> OTHER INFORMATION: Synthetic oligo AH 276
<220> FEATURE:
<221> NAME/KEY: modified_base
<222> LOCATION: (31)..(31)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 53
ctggtaacgc ggatcgacct gcacggttac n                                  31

<210> SEQ ID NO 54
<211> LENGTH: 28
<212> TYPE: DNA
<213> ORGANISM: Artificial sequence
<220> FEATURE:
<223> OTHER INFORMATION: Synthetic oligo AH 277
<220> FEATURE:
<221> NAME/KEY: modified_base
<222> LOCATION: (28)..(28)
<223> OTHER INFORMATION: modified thymine, Carboxy -dT; obtained by
      modification using carboxymodifier C2 dT (obtained from Glen
      Research, catalogue number 10-1035-90)

<400> SEQUENCE: 54
ctggtaacgc ggatcgacct gcgttacn                                              28

<210> SEQ ID NO 55
<211> LENGTH: 80
<212> TYPE: DNA
<213> ORGANISM: Artificial sequence
<220> FEATURE:
<223> OTHER INFORMATION: Synthetic oligo AH 38

<400> SEQUENCE: 55
agctggatgc tcgacaggtc aggtcgatcc gcgttaccag tcttgcctga acgtagtcgt          60
ccgatgcaat ccagaggtcg                                                      80

<210> SEQ ID NO 56
<211> LENGTH: 87
<212> TYPE: DNA
<213> ORGANISM: Artificial sequence
<220> FEATURE:
<223> OTHER INFORMATION: Synthetic template AH 154

<400> SEQUENCE: 56
agctggatgc tcgacaggtc aagtaacagg tcgatccgcg ttaccagtct tgcctgaacg          60
tagtcgtccg atgcaatcca gaggtcg                                              87

<210> SEQ ID NO 57
<211> LENGTH: 36
<212> TYPE: DNA
<213> ORGANISM: Artificial sequence
<220> FEATURE:
<223> OTHER INFORMATION: Synthetic template AH 250

<400> SEQUENCE: 57
cgacctacga gctgtccaga agtaacaggt cgatcc                                    36

<210> SEQ ID NO 58
<211> LENGTH: 90
<212> TYPE: DNA
<213> ORGANISM: Artificial sequence
<220> FEATURE:
<223> OTHER INFORMATION: Synthetic template AH 256

<400> SEQUENCE: 58
agctggatgc tcgacaggtc aagtaacacc aggtcgatcc gcgttaccag tcttgcctga          60
acgtagtcgt ccgatgcaat ccagaggtcg                                           90

<210> SEQ ID NO 59
<211> LENGTH: 86
<212> TYPE: DNA
<213> ORGANISM: Artificial sequence
<220> FEATURE:
<223> OTHER INFORMATION: Synthetic template AH 263

<400> SEQUENCE: 59
cgacctacga gctgtccaga agtaacaggt cgatccgcgt taccagtctt gcctgaacgt          60
agtcgtctgg tcacgtggat ccttga                                               86

<210> SEQ ID NO 60
<211> LENGTH: 81
<212> TYPE: DNA
<213> ORGANISM: Artificial sequence
<220> FEATURE:

-continued

```
<223> OTHER INFORMATION: Synthetic template AH 278

<400> SEQUENCE: 60
agctggatgc tcgacaggtc gaggtcgatc cgcgttacca gtcttgcctg aacgtagtcg    60
tccgatgcaa tccagaggtc g                                             81

<210> SEQ ID NO 61
<211> LENGTH: 85
<212> TYPE: DNA
<213> ORGANISM: Artificial sequence
<220> FEATURE:
<223> OTHER INFORMATION: Synthetic template 279

<400> SEQUENCE: 61
cgacctacga gctgtccaga agtaactttt tttttttttt tttttttttt tttttttttt   60
tttttctggt cacgtggatc cttga                                         85

<210> SEQ ID NO 62
<211> LENGTH: 34
<212> TYPE: DNA
<213> ORGANISM: Artificial sequence
<220> FEATURE:
<223> OTHER INFORMATION: Synthetic template containing a modified
      nucleobase having a S-triphenylmethyl protected thio moiety, used
      in example 13
<220> FEATURE:
<221> NAME/KEY: modified_base
<222> LOCATION: (1)..(1)
<223> OTHER INFORMATION: thymine modified by connection through biotin
      phosphoramidite (Glen Research 10-1953-95) to base 17 of SEQ ID
      NO:25

<400> SEQUENCE: 62
ngtcagtcgg tactgtggta acgcggatcg acct                               34

<210> SEQ ID NO 63
<211> LENGTH: 43
<212> TYPE: DNA
<213> ORGANISM: Artificial sequence
<220> FEATURE:
<223> OTHER INFORMATION: Synthetic template containing a modified
      nucleobase having a S-triphenylmethyl protected thio moiety, used
      in example 13
<220> FEATURE:
<221> NAME/KEY: modified_base
<222> LOCATION: (1)..(1)
<223> OTHER INFORMATION: thymine modified by connection through biotin
      phosphoramidite (Glen Research 10-1953-95) to base 17 of SEQ ID
      NO:26

<400> SEQUENCE: 63
naagctgcct gtcagtcggt actacgacta cgttcaggca aga                     43
```

METHOD FOR SYNTHESISING TEMPLATED MOLECULES

TECHNICAL FIELD OF THE INVENTION

The present invention relates to a method for synthesising templated molecules. The method implies a high local concentration of reactive groups intended to participate in a formation of a linkage, thus increasing the probability of linkage formation. The invention also relates to a library, that is a plurality of templated molecules, wherein each of the templated molecules are attached to the template which directed the synthesis thereof.

BACKGROUND

The generation of molecules carrying new properties remains a challenging task. Recently, a number of procedures have been suggested that should allow a more efficient generation and screening of a larger number of molecules. The approaches taken involve the encoding and/or templating of molecules other than natural biopolymers such as peptide, RNA and DNA. These approaches allow the researcher to generate and screen a huge number of molecules in a short time. This should lead to better molecules carrying the desired properties.

The central dogma of biology describes the one-way flow of information from DNA to RNA to protein. Recently, methods such as phage display, peptides-on-plasmids, ribosome display and mRNA-protein fusion have been developed, allowing the transfer of information from the level of protein/peptide to RNA or DNA. This has enabled the use of molecular evolution to be applied on huge numbers of peptides that are exposed to an enrichment process, where after the enriched pool of molecules (enriched for a particular feature, such as binding to receptor protein) are amplified, by exploiting information flow from the peptide to DNA and then amplifying the DNA.

More recently, approaches have been developed that allow the encoding of polypeptides and other biochemical polymers. An example of this approach is disclosed in U.S. Pat. No. 5,723,598, which pertains to the identification of a biochemical polymer that participates in a preselected binding interaction with a target to form a binding reaction complex. The prior art method encompasses the generation of a library of bifunctional molecules. One part of the bifunctional molecule is the biochemical polymer and the other part is an identifier oligonucleotide comprising a sequence of nucleotides which encodes and identifies the biochemical polymer. Following the generation of the library of the bifunctional molecules, a partitioning with respect to affinity towards the target is conducted and the identifier oligonucleotide part of the bifunctional molecule is amplified by means of PCR. Eventually, the PCR amplicons are sequenced and decoded for identification of the biochemical polymer. This approach does not, however, allow one-pot amplification of the library members. Furthermore, the sequence of nucleotides serves to identify the biochemical molecule only after a laborious sequencing process. Thus the flow of information from the identifier sequence to the biochemical polymer is restrained.

Halpin and Harbury have in WO 00/23458 suggested an improvement to the approach stipulated immediately above, wherein the molecules formed are not only identified but also directed by the nucleic acid tag. The approach is based on the traditional split-and-combine strategy for synthesis of combinatorial libraries comprising two or more synthetic steps. Plurality nucleic acid templates are used, each having at one end a chemical reactive site and dispersed throughout the stand a plurality of codons regions, each of said codon regions in turn specifying different codons. Separately, each of the strands, identified by a first codon region, is reacted at the chemical reaction sites with specific selected reagents. Subsequently, all the strands are pooled and subjected to a second partitioning based on a second codon region. The split-and-combine method is conducted an appropriate number of times to produce a library of typically between $10^3$ and $10^6$ different compounds. The split-and-combine method is cumbersome and generates only a relatively small library.

Gartner Z J and Liu D R (*J. Am. Chem. Soc.* 2001, 123, 6961-6963) discloses a method in which DNA is used to direct chemical reactions sequence-specifically. It is shown that the proximity effect provided by DNA-templated synthesis can be used to promote chemical reactions. When more than a single chemical entity is to participate in the formation of an encoded molecule, it is necessary to have a building block spaced from a reactive site of the template by one or more codons. Typically, the distance between the building block and the reactive site of the template amounts to several nucleotides, e.g. 30 nucleotides, which implies that the reaction at the largest distance from the template reactive site is less promoted relative to a chemical entity carried by a building block annealed to a codon next to the reactive site.

The present invention aims at suggesting a solution for increasing the local concentration of reactants to promote the probability of a reaction.

SUMMARY OF THE INVENTION

The present invention provides a method for synthesising a templated molecule, said method comprising the steps of:
a) providing at least one template comprising of one or more codons,
b) providing a first functional entity attached to a zipping domain, said zipping domain comprises a first part of a molecule pair, being capable of reversible interaction with a second part of the molecule pair,
c) providing one or more building blocks, each comprising an anti-codon, a further functional entity and a linker connecting the anti-codon and the functional entity, wherein the anti-codon complements a codon of a template, and the functional entity is connected to a zipping domain comprising the second part of said molecule pair and is capable of being chemically connected to the first functional entity,
d) contacting the components of step a), b), and c) with each other under conditions allowing specific hybridisation of the anti-codon(s) to the codon(s) of the template(s) and dimerization of the two parts of the molecule pair,
e) allowing the functional entity of the building block to form a chemical connection to the first functional entity,
f) optionally, cleaving one or more linkers, provided that at least one linker remains to connect the functional entities with the template,
g) obtaining a templated molecule attached to the template which directed the synthesis thereof.

The template comprises in a preferred embodiment two or more codons, such as three to fifteen codons. The first functional entity, which in an aspect of the invention can be a scaffold, can then be connected to two or more functional entities. The method may be conducted only once to connect a scaffold functional entity with the desired amount of functional entities or the steps of d) through g) may be repeated one or more times to sequentially add building blocks harbouring functional entities to be attached to a functional entity or a nascent templated molecule.

When multi-step synthesis is performed, the repetition of the steps d) through g) is conducted using the templated molecule attached to the template which directed the synthesis thereof according to step g) as the first functional entity attached to a zipping domain in the contacting step according to step d).

The zipper domains may be characterized as two interacting moieties able to reversibly dimerize in an ordered way, thereby bringing reactive groups attached to them into close proximity. Reversibility is required in a preferred aspect in order to allow different functional entities having the same dimerization domain to interact at different times with a complementary zipper domain attached to a reactive site. Many types of molecular moieties may be employed as zipper domains, of which here follows a non-comprehensive list of appropriate pairs of zipper domains: i) DNA/DNA, DNA/RNA, LNA/DNA, PNA/RNA, various combinations of nucleotides and nucleotide analogs; ii) peptide/peptide, e.g. base and acid leucine zipper (coiled coil structure of two alpha-helices), antibody/antigen; iii) nucleic acidpeptide, e.g. Zinck-finger DNA binding domain/dsDNA; iv) peptide/small organic molecule, e.g., streptavidin/biotin; v) small organic molecule/small organic molecule, e.g., nitrilotriacetic acid (NTA)/nitrilotriacetic acid (NTA)-$Zn^{++}$; vi) positively charged moiety/negatively charged moiety, e.g., polyglutamic acid/polylysine. The zipper box can be chosen according to the conditions of the reaction that it is supposed to enhance. For example, if the reaction is performed at moderate temperature and at reasonably high salt concentration, DNA/DNA zipper boxes may be used. By varying the length of the zipper box (the complementary DNA strands), one may design zipper boxes of desired stability and dynamics. Other types of zipper boxes will be very dependent on pH. For example, the interaction strength and dynamics of a glutamate/lysine pair will be dependent on pH, as for example the polyglutamate will be highly negatively charged at high pH, and not charged at all at low pH.

The functional entity is in an aspect of the invention attached to the template through one or more covalent links. However, it may be appropriate that the first functional entity is connected to a sequence of nucleic acids complementing a sequence of nucleic acids harboured by the template to enable the attachment of a scaffold to the template by hybridisation. In this way it will be possible to encode several different scaffolds by the template. In a preferred embodiment of the invention, the first functional entity is a scaffold, i.e. a chemical moiety which is amended, usually by addition of functional groups emanating from one or more building blocks. The scaffold may be a single reactive group or a chemical structure comprising two or more reactive groups. Usually, the scaffold remains attached to the template through-out the synthesis of the templated molecule.

Usually, when the zipping domain comprises nucleic acids, the polarity of the building block harbouring the first functional entity is reverse compared to the polarity of the building block harbouring the further functional entity, i.e. if the first functional entity is attached to the 5' end of an oligonucleotide, the further functional entity is preferably attached to the 3' end of building block oligonucleotide, or visa versa. In certain aspects, when more than a single building block is included in the formation of the templated molecule, it is preferred that the scaffold building block is annealed to a flanking position of the template, i.e. not placed between codons codon for building blocks.

The zipping domain may be placed relative to the first functional entity in any way that promotes the proximity of the functional entities. In one aspect, the zipping domain is present in the template. In one setup, the zipping domain is situated between a codon coding for a scaffold oligo and the codons coding for building blocks. In another aspect of the invention the zipping domain is a part of the linker of the building block. Preferably, the zipping domain is proximal to the functional entity. Still more preferred the zipping domain is spaced from the functional entity with no more than 2 nucleic acids monomers. In a most preferred embodiment, the zipping domain of the functional entity of the building block and the first functional entity is distanced from the respective entities with the same number of nucleic acid monomers to provide for a high local concentration of functional entities. The distance of the zipping domain of the functional entity of the building block and the first functional entity, respectively, to the functional entities are preferably zero nucleotide monomers. In other words, it is preferred that the two functional entities intended to form a connection is attached to the terminal nucleotide of the zipping domain.

The desired number of the nucleic acid monomers of the zipping domain depends largely on the temperature and stringency conditions in general used during the synthesis. If a low stringency and/or a relatively low temperature is preferred the number of nucleic acid monomers may be as low as 3. However, a low number of nucleic acid monomers in the sequence of the zipping domain may increase the risk of hybridisation to e.g. the template or building blocks. It is therefore, in general, preferred to use at least 4 nucleic acid monomers. According to a preferred embodiment of the invention the zipping domain sequence comprises 3 to 20 nucleic acid monomers. In a still more preferred embodiment the zipping domain sequence comprises 4 to 16 nucleic acid monomers. Most preferred is a zipping domain sequence comprising 5 to 10 nucleic acid monomers.

The linkage between the anti-codon and the a zipping domain may be a single bond or a chemical moiety up to several 100 Å, such as between 1 and 300 Å. The linkage may be of any suitable chemical nature, however, it is in general preferred that the linkage is an oligonucleotide. In a preferred embodiment, the linkage is a single bond, i.e. the anti-codon abuts the zipping domain.

In a preferred aspect of the invention, the annealing temperature of the codon:anti-codon hybrid is higher than the annealing temperature of the zipping domain hybrid to ensure that the building block remain attached to the template even though the interaction of the zipping domains is eliminated. The above aspect is specifically preferred when the contacting according to step d) is performed by alternating the temperature below and above the annealing temperature of the zipping domain. The effect of the alternation is increased when the alternating is performed a plurality of times. To avoid the release of the building block from the template, the highest temperature is preferably below the annealing temperature of the codon:anti-codon hybrid.

According to a preferred aspect of the invention, when the template comprises two or more codons the building blocks attached to these codons have essentially identical sequences of the zipping domain. An alternation of the temperature will then attract the different functional entities annealed through building blocks to the scaffold. Thus, it is possible to have a variety of functional entities brought into close proximity of the scaffold.

The difference between the annealing temperatures of the codon:anti-codon hybrid and the dimerized zipping domains is suitably 10° C. or above. More preferred the difference between the annealing temperatures is 25° C. or above.

In an aspect of the invention the hybridisation of codons with anti-codons and zipper domain dimerisation occurs in separate steps, i.e. the conditions for allowing specific hybridisation of the anti-codon(s) to the codon(s) of the template(s) are distinct from the conditions allowing for optimal dimerisation of the two pairs of the molecule pair. The separation of the step provides for optimal conditions for each step. In the second step, the dimerisation step, it is preferred to use conditions that ensures that the codons and anti-codons remains attached and conditions that favours reaction between the functional entities.

The conditions during specific hybridisation of the anti-codon(s) to the codon(s) suitably include a concentration of codons and/or anti-codons, which is higher than the concentration of codons and/or anti-codons used during dimerisation of the two pairs of the molecule pair. The difference in concentration enhance the probability that the codon:anti-codon hybrid has been formed prior to the reaction of the functional entities, thereby ensuring the transfer of genetic information. Suitably, the the concentration during hybridisation of codon(s) and anti-codons is at least 10 times higher compared to the concentration used for dimerisation of the two pairs of the zipping domain. The diluted conditions during the zipping domain dimerisation also favours the template directed reactions rather cross-reactions among random reactive groups appearing in the media because the local concentration of encoded reactive groups relative to the concentration of reactive groups in general in the media is increased.

In an aspect of the invention, the method is used to generate a library of templated molecules attached to the template (or, alternatively, a complementing template) which directed the synthesis of the molecule. As an example, a library may be generated by having more than one possible codon:anti-codon interaction. This may be conducted by having several building blocks with different functional entities but similar anti-codons. However, to obtain a one-to-one relationship between the identity of the functional entity connected to the scaffold and the codon of the template, it is usually preferred that each building block carries a specific anti-codon which identify the functional entity.

A library preferably comprises a plurality of templates with different unique codons and/or order of unique codons. A plurality of building blocks having anti-codons corresponding to the unique codons of the templates is usually provided. In one aspect of the invention, a specific building block is provided for each of the unique codons. In another aspect some of the codons are not matched by a building block or alternatively blocked by a oligonucleotide sequence without a functional entity.

In the following the principle is illustrated for a specific non-limiting example. The anti-codons in this example are approximately 20 nucleotides long (and has a melting temperature towards its complementary sequence of approximately 60° C.), whereas the zipper domain is approximately 5 nucleotides long (and has a much lower melting temperature, e.g. around 17° C.). The building blocks and the plurality of templates are incubated together, at a medium temperature (e.g., 55° C.), allowing the anti-codons to find and bind to the corresponding codons. At this temperature, the anti-codons interact efficiently and specifically with the codons, whereas the zipper boxes do not interact efficiently. Excess un-bound building blocks are washed away. Then the reactions between reactive groups of neighbouring functional entities are initiated by lowering the temperature to e.g. 10° C., and potentially changing conditions other than the temperature. At 10° C. the zipper domains of the regular building blocks will interact with the complementary sequence of the zipper domain of the scaffold functional entity, thereby bringing the reactive groups into very close proximity (see FIG. 14). This increases the local concentration of the reactive groups significantly, and as a result the reactive groups react. Then again, the temperature is increased to the medium temperature (55° C.) and the zipping box is melted resulting in a separation of the functional entities. When the temperature subsequently is decreased to about 10° C., another building block may hybridize its zipper domain to the zipper domain of the scaffold, whereafter its functional entity may react with the scaffold.

BRIEF DESCRIPTION OF THE FIGURES

The following figures are referred to in this description:

FIG. 13 shows a schematic drawing of the use of a dimerisation domain in the synthesis of (A) a scaffolded molecule and (B) a polymeric molecule.

FIG. 16 disclose two oligo setups used in the examples.

FIG. 24 discloses the results of experiments E to H reported in example 21.

Zipping Domains

Figure 1:
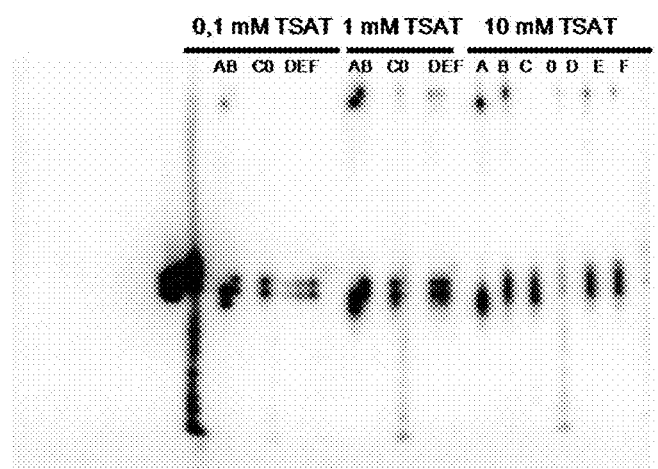
FIG. 1 shows a reproduction of a PAGE gel displaying cross-linking of amino functionalities of two oligonucleotides annealed to a common template.

The zipper box is a molecular affinity pair composed of two parts which has affinity for each other under certain environmental conditions. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, proteinpolysaccharide interactions, RNA-protein interactions, DNA-DNA interactions, DNA-RNA interactions, RNA-RNA interactions, biotin-streptavidin interactions, enzyme-ligand interactions, antibody-ligand interaction, protein-ligand interaction, etc.

The interaction between the molecular affinity parts may result in a strong or a week bonding. If a covalent bond is formed between the parties of the affinity pair the binding between the parts can be regarded as strong, whereas the establishment of hydrogen bondings, interactions between hydrophobic domains, and metal chelation in general results in a week bonding. In general relatively weak bonding is preferred. In a preferred aspect of the invention, the first part of the affinity pair is capable of reversible interacting with the second part of the affinity pair so as to provide for an attachment or detachment of the parts in accordance with the changing conditions of the media.

In a preferred aspect of the invention, the molecular affinity pair is based on an interaction between nucleotides, i.e. the first part of the affinity pair is a sequence of nucleotides and the second part of the affinity pair is a sequence of nucleotides capable of hybridising to the first part of the affinity pair. The first part of the affinity pair may be a part of the template or a building block and may comprise an oligonucleotide having nucleobases selected among the natural occurring nucleobases, i.e. adenine, cytosine, guanine, thymine, and uracil which are attached to a backbone, such as a repetitive sequence of (deoxy)ribose-phosphate units. The second part of the affinity pair can be an oligonucleotide having nucleobases which complements and is specifically recognised by the first part, i.e. in the event the first part contains cytosine, the second part contains guanine and visa versa, and in the event the first part contains thymine or uracil the second part contains adenine. In one aspect of the invention it is preferred however, that at least some of the nucleobases of the second part of the affinity pair are non-specific base-pairing nucleobases. Non-specific base-pairing nucleobases are bases which, when attached to a backbone, are able to pair with at least two of the five naturally occurring nucleobases mentioned above. Preferably, the base pairing between the two or more natural nucleobases and the non-specifically base-pairing nucleobase occurs essentially isoenegically, i.e. the bonds formed have a strength of the same order. The term "non-specifically base-pairing nucleobase" is used herein interchangeably with the term "universal base".

In natural tRNA the nucleobase inosine is found. Inosine has the ability to hybridise non-specifically with three of the nucleobases, i.e. cytosine, thymine, and adenine. Other synthetic compounds having the same ability of non-specifically base-pairing with natural nucleobases have been formed and includes among others the compounds depicted below Examples of Universal Bases

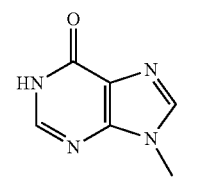

Inosine

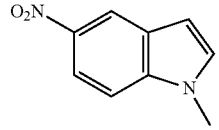

5-Nitroindole

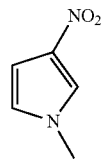

3-Nitropyrrole

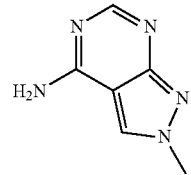

$N^8$-8aza-7deazaadenine

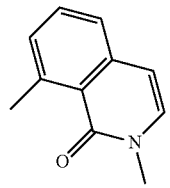

MICS

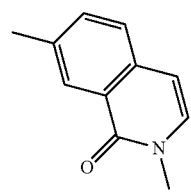

5MICS

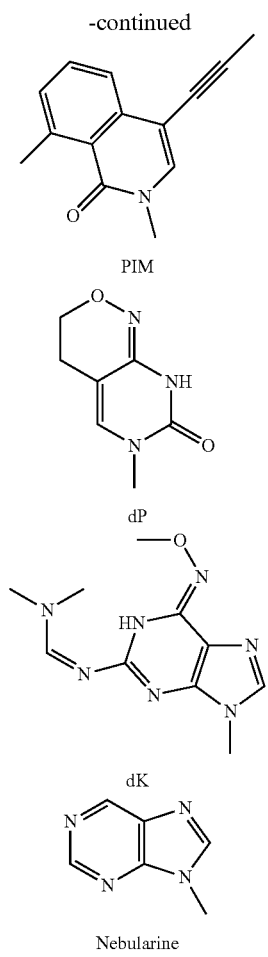

PIM dP dK

Nebularine

Template

The codons of the template may be any biochemical entity with an ability to be recognized specifically by another entity. It is preferred, however, that the codon is a sequence of nucleotides. The sequence of nucleotides carries a series of nucleobases on a back bone. The nucleobases of the codons may be any chemical entity able to be specifically recognized by a complementing entity. The nucleobases are usually selected from the natural nucleobases (adenine, guanine, uracil, thymine, and cytosine) but also the other nucleobases obeying the Watson-Crick hydrogen-bonding rules may be used, such as the synthetic nucleobases disclosed in U.S. Pat. No. 6,037,120.

The codon may be a single nucleotide. In the generation of a library, this will allow for the incorporation of four different functional entities into the template-directed molecule. However, to obtain a higher diversity a codon preferably comprises at least two and more preferred at least three nucleotides. Theoretically, this will provide for $4^2$ and $4^3$, respectively, different functional entities. The codons will usually not comprise more than 100 nucleotides. It is preferred to have codons with a sequence of 3 to 30 nucleotides.

The at least two codons of the template are arranged in sequence, i.e. next to each other and may be separated by a spacer group. Depending on the template-directed molecule intended to be formed, the template may comprise further codons. Each of the further codons may be separated by a suitable spacer group. Preferably, all or at least a majority of the codons of the template are arranged in sequence and each of the codons are separated from a neighbouring codon by a spacer group. Generally, it is preferred to have more than two codons on the template to allow for the synthesis of more complex template-directed molecules. In a preferred aspect of the invention the number of codons of the template is 2 to 100. Still more preferred is templates comprising 3 to 15 codons.

The spacer sequence may serve various purposes. In one setup of the invention, the spacer group identifies the position of a codon. Usually, the spacer group either upstream or downstream of a codon comprises information which allows determination of the position of the codon. The spacer group may also or in addition provide for a region of high affinity. The high affinity region will ensure that the hybridisation of the template with the anti-codon will occur in frame. Moreover, the spacer sequence adjusts the annealing temperature to a desired level.

A spacer sequence with high affinity can be provided by incorporation of one or more nucleobases forming three hydrogen bonds to a cognate nucleobase. An example of a nucleobase having this property is guanine. Alternatively, or in addition, the spacer sequence may be subjected to back bone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The template may comprise flanking regions. One of the flanking regions can in an aspect of the invention serve to immobilize the template to a surface of a solid support such as a microarray. In another aspect of the invention the flanking region can encompasses a signal group, such a flourophor or a radio active group, to allow a direct detection of the presence of the template. The flanking regions can also serve as priming sites for an amplification reaction, such as PCR.

The template may also be immobilised on a solid support, such as a bead or matrix material by incorporating a biotin group in the template and subsequent coupling to a streptavidin coated solid support. Various other immobilisation methods are known to the skilled person, including coupling of the template to an antibody and immobilising the conjugate to a solid support coated with the appropriate antigen. In a preferred aspect, the priming site of the template serves the dual purpose of participating in an amplification reaction and as the means for immobilisation. The immobilisation can be effected, e.g. by treatment of the template comprising the priming site with a solid support comprising oligonucleotide sequences complementary to the priming site.

In one aspect, the first functional entity is covalently attached to the template. The covalent attachment of the reactive group usually entails that the template-directed molecule is formed at or in the vicinity of said reactive group. The final template-directed molecule is thus covalently attached to the template which directed and encoded the synthesis thereof. In the event a library is formed which comprises a plurality of complexes prepared in accordance with the invention, high stringency conditions for a selection procedure may be used without the risk of separating the template-directed molecule from the template.

In another aspect of the invention, the first functional entity is non-covalently attached to the template. Usually, the non-covalently attachment involves hydrogen bonds and hydrophobic interaction. Notably, the non-covalent attachment involves a hybridisation reaction between oligonucleotides or a part thereof. In a preferred embodiment, the functional entity is attached to a sequence of nucleotides, which complements a sequence of nucleotides of the template. The complementing sequence having attached the reactive group can serve as an anchor, i.e. to tie the nascent template-directed molecule to the template. Usually, the complementing sequence of the anchor has an annealing temperature higher than each of the building blocks to ensure attachment of the anchor even under condition which detaches the building blocks.

The first functional entity, such as a scaffold, may be linked to the template through a selectively cleavable linker, which enables the separation of the template-directed molecule from the template at a time decided by the experimenter. The first functional entity generally comprises a reactive group. The reactive group can be a part of a nascent template-directed molecule which, possibly in amended form, appears in the final templated molecule. The reactive group can also be a part of a scaffold, such as a molecular entity comprising more than one reactive group. Furthermore, the reactive group may be in a pro-form that has to be activated before the method of the invention is initiated.

In the aspect of the invention relating to the generation of a library, it may be desired to couple the first functional entity to an anti-codon complementing a (further) codon on the template, thus making it possible to have more than a single kind of functional entities present in the media. Alternatively, a functional entity or scaffold comprising the reactive group(s) may be varied.

When the template is linear, the first part of the molecular affinity pair is usually arranged between the active codon and a functional entity or a nascent templated molecule covalently connected or connected by hybridisation to the template to provide for a closer proximity between the reactive groups. More preferred, the first part of the molecular affinity pair is arranged proximal relative to the template reactive group.

The second part of the molecular affinity pair is positioned in the building block. The second part of the molecular affinity pair may be dispensed with in the event the codon to which the building block is attached to is close to the template reactive group, or expressed in another way, the anti-codon of the building block may be at least partly identical to the second part of the molecular affinity pair. Building blocks having anti-codons intended to interact with codons distal to the template reactive group, such as a scaffold, comprise as a section of the linker the second part of the molecular affinity pair. The term "distal" is to be understood as the case in which the active codon, i.e. the codon hybridised to the anti-codon of the building block, is interspaced relative to the template reactive group with one or more inactive codon(s).

The second part of the molecular affinity pair in the linker of the building block is preferably arranged proximal to the functional entity to increase the proximity between the building block reactive group and the template reactive group. More preferred the second part of the molecular affinity pair is spaced from the nucleotide carrying the functional entity by 0 to two nucleotides.

Hybridisation Conditions

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design may be assisted by software, such as Vector NTI Suite or the public database at the internet address http://www.nwfsc.noaa.gov/protocols/oligoTMcalc.html.

The conditions which allow specific hybridisation of the codons and the anti-codons are influenced by a number of factors including temperature, salt concentration, type of buffer, and acidity. It is within the capabilities of the person skilled in the art to select appropriate conditions to ensure that the contacting between the templates and the building blocks are performed at hybridisation conditions. The temperature at which two single stranded oligonucleotides forms a duplex is referred to as the annealing temperature or the melting temperature. The melting curve is usually not sharp indicating that the annealing occurs over a temperature range. The second derivative of the melting curve is used herein to indicate the melting temperature.

Functional Entity

The functional entity of the building block serves the function of being a precursor for the structural entity eventually incorporated into the templated molecule. Therefore, when it in the present application with claims it is stated that a functional entity is transferred to a nascent template-directed molecule it is to be understood that not necessarily all the atoms of the original functional entity is to be found in the eventually formed template-directed molecule. Also, as a consequence of the reactions involved in the connection, the structure of the functional entity can be changed when it appears on the nascent templated molecule. Especially, the cleavage resulting in the release of the functional entity may generate a reactive group which in a subsequent step can participate in the formation of a connection between a nascent templated molecule and a functional entity.

The functional entity of the building block comprises at least one reactive group capable of participating in a reaction which results in a connection between the functional entity of the building block and the part of the template or complementing element hybridised to the template carrying the template reactive group. The connection is aided by one or more reactive groups of the functional entity. The number of reactive groups which appear on the functional entity is suitably one to ten. A building block featuring only one reactive group is used i.a. in the end positions of polymers, whereas building blocks having two reactive groups are suitable for the formation of the body part of a polymer or scaffolds capable of being reacted further. Two or more reactive groups intended for the formation of connections, are typically present on scaffolds. A scaffold may be a core structure, which forms the basis for the creation of multiple variants. The variant forms of the scaffold is typically formed through reaction of reactive groups of the scaffold with reactive groups of other building blocks, optionally mediated by fill-in groups or catalysts, under the creation of a connection between the entities. The functional entities to be connected to the scaffold may contain one, two or several reactive groups able to form connections.

The reactive group of the building block may be capable of forming a direct connection to a reactive group of another building block, nascent templated molecule or a template reactive site. In certain embodiments of the invention an indirect connection is formed using a bridging fill-in group. It is to be understood that not all the atoms of a functional entity necessarily is maintained in the (nascent) templated molecule formed. Rather, the functional entities are to be regarded as precursors for the structure of the final templated molecule.

The optional cleavage according to step f) can be performed in any appropriate way. In an aspect of the invention the cleavage involves usage of a reagent or and enzyme. The cleavage results in a transfer of the further functional entity to the nascent template-directed molecule or in a transfer of the nascent template-directed molecule to the functional entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the functional entity of the building block or the nascent template-directed molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

It is important for the method according to the invention that at least one linker remains intact after the cleavage step. The at least one linker will link the nascent template-directed molecule to the template that directed the synthesis thereof. In case the method essentially involves the transfer of functional entities to a scaffold or an evolving polymer, the eventually scaffolded molecule or the polymer may be attached with a selectively cleavable linker. The selectively cleavable linker is designed such that it is not cleaved under conditions which result in a transfer of the functional entity to the nascent template-directed molecule.

Building Block

The building blocks used in the method according to the present invention may be designed in accordance with the particular entities involved in the building block. As an example, the anti-codon may be attached to the second part of the molecular affinity pair with a polyethylene glycol (PEG) linker and the functional entity may be directly attached to the second part of the molecular affinity pair. In another and preferred example, the anti-codon, the linker and the second part of the molecular affinity pair is a contiguous linear oligonucleotide.

The attachment of the functional entity to the linker is preferably at a terminal nucleotide or a nucleotide 1 or two nucleotides down the oligonucleotide. The attachment of the functional entity can be at any entity available for attachment, i.e. the functional entity can be attached to a nucleotide of the oligonucleotide at the nucleobase, or the back bone. In general, it is preferred to attach the functional entity at the phosphor of the internucleoside linkage or at the nucleobase.

In an aspect of the invention, a reactive group of the functional entity is attached to the linker oligonucleotide. The reactive group is preferably of a type which is able to create a connection to the the nascent template-directed molecule by either direct reaction between the respective reactive groups or by using a suitable fill-in group. The reactive group coupling the functional entity with the linker is preferably cleaved simultaneously with the establishment of the connection. The functional entity may in some cases contain a second reactive group able to be involved in the formation of a connection in a subsequent cycle. The second reactive group may be of a type which needs activation before it is capable of participating in the formation of a connection.

The oligonucleotide linker may be distanced from the the functional entity by a spacer moiety. The spacer may be designed such that the conformational spaced sampled by the reactive group is optimized for a reaction with a reactive group of a nascent template-directed molecule.

The design of building blocks comprising the anti-codon may be aimed at obtaining annealing temperatures in a specific range for all or some of the building block:template hybrids to ensure that the anti-codons have been annealed to the template before the functional entities are connected to each other through a chemical reaction. When the building blocks anneals to the template with essentially the same affinity it is necessary to add the building blocks in each cycle, i.e. the contacting of the building blocks with the template involves separate addition of the individual building blocks.

In an aspect of the invention, the building blocks are designed such that the building block to be added to the template in the first cycle has an annealing temperature lower than the subsequent building blocks. By using a temperature for the connection step in a second or subsequent step which is higher the previous step it is possible to have only the intended building blocks annealed to the template, while the majority of previous spent or non-reacted building blocks will be single stranded. Optionally, a recovery step may be used between each cycle to enrich the number of single stranded template available for annealing to a subsequent building block. The recovery step may involve the incorporation of biotin in the building block oligonucleotide and separation of the building blocks from the template using steptavidin coated beads at a temperature above the annealing temperature, as described elsewhere herein.

After the cleavage step the parts of the molecular affinity pair are separated to allow for a subsequent building block to interact with the first part of the zipping domain. Optionally, the cleavage step may be performed after the separation of the molecular affinity pair. In case the molecular affinity pair is a double stranded oligonucleotide, the parts of the affinity pair may be separated by increasing stringency, e.g. by increasing the temperature. In the alternative, the second part of the affinity pair carried by the building block, can be degraded enzymatically or chemically as disclosed below.

After the reaction of a building block, e.g. by transfer of a functional entity to a scaffold, the anti-codon may remain annealed to the template during a subsequent cycle. However, it is in general preferred to remove the anti-codon of a reacted building block not harbouring the nascent template-directed molecule from the template prior to repetition of steps d) to g). The absence of the annealed anti-codon makes it possible to incorporate universal bases in the linker to obtain an affinity between the linker and the inactive previous used codons.

The anti-codon can be removed using various techniques, such as separation from the template by increasing the stringency, typically by raising the temperature; partly or fully enzymatical digestion; or chemical degradation. The approach using increasing the stringency is the most simple to apply. However, in the event reannealing can occur or selective removal of the anti-codon is desired, it can be contemplated to use enzymatic or chemical approaches or a mixture thereof.

A method for removal of spent building blocks, non-reacted building blocks and excess building blocks involves the incorporation of biotin or a similar small molecule and withdrawal of said building block using the adherence between biotin and avidine or streptavidine on coated beads.

More specifically, biotin is incorporated in the building block during the synthesis thereof. Following the transfer or alternatively the cleavage step of the invention, the mixture is treated with beads coated with streptavidin under conditions which allow for the coupling of streptavidin to biotin. Subsequently, the temperature is increased above the annealing temperature of the building block:template hybrid and the mixture is subjected to increased gravity, e.g by spinning in a centrifuge. The supernatant will then comprise the template liberated from the building blocks. An alternative to the biotin-streptavidin coupling is the formation of a S—S bridge. As an example, the oligonucleotide comprising the anti-codon is provided with a —SH group, such as a reduced product of the C6 S—S thiol modifier (Glen Research #10-1936-90). The —SH group of the building block can be coupled to another—SH group on a solid support under oxidising conditions and the building block can be removed together with the solid support by spinning if the solid material is a bead or by eluation if the solid support is a solid phase matrix of a column.

For some applications it may be of advantage to selectively degrade the anti-codon-containing oligonucleotide. Several methods are available for degradation of the RNA part of a DNA:RNA duplex. Accordingly, the template can be provided as a single stranded oligonucleotide and the anti-codon can be a single cognate RNA strand. The DNA:RNA duplex can then be degraded with an enzyme selected from RNAseH, RNAseA, RNAse 1. In the alternative, the RNA part of the RNA:DNA duplex can be degraded chemically by treatment under weak alkaline conditions (pH 9-10), or with aqueous $Pb(Ac)_2$.

If the internucleoside linker comprises a thiophosphate, the linker may be cleaved with iodine. Therefore, according to this approach, an oligonucleotide template, such as a DNA or RNA template having hybridised thereto a DNA or RNA anti-codon comprising a thiophospate in the internucleoside linker can be treated with aqueous iodine or iodoethanol to cleave the anti-codon.

According to another approach, a strand may be cleaved in a duplex if a DNA monomer contains a uracil nucleobase by first treating the duplex with uracil-glycosylase to remove the uracil moiety and subsequently treating with weak acid. Yet another approach involves the inclusion of methyl phosphonate in the internucleoside linker and cleavage of the linker using piperidine, e.g. by treatment at 37° C. for an hour with a piperidine concentration of 100 mM.

The various methods of removal of the anti-codon from the template can be used in the selectively degradation of anti-codons. The advantage of selective degradation is especially apparent when the nascent template-directed molecule as well as the building block is encoded for by the template. In one aspect, a scaffold is coded for by the template and building blocks are sequentially incorporated. By using any of the above methods it is possible selectively to remove the building block, including the anti-codon and the linker, while the anti-codon used for recognising the codon which codes for a scaffold remains attached to the template.

Templated Molecule

When a strategy is followed wherein the eventually produced templated molecule is attached to a template via a complementing element, which may and may not involve an anti-codon, the affinity is relatively weak because only hydrogen bondings and hydrophobic interactions tight the parts together. Therefore, in an aspect of the invention, the complementing element finally harbouring the templated molecule, may be attached to the template through a complementing element:template hybrid having a higher annealing temperature than the other codon:anti-codon hybrids of the template. Alternatively, and in some applications preferably, the templated molecule is connected with the template which directed the syntheses thereof via a covalent link. The covalent link may be in addition to the hydrogen bondings or the covalent link may be a substitution. The presence of a covalent link allows for a more harsh chemical treatment of the complex. In one aspect of the invention, the covalent link is selectively cleavable to provide for a separation of the templated molecule from the complementary template.

The method according to the invention may, as a further step, involve the transfer of the templated molecule to an anchorage point on the template, or a sequence complementing the template, to establish an effective chemical connection between the template and the templated molecule. An effective coupling of the templated molecule to the template or a sequence complementary to the template can be desirable to allow for denaturing enrichment conditions or denaturing post-templating modification of the manufactured molecule. The anchorage may involve the presence of a reactive group on the templated molecule and a reaction partner on the template, whereby the reaction between these reactive groups will establish a covalent link. Alternatively, the anchorage point may be present on a complementary sequence hybridised to the template. In a preferred embodiment the complementing sequence has a higher annealing temperature than one or more of the building blocks, notably the terminal building block, to enable usage of a higher stringency during enrichment and, optionally, clearance of used building blocks.

Library

The present invention also relates to a library of bifunctional complexes. The library is composed of a plurality of different complexes, such as at least $10^3$, $10^6$, $10^9$, $10^{12}$, or $10^{15}$ different complexes. The plurality of different complexes is produced by initially providing a plurality of different templates as well as a plurality of building blocks. Each of the anti-codons of the building blocks is adapted so as to be capable of interacting with at least one codon of at least one template. The plurality of different templates is simultaneously subjected to the method described herein above. The propagation part of the method may be repeated a desired number of times to evolve the templated molecule. Each repetition of the propagation is initiated by contacting the templates with a new subset of further building blocks.

The various different templates of the present invention are conveniently constructed to follow a general scheme. According to the scheme, a number of coding sections are provided on the template. In turn, each of the coding sections specifies one or more unique codons. Thus, a specific template comprises a given number of unique codons. The plurality of templates can, taken as a whole, be characterized as a library comprising the total amount of the different combinations of unique codons possible, or any subset thereof. The coding sections are suitable positioned in a linear sequence, such that the individual coding sections are positioned immediately next to each other, optionally, interspaced by a spacer sequence. In some embodiments, it may be of advantage to use a branched template to ensure proximity of reactive groups, the introduction of catalysts in the vicinity of the reactive groups or the introduction of as third reactant.

The unique codons of the templates are preferably composed of a sequence of nucleic acid monomers, such as nucleotides. Each codon is preferably unique in the sense that within the same coding section no other codons have an identical sequence and length of nucleic acid monomers.

Preferably, a unique codon does not have a corresponding sequence anywhere in the plurality of templates. To avoid hybridisation between individual templates it is also desirable to design each of the unique codons such that the complementary sequence thereof does not exist on any other templates.

The number of coding sections may be selected in accordance with inter alia the number of the desired final templated compounds, the building blocks available and the envisaged structure of the templated compound. According to the invention the number of coding regions is preferably at least 3 to achieve the desired diversity. The upper limit for the number of coding regions has not yet been elucidated; however it is believed that a number exceeding 100 may give practical problems. Generally, it is preferred to use templates having between 2 and 50 coding regions, more preferably between 3 and 30 and still more preferred between 4 and 15.

Within each of the coding regions the number of unique codons may be selected according to the need for diversity. The number of unique codons in each of the coding regions may be similar or different. The number of unique codons can be as low as one. This may be the choice when a specific molecular entity is wanted in the evolving templated molecule. The upper limit for the number of unique codons may be chosen quit high as long as specific hybridisation of oligonucleotides of the anti-codons to their complements on the templates occurs. An example of an upper limit may be 10,000, but may be chosen below this limit or above according to the need.

As an example of a relatively small library, around $10^6$ different complexes can be obtained for templates having 4 coding regions, wherein each coding region specifies 30 unique codons. If each of the unique codons only can be present once on the template, at least 120 different building blocks have to be provided. The plurality of templates and the building blocks may be used for the generation of a 4-mer compound, such as an alpha or beta peptide. A larger library of $10^{10}$ complexes may be prepared starting from templates having 5 coding regions and 100 unique codons within each coding region.

The library may be used for a variety of applications, including the search for compounds for use in therapeutic or diagnostic methods and plant protection compounds, like pesticides, fungicides etc. The library may comprise any number of complexes according to the invention.

One method to identify the most active compounds which can be used in e.g. therapeutic applications is to subject the library to an enrichment treatment. According to one aspect of the invention an enrichment of a library of complexes comprising templated molecules with respect to a predetermined activity, comprises the steps of:

i) establishing a first library of complexes comprising templated molecules, said library being obtainable according to any of the methods of the invention,
ii) exposing the library to conditions enriching the library with complexes having the predetermined activity,
iii) amplifying the complexes of the enriched library,
iv) optionally, repeating step ii) to iii), and
v) obtaining an enriched library having a higher ratio of complexes comprising templated molecules with the predetermined activity.

The amplification step is normally preferred, though not always necessary. Especially, when several cycles of enrichments are conducted it is of advantage to make an amplification to obtain sufficient complexes. In a preferred aspect of the invention, the amplification of the complexes of the enriched library comprises the steps of contacting the library of complexes with amplification means, amplifying the templates or the complementing templates, and conducting the method according to the invention using the amplification product as templates. The amplification means can be any of the nucleic acid amplification means suitable for the amplification of the template, such as PCR. Preferably, the amplification of the complex comprises a $10^1$ to $10^{15}$-fold amplification.

To allow for multiple enrichment cycles the steps ii) and iii) are repeated at least 2, 3, 5 times, such as at least 10 times, such as at least 15 times. The complexes may be identified after the completion of each cycle or may be only be identified after the last cycle. There is no explicit need for intermediate identifications as the amplification can be performed without knowing the sequence of the template or a sequence complementing the template, if the template or the complement thereof is provided with suitable primer regions. The identification after the enrichment process involves the determination of the sequence of the template and/or the structural determination of the templated molecule and/or the entire complex having the predetermined activity.

Preferably, the conditions enriching the library comprise contacting a binding partner to the templated molecules of interest. The binding partner may be in solution or may be directly or indirectly immobilised on a support. The enrichment is in general performed using an affinity or activity assay. In one aspect of the invention, the enrichment is conducted by screening for complexes having an affinity for—or an effect on—a target molecule or a target entity. In another aspect the enrichment is conducted by selection for catalytic activity. Alternatively, the conditions enriching the library involve any one or more of electrophoretic separation, gelfiltration, immunoprecipitation, isoelectric focusing, centrifugation, and immobilization.

The enrichment process can involve cells. Thus, in one embodiment, the conditions enriching the library comprise providing cells capable of internalising the templated molecule, or performing an interaction with the templated molecule having the desired predetermined activity.

When the library of complexes have been enriched to a small pool comprising complexes displaying a predetermined activity, it is desirable to obtain each of the complexes separately. The templated molecule can be obtained from the complex by cleaving the linker(s) of the one or more building blocks to release the templated molecule from the template.

Nucleotides

The nucleotides used in the present invention may be linked together in an oligonucleotide. Each nucleotide monomer is normally composed of two parts, namely a nucleobase moiety, and a backbone. The back bone may in some cases be subdivided into a sugar moiety and a inter-nucleoside linker.

The nucleobase moiety may be selected among naturally occurring nucleobases as well as non-naturally occurring nucleobases. It should be clear to the person skilled in the art that various nucleobases which previously have been considered "nonnaturally occurring" have subsequently been found in nature. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown below:

Natural Base Pairs

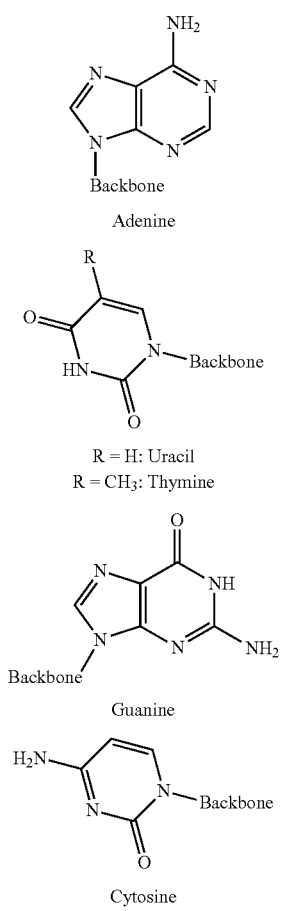

Synthetic Base Pairs

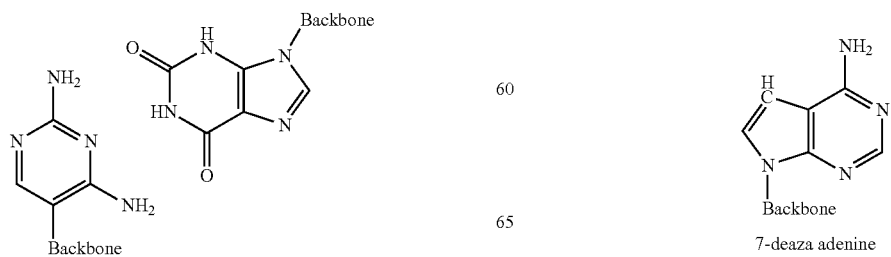

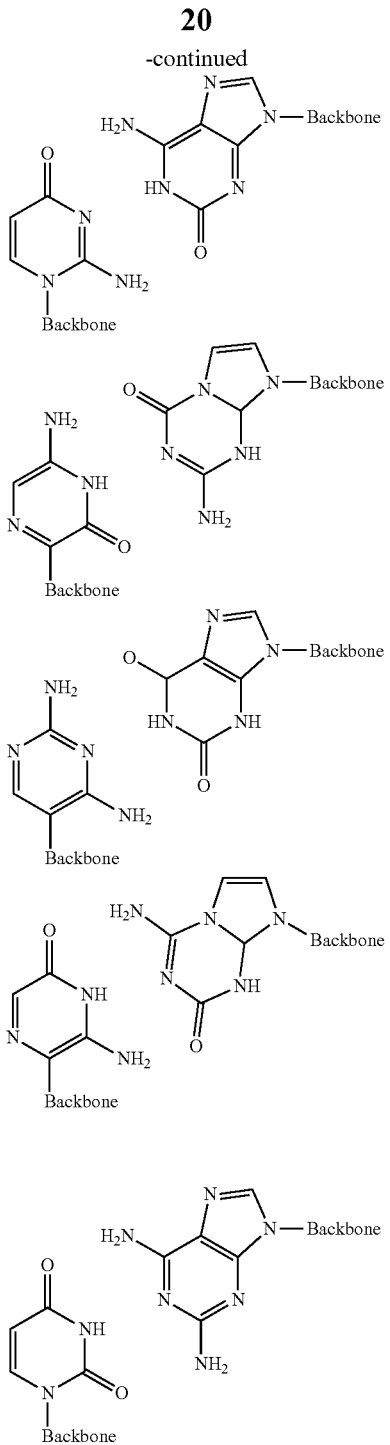

Synthetic Purine Bases 7-deaza adenine

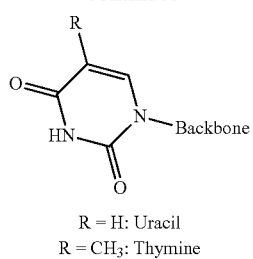
R = H: Uracil
R = CH₃: Thymine
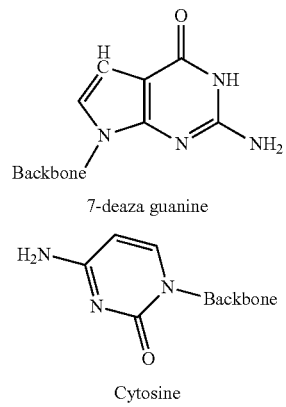
7-deaza guanine
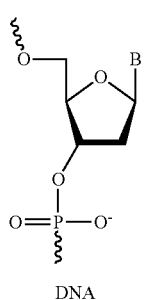
Cytosine
Suitable examples of backbone units are shown below (B denotes a nucleobase):
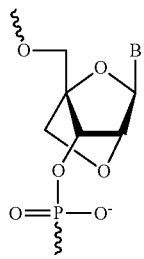
DNA
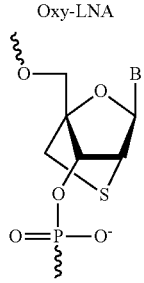
Oxy-LNA
Thio-LNA
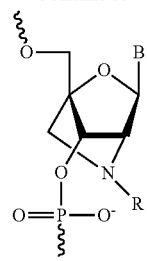
Amino-LNA
R = -H, -CH₃
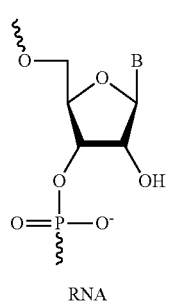
RNA
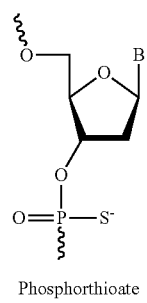
Phosphorthioate
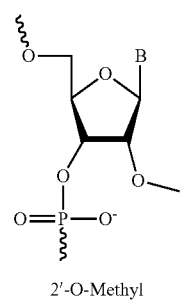
2′-O-Methyl
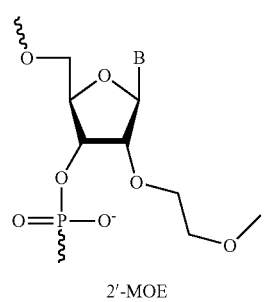
2′-MOE

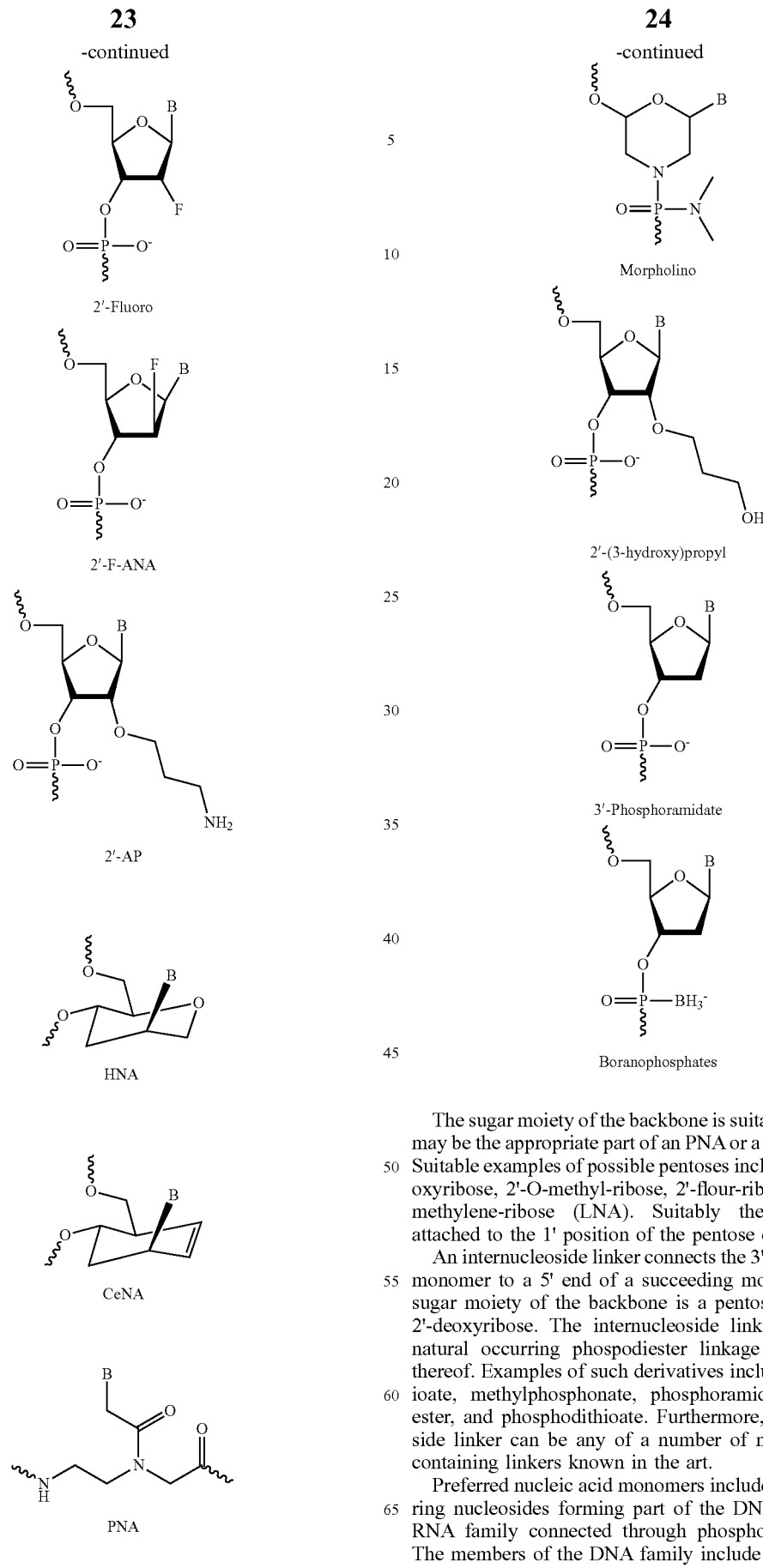

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose of 2'-deoxyribose. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base as discussed above because inosine can pair nearly isoenergetically with A, T, and C.

Each codon is complemented by an anti-codon. The anticodon has the ability specifically to engage with the codon which it complements. The affinity between the codon and the complementing anti-codon is affected through hydrogen bondings following the well-known Watson-Crick base pairing system. Thus, the anti-codon may be composed of the same kind of nucleic acid monomers as the codon itself.

Functional Groups

The functional entity may comprise one or more functional groups, i.e. groups which eventually form part of the templated molecule. The templated molecule may comprise one or more of the following functional groups either alone or in combination:

1. Hydroxyls
2. Primary, secondary, tertiary amines
3. Carboxylic acids
4. Phosphates, phosphonates
5. Sulfonates, sulfonamides
6. Amides
7. Carbamates
8. Carbonates
9. Ureas
10. Alkanes, Alkenes, Alkynes
11. Anhydrides
12. Ketones
13. Aldehydes
14. Nitatrates, nitrites
15. Imines
16. Phenyl and other aromatic groups
17. Pyridines, pyrimidines, purines, indole, imidazole, and heterocyclic bases
18. Heterocycles
19. polycycles
20. Flavins
21. Halides
22. Metals
23. Chelates
24. Mechanism based inhibitors
25. Small molecule catalysts
26. Dextrins, saccharides
27. Fluorescein, Rhodamine and other fluorophores
28. Polyketides, peptides, various polymers
29. Enzymes and ribozymes and other biological catalysts
30. Functional groups for post-polymerization/post activation coupling of functional groups
31. Drugs, e.g., taxol moiety, acyclovir moiety, "natural products"
32. Supramolecular structures, e.g. nanoclusters
33. Lipids
34. Oligonucleotides, oligonucleotide analogs (e.g., PNA, LNA, morpholinos)
35. Hydrogen Reactive Groups Reactive groups relates among other things to groups which form part of the functional entity and are capable of participating in a reaction that forms a connection, either directly or via a suitable bridging molecular entity. Examples of reactive groups are listed below:

1. N-carboxyanhydrides (NCA)
2. N-thiocarboxyanhydrides (NTA)
3. Amines
4. Carboxylic acids
5. Ketones
6. Aldehydes
7. Hydroxyls
8. Thiols
9. Esters
10. Thioesters
11. conjugated system of double bonds
12. Alkyl halides
13. Hydrazines
14. N-hydroxysuccinimide esters
15. Epoxides
16. Haloacetyls
17. UDP-activated saccharides
18. Sulfides
19. Cyanates
20. Carbonylimidazole
21. Thiazinanones
22. Phosphines
23. Hydroxylamines
24. Sulfonates
25. Activated nucleotides
26. Vinylchloride
27. Alkenes, quinines Templated Molecules According to the present invention, virtually any molecule may be templated using the general method disclosed herein. Examples of compounds which can be synthesised include, but are not limited to, the compounds listed below: alpha-, beta-, gamma-, and omega-peptides; mono-, di- and tri-substituted peptides; L- and D-form peptides; Cyclohexane- and cyclopentane-backbone modified betapeptides; Vinylogous polypeptides; glycopolypeptides; polyamides; vinylogous sulfonamide peptide; polysulfonamide; conjugated peptide (i.e., having prosthetic groups); polyesters; polysaccharides; polycarbamates; polycarbonates; polyureas; poly-peptidylphosphonates; azatides; peptoids (oligo N-substituted glycines); polyethers; ethoxyformacetal oligomers; poly-thioethers; polyethylene glycols (PEG); polyethylenes; polydisulfides; polyarylene sulfides; polynucleotides; PNAs; LNAs; morpholinos; oligo pyrrolinone; polyoximes; polyimines; polyethyleneimine; polyacetates; polystyrenes; polyacetylene; polyvinyl; lipids; phospholipids; glycolipids; polycycles (aliphatic); polycycles (aromatic); polyheterocycles; proteoglycan; polysiloxanes; polyisocyanides; polyisocyanates; polymethacrylates; monofunctional, Difunctional, Trifunctional and Oligofunctional open-chain hydrocarbons; monofunctional, difunctional, trifunctional and oligofunctional nonaromatic carbocycles; monocyclic, bicyclic, tricyclic and polycyclic hydrocarbons; bridged polycyclic hydrocarbons; monofunctional, difunctional, trifunctional, and oligofunctional nonaromatic heterocycles; monocyclic, bicyclic, tricyclic, and polycyclic heterocycles, bridged polycyclic heterocycles; monofunctional, difunctional, trifunctional and oligofunctional aromatic carbocycles; monocyclic, bicyclic, tricyclic, and polycyclic aromatic carbocycles; monofunctional, difunctional, trifunctional and oligofunctional aromatic heterocycles; monocyclic, bicyclic, tricyclic and polycyclic heterocycles; chelates; fullerenes; steroids; cyclosporin analogs; as well as any combination of the above molecular moieties.

Enrichment

Selection or screening, commonly referred to as enrichment, of the library of complexes comprising templated molecules with respect to desired activities (for example binding to particular target, catalytic activity, or a particular effect in an activity assay) may be performed according to any standard protocol. For example, affinity selections may be performed according to the principles used for phage displayed, polysome-displayed or mRNA-protein fusion displayed peptides. Selection for catalytic activity may be performed by affinity selections on transition-state analogue affinity columns (Baca et al., Proc. Natl. Acad. Sci USA. 1997; 94(19):10063-8), or by function-based selection schemes (Pedersen et al., Proc. Natl. Acad. Sci. USA. 1998, 95(18):10523-8). Screening for a desired characteristic may be performed according to standard microtiter plate-based assays, or by FACS-sorting assays.

Generally, affinity selections involve the immobilisation of a target or a binding partner on a solid support, such as a column. Subsequently, the complex manufactured according to the invention is added to the column under conditions allowing a part of the complexes to bind to the target. The complexes not bound to the target is eluted out of the column and discharged. The part of the complexes attached to the target may be amplified using the template associated with the templated molecule.

The choice of amplification method depends on the choice of codons and anti-codons. Natural oligonucleotides can be amplified by any state of the art method. These methods include, but is not limited to the polymerase chain reaction (PCR); as wells as e.g. nucleic acid sequence-based amplification (e.g. Compton, Nature 350, 91-92 (1991)), amplified anti-sense RNA (e.g. van Gelder et al., PNAS 85: 77652-77656 (1988)); self-sustained sequence replication system (e.g. Gnatelli et al., PNAS 87: 1874-1878 (1990)); polymerase independent amplification as described in e.g. Schmidt et al., NAR 25: 4797-4802 (1997), as well as in vivo amplification of plasmids carrying cloned DNA fragments. Ligase-mediated amplification methods may also be used, e.g., LCR (Ligase Chain Reaction).

For non-natural nucleotides the choices of efficient amplification procedures are fewer. As non-natural nucleotides per definition can be incorporated by certain enzymes including polymerases, it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al., NAR 25: 4797-4802 (1997)). For backbone-modified oligonucleotide analogs such as PNA and LNA, this amplification method may be used. Before or during amplification the templates or complementing templates may be mutagenized or recombined in order to create a larger diversity for the next round of selection or screening.

Following the amplification of the template part of the complex, the method according to the invention is conducted using the amplification product as the templates. The result is a reduced or enriched library of complexes of a template attached to a template molecule.

The selection and amplification steps may be repeated if considered necessary to further enrich the library. When the selection and amplification steps are repeated, the binding step involving the target and the complexes, is preferably performed under more strict conditions ensuring that only a part of the complexes adhere to the target.

The enrichment cycles may be performed 2 to 15 times or even more with enrichment in each cycle of 10 to 1000 times. In one approach, the starting library amounts to $10^{14}$ complexes. After seven cycles of enrichments with a 100 fold concentration in each cycle, the complex with the highest affinity to the target should, theoretically, be obtained. However, it is more likely that the final cycles deliver a small pool of interesting complexes, which have to be examined by other means.

After the final round of selection, it is often desirable to sequence individual templates, in order to determine the composition of individual templated molecules. If the template contains natural nucleotides, it is a standard routine to optionally PCR amplify the isolated templates (if the template is an RNA molecule, it is necessary to use reverse transcriptase to produce cDNA prior to the PCR-amplification), and then clone the DNA fragments into for example plasmids, transform these and then sequence individual plasmid-clones containing one or multiple tandem DNA sequences. In this case, it is practical to design a restriction site in both of the flanking sequences to the central coding sequence of the template (i.e., in the primer binding sites). This will allow easy cloning of the isolated nucleotides. Sequencing can be done by the standard dideoxy chain termination method, or by more classical means such as Maxam-Gilbert sequencing.

If the template contains non-natural nucleotides, it may not be feasible to clone individual sequences by transfer through a microbial host. However, using bead populations where each bead carries one oligonucleotide sequence, it is possible to clone in vitro, where after all the nucleotides attached to a specific bead may be optionally amplified and then sequenced (Brenner et al., 2000, Proc. Natl. Acad. Sci. USA 97, 1665-1670). Alternatively, one may dilute the population of isolates adequately, and then aliquot into microtiter plates so that the wells on average contain for example 0.1 templates. By amplifying the single templates by for example PCR, it will now be possible to sequence using standard methods. Of course, this requires that the non-natural nucleotides are substrates for the thermostable polymerase used in the PCR.

If alternative methods are used that require shorter oligonucleotides it may be desirable to design the starting template so as to contain restriction sites on either side of the encoding/templating region of the template. Thereby, after the final selection round, the templates can be restricted, to obtain a short oligonucleotide encoding the templated molecule, and then these short oligonucleotides can be applied to various analytical procedures.

It is also possible to sequence the isolates by the use of a DNA array of oligonucleotides with random but predetermined sequences.

It may also be desirable to sequence the population of isolates as a pool, for example if the sequences are expected to be in register, for example because the initial library consisted of a degenerate sequence based on a polymer sequence with a known (relatively high) desired activity. Therefore, it is then expected that all the isolates have sequences similar to the initial sequence of the templates before selection. Thus, the population of isolates can be sequenced as a whole, to obtain a consensus sequence for the population as a whole.

The present invention is also directed to approaches that allow selection of small molecules capable of binding to different targets. The template-displaying molecule technology contains a built-in function for direct selection and amplification. The binding of the selected molecule should be selective in that they only coordinate to a specific target and thereby prevent or induce a specific biological effect. Ultimately, these binding molecules should be possible to use e.g. as therapeutic agents, or as diagnostic agents.

Template-displaying molecule libraries can easily be combined with screenings, selections, or assays to assess the effect of binding of a molecule ligand on the function of the target. In a more specific embodiment, the template-displaying method provides a rapid means for isolating and identifying molecule ligands which bind to supra-molecular, macro-supra-molecular, macro-molecular and low-molecular structures (e.g. nucleic acids and proteins, including enzymes, receptors, antibodies, and glycoproteins); signal molecules (e.g. cAMP, inositol triphosphate, peptides, prostaglandins); and surfaces (e.g. metal, plastic, composite, glass, ceramics, rubber, skin, tissue).

Specifically, selection or partitioning in this context means any process whereby the template-displaying molecule complex bound to a target molecule, i.e. the complex-target pair, can be separated from template-displaying molecules not bound to the target molecule. Selection can be accomplished by various methods known in the art.

The selection strategy can be carried out so it allows selection against almost any target. Importantly, no steps in this selection strategy need any detailed structural information of the target or the molecules in the libraries. The entire process is driven by the binding affinity involved in the specific recognition/coordination of the molecules in the library to a given target. However, in some applications, if needed, functionality can also be included analogous to selection for catalytic activity using phage display (Soumillion et al. (1994) J. Mol. Biol. 237: 415-22; Pedersen et al. (1998) PNAS. 18: 10523-10528). Example of various selection procedures are described below.

This built-in template-displaying molecule selection process is well suited for optimizations, where the selection steps are made in series starting with the selection of binding molecules and ends with the optimized binding molecule. The single procedures in each step are possible to automate using various robotic systems. This is because there is a sequential flow of events and where each event can be performed separately. In a most preferable setting, a suitable template-displaying molecule library and the target molecule are supplied to a fully automatic system which finally generates the optimized binding molecule. Even more preferably, this process should run without any need of external work outside the robotic system during the entire procedure.

The libraries of template-displayed molecules will contain molecules that could potentially coordinate to any known or unknown target. The region of binding on a target could be into a catalytic site of an enzyme, a binding pocket on a receptor (e.g. GPCR), a protein surface area involved in protein-protein interaction (especially a hot-spot region), and a specific site on DNA (e.g. the major groove). The template-displaying molecule technology will primarily identify molecules that coordinate to the target molecule. The natural function of the target could either be stimulated (agonized) or reduced (antagonized) or be unaffected by the binding of the template-displaying molecules. This will be dependent on the precise binding mode and the particular binding-site the template-displaying molecules occupy on the target.

However, it is known that functional sites (e.g. protein-protein interaction or catalytic sites) on different proteins are more prone to bind molecules that other more neutral surface areas on a protein. In addition, these functional sites normally contain a smaller region that seems to be primarily responsible for the binding energy, the so called hot-spot regions (Wells, et al. (1993) Recent Prog. Hormone Res. 48; 253-262). This phenomenon will increase the possibility to directly select for small molecules that will affect the biological function of a certain target.

The template-displaying molecule technology of the invention will permit selection procedures analogous to other display methods such as phage display (Smith (1985) Science 228: 1315-1317). Phage display selection has been used successfully on peptides (Wells & Lowman. (1992) Curr. Op. Struct. Biol. 2, 597-604) proteins (Marks et al. (1992) J. Biol. Chem. 267: 16007-16010) and antibodies (Winter et al. (1994) Annu. Rev. Immunol. 12: 433-455). Similar selection procedures are also exploited for other types of display systems such as ribosome display (Mattheakis et al. (1994) Proc. Natl. Acad. Sci. 91: 9022-9026) and mRNA display (Roberts, et al. (1997) Proc. Natl. Acad. Sci. 94: 12297-302).

The linkage between the templated molecule (displayed molecule) and DNA replication unit (coding template) allows an identification of binding molecules using various selection strategies. This invention allows a broad strategy in identifying binding molecules against essentially any known target. In addition, this technology will also allow discovery of novel unknown targets by isolating binding molecules against unknown antigens (epitopes) and use these binding molecules for identification and validation.

Figure 12:
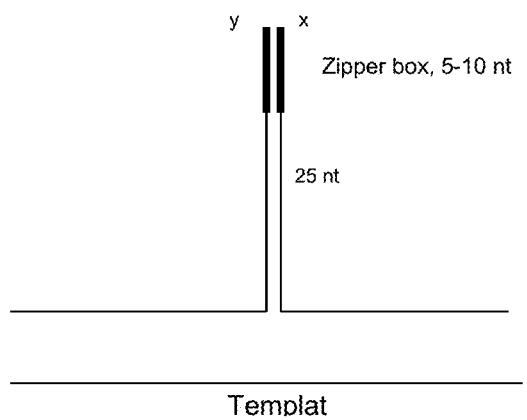
FIG. 12 shows a schematic drawing of the general principle used in the experiments.

As will be understood, selection of binding molecules from the template-displaying molecule libraries can be performed in any format to identify optimal binding molecules. A typical selection procedure against a purified target will include the following major steps: Generation of a template-displaying molecule library: Immobilization of the target molecule using a suitable immobilization approach; Adding the library to allow binding of the template-displayed molecules; Removing of the non-binding template-displayed molecules; Elution of the template-displayed molecules bound to the immobilized target; Amplification of enriched template-displaying molecules for identification by sequencing or to input for the next round of selection. The general steps are schematically shown in FIG. 12.

In a preferred embodiment, a standard selection protocol using a template-displaying molecule library is to use the bio-panning method. In this technique, the target (e.g. protein or peptide conjugate) is immobilized onto a solid support and the template-displayed molecules that potentially coordinate to the target are the ones that are selected and enriched. However, the selection procedure requires that the bound template-displayed molecules can be separated from the unbound ones, i.e. those in solution. There are many ways in which this might be accomplished as known to ordinary skilled in the art.

The first step in the affinity enrichment cycle is when the template-displayed molecules showing low affinity for an immobilized target are washed away, leaving the strongly binding template-displayed molecules attached to the target. The enriched population, remaining bound to the target after the stringent washing, is then eluted with, e.g. acid, chaotropic salts, heat, competitive elution with the known ligand or proteolytic release of the target/template molecules. The eluted template-displayed molecules are suitable for PCR, leading to many orders of amplification, i.e. every single template-displayed molecule enriched in the first selection round participates in the further rounds of selection at a greatly increased copy number. After typically three to ten rounds of enrichment a population of molecules is obtained which is greatly enriched for the template-displayed molecules which bind most strongly to the target. This is followed quantitatively by assaying the proportion of template-displaying molecules which remain bound to the immobilized target. The variant template sequences are then individually sequenced.

Immobilisation of the target (peptide, protein, DNA or other antigen) on beads might be useful where there is doubt that the target will adsorb to the tube (e.g. unfolded targets eluted from SDS-PAGE gels). The derivatised beads can then be used to select from the template-displaying molecules, simply by sedimenting the beads in a bench centrifuge. Alternatively, the beads can be used to make an affinity column and the template-displaying libraries suspension recirculated through the column. There are many reactive matrices available for immobilizing the target molecule, including for instance attachment to —$NH_2$ groups and —SH groups. Magnetic beads are essentially a variant on the above; the target is attached to magnetic beads which are then used in the selection. Activated beads are available with attachment sites for —$NH_2$ or —COOH groups (which can be used for coupling). The target can be also be blotted onto nitrocellulose or PVDF. When using a blotting strategy, it is important to make sure the strip of blot used is blocked after immobilization of the target (e.g. with BSA or similar protein).

In another preferred embodiment, the selection or partitioning can also be performed using for example: Immunoprecipitation or indirect immunoprecipitation were the target molecule is captured together with template-displaying binding molecules; affinity column chromatography were the target is immobilized on a column and the template-displaying libraries are flowed through to capture target-binding molecules; gel-shift (agarose or polyacrylamide) were the selected template-displaying molecules migrate together with the target in the gel; FACS sorting to localize cells that coordinates template-displaying molecules; CsCl gradient centrifugation to isolate the target molecule together template-displaying binding molecules; Mass spectroscopy to identify target molecules which are labelled with template-displaying molecules; etc., without limitation. In general, any method where the template-displaying molecule/target complex can be separated from template-displaying molecules not bound to the target is useful.

TABLE 1

Examples of selection method possible to use to identify binding molecules using the template-displaying technology.

| Type of Target | Method of choice |
| --- | --- |
| Soluble receptors | Direct immobilization, Immunoprecipitation, affinity column, FACS sorting, MS. |
| Cell surface receptor | Cell-surface subtraction selection, FACS sorting, Affinity column. |
| Enzyme inhibitors | Direct immobilization, Immunoprecipitation, affinity column, FACS sorting, MS. |
| Surface epitopes | Cell-surface subtraction selection, in-vivo selection, FACS sorting, Affinity column. |

Elution of template-displayed molecules can be performed in different ways. The binding molecules can be released from the target molecule by denaturation, acid, or chaotropic salts and then transferred to another vial for amplification. Alternatively, the elution can be more specific to reduce the background. Elution can be accomplished using proteolysis to cleave a linker between the target and the immobilizing surface or between the displaying molecule and the template. Also, elution can be accomplished by competition with a known ligand. Alternatively, the PCR reaction can be performed directly in the washed wells at the end of the selection reaction.

A possible feature of the invention is the fact that the binding molecules need not be elutable from the target to be selectable since only the encoding template DNA is needed for further amplification or cloning, not the binding molecule itself. It is known that some selection procedure can bind the most avid ligands so tightly as to be very difficult to elute. However the method of the invention can successfully be practiced to yield avid ligands, even covalent binding ligands.

Alternative selection protocol includes a known ligand as fragment of each displayed molecule in the library. That known ligand will guide the selection by coordinate to a defined part on the target molecule and focus the selection to molecules that binds to the same region. This could be especially useful for increasing the affinity for a ligand with a desired biological function but with a too low potency.

A further aspect of the present invention relates to methods of increasing the diversity or complexity of a single or a mixture of selected binding molecules. After the initial selection, the enriched molecules can be altered to further increase the chemical diversity or complexity of the displayed molecules. This can be performed using various methods known to the art. For example, using synthesized randomized oligonucleotides, spiked oligonucleotides or random mutagenesis. The randomization can be focused to allow preferable codons or localized to a predetermined portion or sub-sequence of the template nucleotide sequence. Other preferable method is to recombine templates coding for the binding molecules in a similar manner as DNA shuffling is used on homologous genes for proteins (Stemmer (1994) Nature 370:389-91). This approach can be used to recombine initial libraries or more preferably to recombine enriched encoding templates.

In another embodiment of the invention when binding molecules against specific antigens that is only possible to express on a cell surface, e.g. ion channels or transmembrane receptors, is required, the cells particle themselves can be used as the selection agent. In this sort of approach, cells lacking the specific target should be used to do one or more rounds of negative selection or be present in large excess in the selection process. Here, irrelevant template-displayed molecules are removed. For example, for a positive selection against a receptor expressed on whole cells, the negative selection would be against the untransformed cells. This approach is also called subtraction selection and has successfully been used for phage display on antibody libraries (Hoogenboom et al. (1998) Immunotech. 4: 1-20).

A specific example of a selection procedure can involve selection against cell surface receptors that become internalized from the membrane so that the receptor together with the selected binding molecule can make its way into the cell cytoplasm or cell nucleus. Depending on the dissociation rate constant for specific selected binding molecules, these molecules largely reside after uptake in either the cytoplasm or the nucleus.

The skilled person in the art will acknowledge that the selection process can be performed in any setup where the target is used as the bait onto which the template-displaying molecules can coordinate.

The selection methods of the present invention can be combined with secondary selection or screening to identify molecule ligands capable of modifying target molecule function upon binding. Thus, the methods described herein can be employed to isolate or produce binding molecules which bind to and modify the function of any protein or nucleic acid. It is contemplated that the method of the present invention can be employed to identify, isolate or produce binding molecules which will affect catalytic activity of target enzymes, i.e., inhibit catalysis or modifying substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

A still further aspect of the present invention relates to methods allowing functionality in the selection process can also be included. For example, when enrichment against a certain target have been performed generation a number of different hits, these hits can then directly be tested for functionality (e.g. cell signalling). This can for example be performed using fluorescence-activated cell sorting (FACS).

The altered phenotype may be detected in a wide variety of ways. Generally, the changed phenotype is detected using, for example: microscopic analysis of cell morphology; standard cell viability assays, including both increased cell death and increased cell viability; standard labelling assays such as fluorometric indicator assays for the presence of level of particular cell or molecule, including FACS or other dye staining techniques; biochemical detection of the expression of target compounds after killing the cells; etc. In some cases, specific signalling pathways can be probed using various reporter gene constructs.

Secondary selection methods that can be combined with template-displaying molecule technology include among others selections or screens for enzyme inhibition, alteration or substrate binding, loss of functionality, disruption of structure, etc. Those of ordinary skill in the art are able to select among various alternatives of selection or screening methods that are compatible with the methods described herein.

The binding molecules of the invention can be selected for other properties in addition to binding. For example, during selection; stability to certain conditions of the desired working environment of the end product can be included as a selection criterion. If binding molecules which are stable in the presence of a certain protease is desired, that protease can be part of the buffer medium used during selection. Similarly, the selection can also be performed in serum or cell extracts or any type of media. As will be understood, when utilizing this template-displaying approach, conditions which disrupt or degrade the template should be avoided to allow amplification. Other desired properties can be incorporated, directly into the displaying molecules as will be understood by those skilled in the art. For example, membrane affinity can be included as a property by employing building blocks with high hydrophobicity.

Molecules selected by the template-displaying molecule technology can be produced by various synthetic methods. Chemical synthesis can be accomplished since the structure of selected binding molecules is readily obtained form the nucleic acid sequence of the coding template. Chemical synthesis of the selected molecules is also possible because the building blocks that compose the binding molecules are also known in addition to the chemical reactions that assemble them together.

In a preferred embodiment, the selected binding molecules is synthesized and tested in various appropriate in vitro and in vivo testing to verify the selected candidates for biological effects and potency. This may be done in a variety of ways, as will be appreciated by those in the art, and may depend on the composition of the bioactive molecule.

Target Identification and Validation

In another aspect, the present invention provides methods to identify or isolate targets that are involved in pathological processes or other biological events. In this aspect, the target molecules are again preferably proteins or nucleic acids, but can also include, among others, carbohydrates and various molecules to which specific molecule ligand binding can be achieved. In principal, the template-displaying molecule technology could be used to select for specific epitopes on antigens found on cells, tissues or in vivo. These epitopes might belong to a target that is involved in important biological events. In addition, these epitopes might also be involved in the biological function of the target.

Phage display with antibodies and peptide libraries has been used numerous times successfully in identifying new cellular antigens. (e.g. Pasqualini et al. (1996) Nature 380: 364-366; Pasqualini et al. (2000) Cancer Res. 60: 722-727; Scheffer et al. (2002) Br J Cancer 86: 954-962; Kupsch et al. (1999) Clin Cancer Res. 5: 925-931; Tseng-Law et al. (1999) Exp. Hematol. 27: 936-945; Gevorkian et al. (1998) Clin. Immunol. Immunopathol. 86: 305-309). Especially effective have been selection directly on cells suspected to express cell-specific antigens. Importantly, when selecting for cell-surface antigen, the template molecule can be maintained outside the cell. This will increase the probability that the template molecule will be intact after release for the cell surface.

In vivo selection of template-displayed molecules has tremendous potential. By selecting from libraries of template-displayed molecules in vivo it is possible to isolate molecules capable of homing specifically to normal tissues and other pathological tissues (e.g. tumours). This principle has been illustrated using phage display of peptide libraries (Pasqualini & Ruoslathi (1996) Nature 280: 364-366). This system has also been used in humans to identify peptide motifs that localized to different organs (Arap et al. (2002) Nat. Med. 2:121-127). A similar selection procedure could be used for the template-displaying libraries. The coding DNA in phage display protected effectively by the phage particle allows selection in vivo. Accordingly, the stability of the template in vivo will be important for amplification and identification. The template can be stabilised using various nucleotide derivatives in a similar way as have been used to stabilise aptamers for in vivo applications (Nolte (1996) Nature Biotechnol. 14: 1116-1121; Pagratis et al. (1997) Nature Biotechnol. 15: 68-72). However, it is reasonable to believe that the template structure will be stabilized against degradation due to the modified bases used for encoding the displayed molecule. Other types of protection are also possible where the template molecule is shielded for the solution using various methods. This could include for example liposomes, pegylation, binding proteins or other sorts of protection. The template molecule could also be integrated into another designed structure that protects the template form external manipulation. Fort example, the linker can be design to be incorporated in vesicles to position the templates inside the vesicle and the displaying molecules on the outside. The arrangement will protect the template molecules from external manipulate and at the same time allow exposure of the displaying molecules to permit selection.

Most antibodies have a large concave binding area which requires to some degree protruding epitopes on the antigens. Also, the antibody molecule is a large macromolecule (150 KDa) which will sterically reduce the access for a number of different antigens (e.g. on a cell surface). The template-displaying technology should be able to access and recognize epitopes inaccessible to antibodies. The small binding molecules will be able to bind into active sites, grooves and other areas on an antigen. The coding template element is also smaller that an antibody which will increase the physical access of the template-binding molecule par. In addition, the diversity and complexity of the template-displaying molecule libraries will be much greater compare to peptide libraries. This will increase the possibility to find molecules that can coordinate to epitopes inaccessible to peptides due to inadequate chemistry. All together, the template-displaying molecule technology has the potential to identify novel antigens which is not possible to identify with antibodies or peptides. One of ordinary skill in the art will acknowledge that various types of cells can be used in the selection procedure. It will also be understood that the selection for new antigens can be performed using subtraction methods as described previously.

Another aspect of the present invention relates to methods to validate the identified target. The identified binding molecules can directly be used if they change the biological response of the target. This can be done either in vitro using any direct or cell-based assay or directly in vivo studying any phenotypic response. The strength of this approach is that the same molecules are used both for identification and validation of various targets. Most favourable, the binding molecules could also directly be used as therapeutic agents.

In another preferred embodiment, the template-displaying molecules are used to pull out the target molecules. This can for instance be achieved by selection against a cDNA library expressed on bacteriophage (libraries vs. libraries). By mixing a template-displaying molecule library with a cDNA library it will be possible to find binding pairs between the small molecules in the template-displaying molecule library and proteins from the cDNA library. One possibility is to mix a phage display library with a template display library and do a selection for either the phage or template library. The selected library is then plated to localized phage clones and the DNA coding for the phage and template displayed molecules can then be identified using PCR. Other types of libraries than cDNA could also be used such as nucleic acids, carbohydrates, synthetic polymer.

In another embodiment of the invention the template-displaying molecule technology can be used to account for in vivo and in vitro drug metabolism. That could include both phase I (activation) and phase II (detoxification) reactions. The major classes of reactions are oxidation, reduction, and hydrolysis. Other enzymes catalyze conjugations. These enzymes could be used as targets in a selection process to eliminate displayed molecule that are prone to coordinate to these enzymes. The templates corresponding to these displayed molecules could subsequently be used to compete or eliminate these molecules when making template-displaying molecule libraries.

These obtained libraries will then be free of molecules that will have a tendency of binding to enzymes involved in phase I-II and possible be faster eliminated. For instance, a selection on each separate enzyme or any combination of cytochrome P450 enzymes, flavin monooxygenase, monoamine oxidase, esterases, amidases, hydrolases, reductases, dehydrogenases, oxidases UDP-glucuronosyltransferases, glutathione S-transferases as well as other relevant enzymes could be performed to identify these binding molecules that are prone to coordinate to these metabolic enzymes. Inhibitors are easily selected for due to their binding affinity but substrates need at least micro molar affinity to be identified.

Another interesting embodiment of this invention is the possibility to directly select for molecules that passively or actively becomes transported across epithelial plasma membrane, or other membranes. One possible selection assay is to use CaCO-2 cells, a human colon epithelial cell line, which is general, accepted as a good model for the epithelial barrier in the gastrointestinal guts. The CaCO-2 assay involves growing a human colon epithelial cell line on tissue culture well inserts, such that the resultant monolayer forms a biological barrier between apical and basolateral compartments. The template-displaying molecule libraries are placed either side of the cell monolayer and the molecules that can permeate the cell monolayer is collected and amplified. This process can be repeated until active molecules have been identified. Other cell line or setup of this assay is possible and is obvious for skill in the art.

A still further aspect of the present invention relates methods of selecting for stability of the selected molecules. This could be performed by subjecting an enriched pool of binding molecules to an environment that will possibly degrade or change the structure of the binding molecules. Various conditions could be certain proteases or a mixture of protease, cell extract, and various fluids from for example the gastrointestinal gut. Other conditions could be various salts or acid milieu or elevated temperature. Another possibility is to generate a library of known ligands and subject that library to stability tests and selection to identify stable molecules under certain conditions as describe above.

Therapeutic Applications

The template-displaying molecule technology of the invention may be used for blocking or stimulating various targets. A therapeutically relevant target is a substance that is known or suspected to be involved in a regulating process that is malfunctioning and thus leads to a disease state. Examples of such processes are receptor-ligand interaction, transcription-DNA interaction, and cell-cell interaction involving adhesion molecules, cofactor-enzyme interaction, and protein-protein interaction in intracellular signalling. Target molecule means any compound of interest for which a molecule ligand is desired. Thus, target can, for example, include a chemical compound, a mixture of chemical compounds, an array of spatially localized compounds, a biological macromolecule, such as DNA or mRNA, a bacteriophage peptide display library, a ribosome peptide display library, an extract made from biological materials such as bacteria, plants, fungi, or animal (e.g. mammalian) cells or tissue, protein, fusion protein, peptide, enzyme, receptor, receptor ligand, hormone, antigen, antibody, drug, dye, growth factor, lipid, substrate, toxin, virus, or the like etc., without limitation. Other examples of targets include, e.g. a whole cell, a whole tissue, a mixture of related or unrelated proteins, a mixture of viruses or bacterial strains or the like. etc., without limitation.

Therapeutic drug targets can be divided into different classes according to function; receptors, enzymes, hormones, transcription factors, ion channels, nuclear receptors, DNA, (Drews, J. (2000) Science 287:1960-1964). Among those, receptors, nuclear receptors, and metabolic enzymes constitute overwhelmingly the majority of known targets for existing drugs. Especially, G Protein-Coupled Receptors (GPCR) constitutes one of the most important classes of drug targets together with proteases for pharmacological intervention. Although the above examples are focused on the most relevant targets, it will be self-evident for a person skilled in the art that any other therapeutic target may be of interest.

The present invention employing the template-displaying molecule technology can be utilized to identify agonists or antagonists for all these classes of drug targets, dependent on the specific properties each target holds. Most of the targets are possible to obtain in a purified form for direct selection procedures. Other targets have to be used when they are in their native environments such as imbedded cell surface receptors. In those situations the selection using the template-displaying molecule libraries can be performed using subtraction-selection described previously.

One specific application of the template-displaying molecule technology of the invention is to generate molecules that can function as antagonists, where the molecules block the interaction between a receptor and one or more ligands. Another application includes cell targeting. For example, the generated molecules recognizing specific surface proteins or receptors will be able to bind to certain cell types. Such molecules may in addition carry another therapeutic agent to increase the potency and reduce the side-effects (for example cancer treatment). Applications involving antiviral agents are also included. For example, a generated molecule, which binds strongly to epitopes on the virus particle, may be useful as an antiviral agent. Another specific application of the template-displaying molecule technology of the invention is to generate molecules that can function as agonists, where the molecules stimulate or activate a receptor to initiate a cellular signalling pathway.

In FIG. 13, a schematic drawing of the use of a dimerisation domain in the synthesis of (A) a scaffolded molecule and (B) a polymeric molecule is showed. When templating a scaffolded molecule (containing in this example four reactive groups of the same kind, Y), it is convenient to use four building blocks with identical zipper boxes ("b"), and one building block (carrying the four reactive groups Y) with a zipper box ("a") that is complementary to ("b"). When templating a polymeric molecule one may alternate between the zipper identity, i.e. first building block carries a zipper box ("a"), second building block in the array carries ("b") that dimerize with ("a"), third building block carries ("a"), etc.

Figure 14:
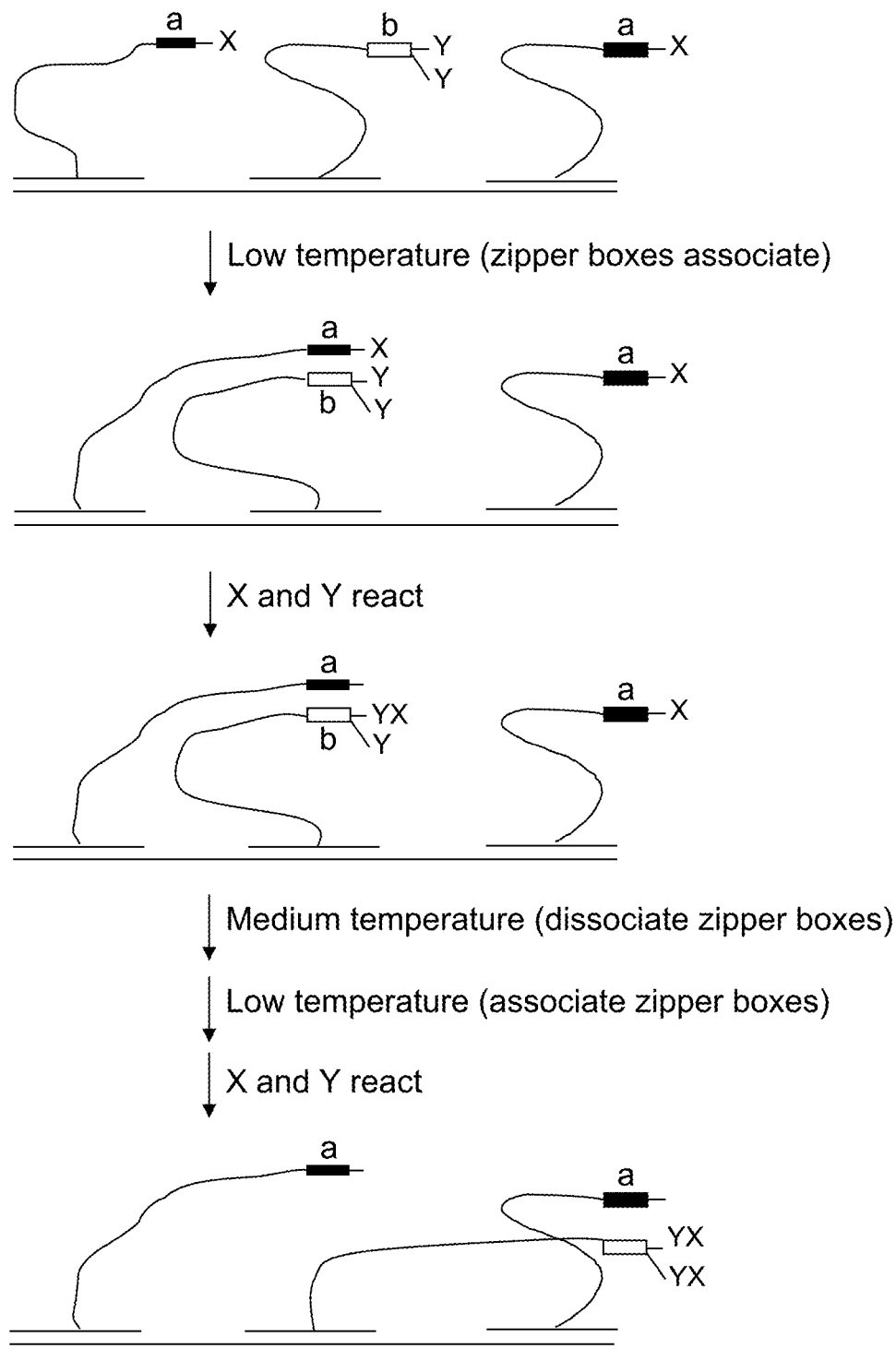
FIG. 14 shows a preferred embodiment of the general principle.

The preferred embodiment shown in FIG. 14 increases the local concentration of the reactive groups X and Y, by bringing X and Y into closer proximity through the dimerization of two zipper boxes. In this example, three building blocks are shown, each carrying a zipper box, two of which having the same sequence ("a") and one is the complementary sequence ("b"). First, the building blocks are annealed to the template at a medium temperature (where the interaction between the zipper boxes is insignificant). Then the temperature is decreased to a lower temperature where two complementary zipper domains ("a" (of the first building block) and "b" (of the second building block)) anneal to each other. This brings X and Y into close proximity, and X and Y may react to form YX. In the example, the reaction between X and Y involves a transfer of X from the first building block to the second building block carrying Y. When the temperature is increased to a medium temperature the zipper box dissociates. When the temperature is then lowered the zipper domain of the second building block may anneal to the zipper box of the third building block (which carries a reactive group X). As a result, this X may now be transferred to the second building block, as a result of the increased proximity and hence increased reactivity between X and Y.

EXAMPLES

General Methods and Materials for Examples 1 to 11

In order to examine the reaction efficiency between two reactive groups, each coupled to a oligonucleotide, when the two oligos are annealed to neighbouring sites on the same template, the general set-up shown immediately below was used. The two oligos contain terminal nucleotides (X, Y, and Z) derivatized with a carboxylic acid or an amine, as described below the figure. After reaction ("cross-linking") of the reactive groups on the termini of the two oligos, the cross-linking efficiency was analyzed by polyacrylamide gel electrophoresis, as the two oligos become coupled as a result of this cross-linking, and therefore migrate slower through the column.

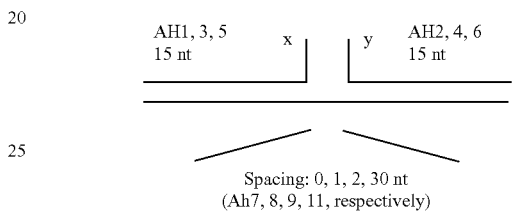

Building Blocks:

| | | |
|---|---|---|
| Ah 1: | 5'-GCTACTCGTACGAGX | (SEQ ID NO: 1) |
| Ah 3: | 5'-GCTACTCGTACGAGY | (SEQ ID NO: 2) |
| Ah 5: | 5'-GCTACTCGTACGAGZ | (SEQ ID NO: 3) |
| Ah 2: | 5'-XCACTTGCAGACAGC | (SEQ ID NO: 4) |
| Ah 4: | 5'-YCACTTGCAGACAGC | (SEQ ID NO: 5) |
| Ah 6: | 5'-ZCACTTGCAGACAGC | (SEQ ID NO: 6) |
| Ah 14: | 5'-GCTACTCGTACGAG | (SEQ ID NO: 7) |
| Ah 23: | 5'-GCTACTGGCATCGGX | (SEQ ID NO: 8) |
| Ah 24: | 5'-GCTACTGGCATCGGY | (SEQ ID NO: 9) |
| Ah 27: | 5'-YCACTTGCAGACAGC | (SEQ ID NO: 10) |

In examples pertaining to a zipper box the following sequences was used

AH36:
(SEQ ID NO: 11)
5'-CGACCTCTGGATTGCATCGGTCATGGCTGACTGTCCGTCGAA-TGT
GTCCAGTTACX

AH37:
(SEQ ID NO: 12)
5'-ZGTAACTGGACTGTAAGCTGCCTGTCAGTCGGTACTGACCT-
GTCGAGCATCCAGCT

AH51:
(SEQ ID NO: 13)
5'-ZGTAACACCTGTGTAAGCTGCCTGTCAGTCGGTACTGACCT-
GTCGAGCATCCAGCT

-continued

AH67:
(SEQ ID NO: 14)
5'-ZCATTGACCTGTGTAAGCTGCCTGTCAGTCGGTACTG-

ACCTGTCGAGCATCCAGCT

AH69:
(SEQ ID NO: 15)
5'-AGZAACACCTGTGTAAGCTGCCTGTCAGTCGGTACTG-

ACCTGTCGAGCATCCAGCT

AH66:
(SEQ ID NO: 16)
5'-ZTTGTAACTGGACTGTAAGCTGCCTGTCAGTCGGTACTGACC-

TGTCGAGCATCCAGCT

AH65:
(SEQ ID NO: 17)
5'-CGACCTCTGGATTGCATCGGTCATGGCTGACTGTCCGTCG-

AATGTGTCCAGTTACTTX

Zipper box sequences are underlined.
X=Carboxy-dT
Y=Amino-Modifier C2 dT
Z=Amino-Modifier C6 dT

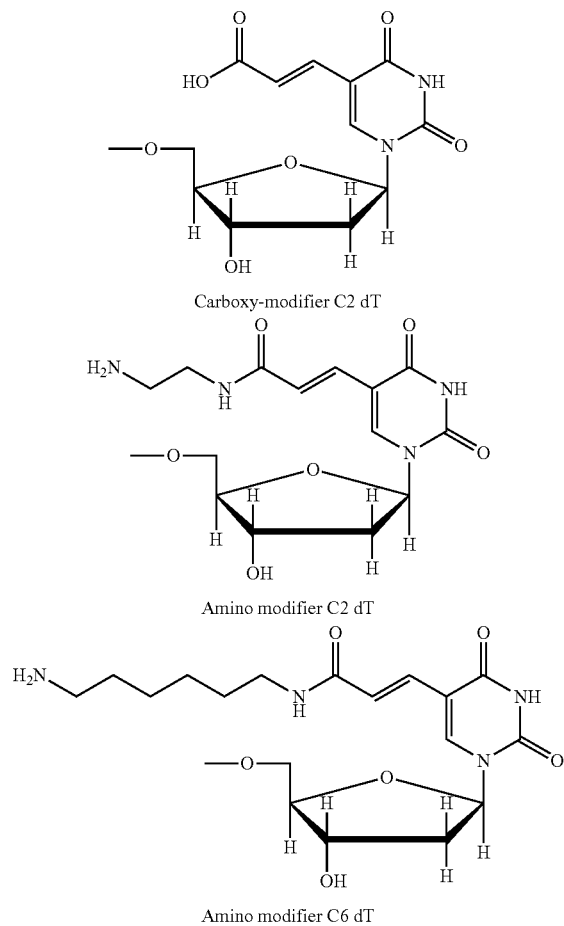

Carboxy-modifier C2 dT

Amino modifier C2 dT

Amino modifier C6 dT

The oligonucleotides were prepared following the conventional phosphoamidite approach. X was incorporated using the commercially available carboxy-dT phosphoramidite (10-1035-90 from Glen research). The oligonucleotides terminated with Y and Z can be prepared from the corresponding X terminated oligonucleotides using the general procedure:

Templates:

Ah 28:
(SEQ ID NO: 18)
5'-GCTGTCTGCAAGTGAACCGATGCCAGTAGC

Ah 38:
(SEQ ID NO: 19)
5'-AGCTGGATGCTCGACAGGTCCCGATGCAATCCAGAGG TCG

Ah7:
(SEQ ID NO: 20)
5'-GCTGTCTGCAAGTGAACTCGTACGAGTAGCGACAGTCGACATCGGTC

ACG-biotin-3'

Ah 8:
(SEQ ID NO: 21)
5'-GCTGTCTGCAAGTGACACTCGTACGAGTAGCGACAGTCGACATCGGT

CACG-biotin-3'

Ah 9:
(SEQ ID NO: 22)
5'-GCTGTCTGCAAGTGACGACTCGTACGAGTAGCGACAGTCGACATCGG

TCACG-biotin-3'

Ah 11:
(SEQ ID NO: 23)
5'-

GCTGTCTGCAAGTGACGACTGATCCAGTGACATGCGTACCATCGAACTCG

TACGAGTAGCGACAGTCGACATCGGTCACG-biotin-3'

The templates was prepared by conventional phosphoramidate synthesis.

Buffers.
Buffer A (100 mM Hepes pH=7.5, 1 M NaCl)
Buffer B: (100 mM NaPO$_4$ pH=6, 1 M NaCl)
Buffer C: (100 mM NaBorate pH=9, 1 M NaCl)
Buffer D: (100 mM NaBorate pH=10, 1 M NaCl)
Buffer E: (500 mM NaPO$_4$ pH=7, 1 M NaCl)
Buffer F: (500 mM NaPO$_4$ pH=8, 1 M NaCl)
Annealing of DNA Oligonucleotides.

Mix oligos in relevant buffer and heat at 80° C. then cool to 28° C. (−2° C./30 sek).

5'-Labeling with $^{32}$P.

Mix 200 pmol oligonucleotide, 2 µl 10× phosphorylation buffer (Promega cat #4103), 1 µl T4 Polynucleotid Kinase (Promega cat #4103), 1 µl γ-$^{32}$P ATP, H$_2$O ad 20 µl. Incubate at 37° C., 10-30 minutes.

PAGE (Polyacrylamide Gel Electrophoresis).

The samples are mixed with formamide dye 1:1 (98% formamide, 10 mM EDTA, pH 8, 0.025% Xylene Cyanol, 0.025% Bromphenol Blue), incubate at 80° C. for 2 minutes, and run on a denaturing 10% polyacrylamide gel. Develop gel using autoradiography (Kodak, BioMax film).

Example 1

Mix 2 µl Buffer A, 2 µl relevant oligo 1 (2 pmol/ul), 2 µl relevant oligo 2 (2 pmol/ul), 4 µl relevant oligo 3 (2 pmol/ul) (See table I, below).

TABLE I

| Experiment | Oligo 1 ($^{32}$P-labelled) | Oligo 2 | Oligo 3 |
| --- | --- | --- | --- |
| A | Ah 3 | Ah 4 | Ah 7 |
| B | Ah 5 | Ah 6 | Ah 7 |
| C | Ah 5 | Ah 6 | None |
| D | Ah 5 | Ah 6 | Ah 8 |
| E | Ah 5 | Ah 6 | Ah 9 |
| F | Ah 14 | Ah 6 | Ah 7 |

Anneal as described above. Add 1 μl 100 mM, 1 μl 10 mM, or 0.1 μl 10 mM TSAT (Tris-succinimidyl aminotriacetate, Pierce cat #33063 dissolved in DMSO). Incubate at 25° C. for about 1 h, then analyze by 10% urea polyacrylamide gel electrophoresis.

The results are shown in FIG. 1.

Example 2

Mix 2 μl Buffer A, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table II, below)

TABLE II

| Experiment | Oligo 1 ($^{32}$P-labelled) | Oligo 2 | Oligo 3 |
| --- | --- | --- | --- |
| G | Ah5 | Ah6 | None |
| H | Ah5 | Ah6 | Ah7 |
| I | Ah5 | Ah6 | Ah8 |
| J | Ah5 | Ah6 | Ah9 |
| K | Ah5 | Ah6 | Ah11 |

Anneal as described above. Add 1 μl 100 mM, 10 mM or 1 mM TSAT (Tris-succinimidyl aminotriacetate, Pierce cat #33063 dissolved in DMSO). Incubate at 25° C. for about 5 h, then run 10% urea polyacrylamide gel, as described above.

Figure 2:
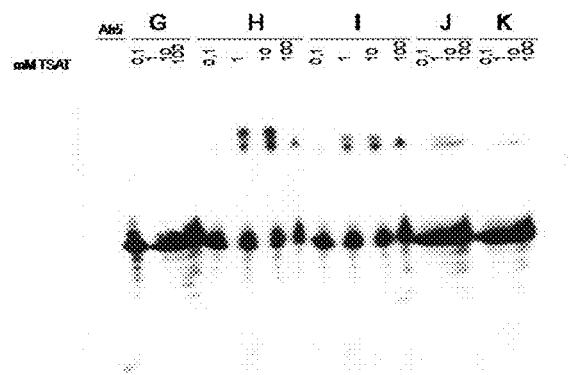
FIG. 2 shows a reproduction of a PAGE gel showing two oligonucleotides annealed to common template and cross-linked with a spacing of 0, 1, 2, and 30 base pair.

The results are shown in FIG. 2

Example 3

Mix 2 μl Buffer A, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table III, below)

TABLE III

| Experiment | Oligo 1 ($^{32}$P-labelled) | Oligo 2 | Oligo 3 |
| --- | --- | --- | --- |
| L | Ah 1 | Ah 6 | None |
| M | Ah 1 | Ah 6 | Ah 7 |
| N | Ah 1 | Ah 6 | Ah 8 |
| O | Ah 1 | Ah 6 | Ah 9 |
| P | Ah 1 | Ah 6 | Ah 11 |

Anneal as described above. Add 1 μl 1M, 100 mM, 10 mM or 1 mM EDC (1-Ethyl-3-(3-dimethylaminopropyl) Carbodiimide Hydrochloride, Fluka #03450) and 1 μl 100 mM NHS (N-Hydroxysuccinimid) (Aldrich cat #13,067-2). Incubation at 25° C. for about 5 h, and analyze by 10% urea polyacrylamide gel electrophoresis, as described above.

Figure 3:
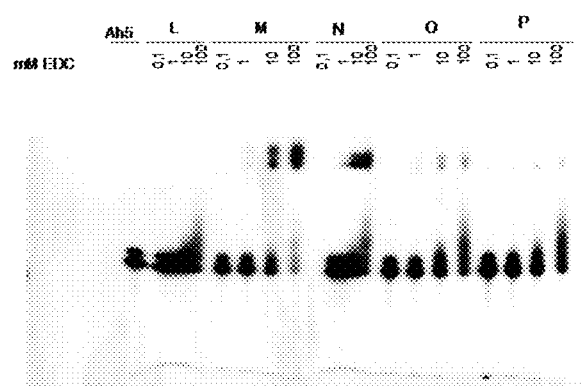
FIG. 3 shows a reproduction of a PAGE gel displaying cross-linking of two oligonucleotides terminated with a amine and carboxylic acid, respectively.

The results are shown in FIG. 3.

Example 4

Mix 2 μl buffer A, B, C, D, E or F, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table IV, below)

TABLE IV

| Experiment | Oligo 1 ($^{32}$P-labelled) | Oligo 2 | Oligo 3 |
| --- | --- | --- | --- |
| Q | Ah 1 | Ah 6 | Ah 7 |
| R | Ah 5 | Ah 6 | Ah 7 |

Anneal as described above. Experiment Q is added 1 μl 100 mM EDC and 1 μl 100 mM NHS. Experiment R is added 1 μl 100 mM TSAT. Incubate at 25° C. for about 1.5 h, and then analyze by 10% urea polyacrylamide gel electrophoresis.

Figure 4:
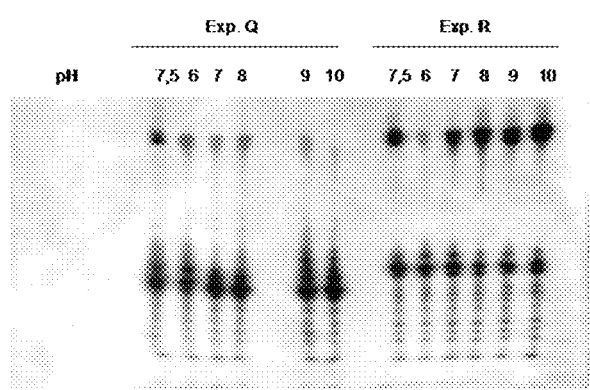
FIG. 4 shows a reproduction of a PAGE gel showing the influence of different pH profiles on cross-linking efficiency.

The results are shown in FIG. 4.

Example 5

Mix 2 μl buffer A or D, 2 μl relevant oligo 1 (0.2 pmol/ul), 2 μl relevant oligo 2 (10 pmol/ul), 2 μl relevant oligo 3 (10 pmol/ul), 2 μl H$_2$O. (See table V, below).

TABLE V

| Experiment | Oligo 1 ($^{32}$P-labelled) | Oligo 2 | Oligo 3 |
| --- | --- | --- | --- |
| S | Ah 5 | Ah 6 | Ah 7 |
| T | Ah 14 | Ah 6 | Ah 7 |

Anneal as described above. Add 1 μl 100 mM TSAT. Incubate at 25° C. for about 1.5 h, and then analyze by 10% urea polyacrylamide gel electrophoresis.

Figure 5:
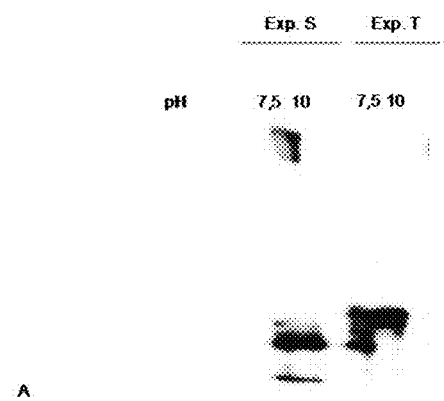
FIG. 5 shows a reproduction of a PAGE gel showing the influence of different pH profiles on cross-linking efficiency.

The results are shown FIG. 5.

Example 6

Mix 2 μl buffer A, B or D, 1 μl relevant oligo 1 (2 pmol/ul), 1 μl relevant oligo 2 (10 pmol/ul), 1 μl relevant oligo 3 (10 pmol/ul), 5 μl H$_2$O. (See table VI, below).

TABLE VI

| Experiment | Oligo 1 ($^{32}$P-labelled) | Oligo 2 | Oligo 3 |
| --- | --- | --- | --- |
| U$_A$ (Buffer A) | Ah 23 | Ah 27 | Ah 28 |
| V$_A$ (Buffer A) | Ah 23 | Ah 27 | None |
| U$_B$ (Buffer B) | Ah 23 | Ah 27 | Ah 28 |
| V$_B$ (Buffer B) | Ah 23 | Ah 27 | None |
| X (Buffer D) | Ah 24 | Ah 27 | Ah 28 |
| Y (Buffer D) | Ah 24 | Ah 27 | None |

Anneal as described above. Experiment U and V is added 1 μl 100 mM EDC and 1 μl 100 mM NHS, incubated for about 1 h at 24° C., and then added 2 μl buffer C, then incubated for 30 minutes at 24° C. Experiment X and Y is added 2 μl 50 mM TSAT. Incubate at 24° C. for about 1.5 h, and then analyzed by 10% urea polyacrylamide gel electrophoresis, as described above.

Figure 6:
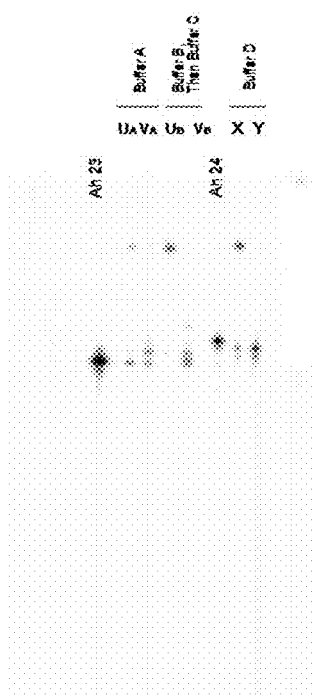
FIG. 6 shows a reproduction of a PAGE gel displaying cross-linking efficiency at pH 9.

The results are shown in FIG. 6.

Example 7

Mix 2 μl first Buffer (See below), 1 μl Ah 23 (2 pmol/ul), 1 μl Ah 27 (10 pmol/ul), 1 μl Ah28 (10 pmol/ul), 5 μl H$_2$O. Anneal as described above, then add 1 μl 100 mM NHS and 1 μl 1 M EDC, incubate for 30 minutes at 24° C., then add 3 μl second buffer (See below). Incubate for 40 minutes at 24° C., and then analyze by 10% urea polyacrylamide gel electrophoresis.

TABLE VII

| Experiments | First Buffer | Second Buffer |
| --- | --- | --- |
| 7-1 | Buffer A | Buffer A |
| 7-2 | Buffer A | Buffer C |
| 7-3 | Buffer A | Buffer D |
| 7-4 | Buffer B | Buffer D |
| 7-5 | Buffer B | Buffer C |

Figure 7:
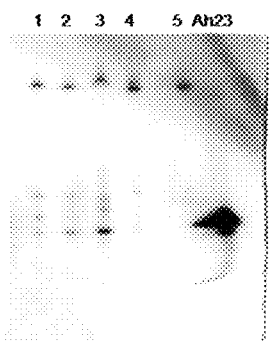
FIG. 7 shows a reproduction of a PAGE gel displaying cross-linking efficiency at pH 10.

The results are shown in FIG. 7.

Example 8

Mix 8-1: Mix 2 μl buffer B, 5 μl Ah36 (0.4 pmol/ul), 1 μl Ah37 (2 pmol/ul), 1 μl Ah38 (2 pmol/ul), 1 μl H$_2$O.

Mix 8-2: Mix 2 μl buffer B, 5 μl Ah36 (0.4 pmol/ul), 1 μl Ah37 (2 pmol/ul), 2 μl H$_2$O.

Anneal by heating to 80° C., then cool to 44° C. (−2° C./30 sek).

Add 1 μl 100 mM NHS and 1 μl 1 M EDC. Incubate at indicated temperatures (see below) for 45 minutes, then add 2 μl Buffer D. Incubate for about 2 h, and then analyze by 10% urea polyacrylamide gel electrophoresis.
Incubation Temperatures:
45° C., 48.2° C., 53.0° C., 58.5° C., 63.1° C., 65.6° C.

Figure 8:
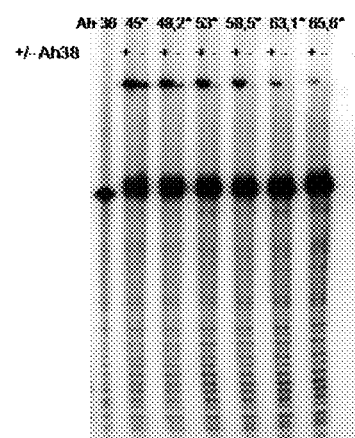
FIG. 8 shows a reproduction of a PAGE gel analysing the effect of absence of template when a 10 mer zipper box is used.

The results are shown in FIG. 8.

Example 9

Mix 9-1: Mix 2 μl buffer B, 1 μl Ah36 (2 pmol/ul), 1 μl Ah51 (2 pmol/ul), 1 μl Ah38 (2 pmol/ul), 5 μl H$_2$O.

Mix 9-2: Mix 2 μl buffer B, 1 μl Ah36 (2 pmol/ul), 1 μl Ah51 (2 pmol/ul), 6 μl H$_2$O Anneal by heating to 80° C., then cool to 35° C. (−2° C./30 sek)(For temperatures 1 to 6), or heat to 80° C., then cool to 15° C. (−2° C./30 sek)(For temperatures 7 to 12). Add 1 μl 100 mM NHS and 1 μl 1 M EDC. Incubate at indicated temperatures (see below) for 1 h, then add 2 μl Buffer D. Incubate for 1 h, and then analyze by 10% urea polyacrylamide gel electrophoresis, as described above.
Incubation Temperatures:
1) 34.9° C., 2) 36.3° C., 3) 40.3° C., 4) 45.7° C., 5) 51.0° C., 6) 55.77, 7) 14.9° C., 8) 17.8° C., 9) 22.7° C., 10) 28.3° C., 11) 31.0° C., 12) 36° C.

Mix 9-3: Mix 2 μl buffer B, 0.5 μl Ah36 (2 pmol/ul), 1 μl Ah51 (2 pmol/ul), 1 μl Ah38 (2 pmol/ul), 5.5 μl H$_2$O Mix 9-4: Mix 2 μl buffer B, 0.5 μl Ah36 (2 pmol/ul), 1 μl Ah51 (2 pmol/ul), 6.5 μl H$_2$O Anneal by heat at 80° C. then cool to 5° C. (−2° C./30 sek).

Add 1 μl 100 mM NHS and 1 μl 1 M EDC. Incubate at different temperatures (see below) for 1 h, then add 2 μl Buffer D. Incubate for 1 h, and then analyze by 10% urea polyacrylamide gel electrophoresis.
Incubation Temperatures:
1) 5.9° C., 2) 9.9° C., 3) 12.6° C., 4) 18.3° C., 5) 23.3° C., 6) 27.9° C. 7) 35.6° C., 8) 45.9° C.

Figure 9A:
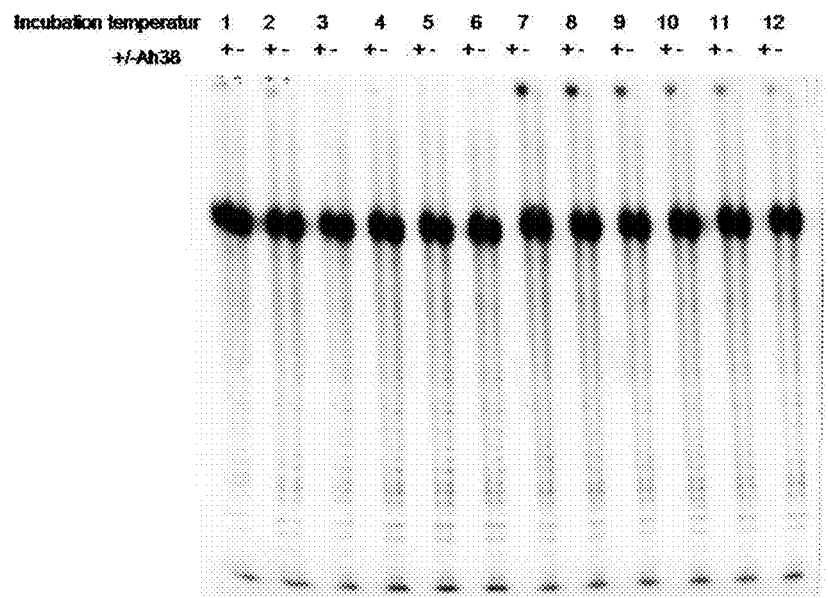
FIGS. 9A and B shows a reproduction of a PAGE gel analysing the effect higher incubation temperature on the cross-linking efficiency.
Figure 9B:
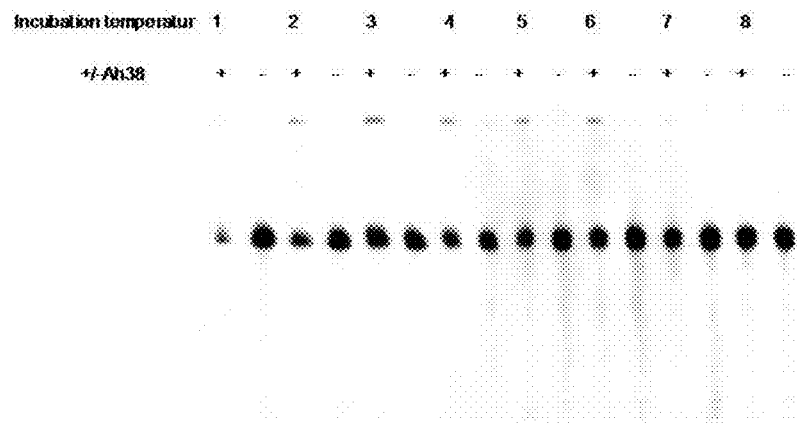

The results are shown in FIGS. 9, A and B.

Example 10

Mix 2 μl buffer A, 1 μl relevant oligo 1 (2 pmol/ul), 1 μl relevant oligo 2 (10 pmol/ul), 1 μl relevant oligo 3 (10 pmol/ul), 5 μl H$_2$O. (See table below). Anneal as described above.

Add 1 μl 100 mM NHS and 1 μl 1 M EDC. Incubate at different temperatures 1) 7.7° C., 2) 15.4° C., 3) 21.0° C. 4) 26.2° C. for about 2 h, and 5) 10° C. for 1 sec. and then 35° C. for 1 sec. Repeat 99 times. Analyze by 10% urea polyacrylamide gel electrophoresis.

TABLE VIII

| Experiment | Oligo 1 ($^{32}$P) | Oligo 2 | Oligo 3 |
| --- | --- | --- | --- |
| 10-1 | Ah36 | None | Ah38 |
| 10-2 | Ah36 | None | None |
| 10-3 | Ah36 | Ah51 | Ah38 |
| 10-4 | Ah36 | Ah51 | None |
| 10-5 | Ah36 | Ah67 | Ah38 |
| 10-6 | Ah36 | Ah67 | None |
| 10-7 | Ah36 | Ah69 | Ah38 |
| 10-8 | Ah36 | Ah69 | None |

The results are shown in FIG. 10 A and FIG. 10 B.

Example 11

Mix 2.5 μl buffer A, 1 μl relevant oligo 1 (2 pmol/ul), 1 μl relevant oligo 2 (10 pmol/ul), 1 μl relevant oligo 3 (10 pmol/ul), 4.5 μl H$_2$O. (See table below). Anneal by heating to 80° C. and then cool to 30° C. or 55° C. Add 1 μl 100 mM NHS and 1 μl 1 M EDC. Incubate at 30° C. or 55° C. Then analyze by 10% urea polyacrylamide gel electrophoresis.

TABLE IX

| Experiment | Oligo 1 ($^{32}$P-labelled) | Oligo 2 | Oligo 3 |
| --- | --- | --- | --- |
| 11-1 | Ah36 | Ah37 | Ah38 |
| 11-2 | Ah36 | Ah37 | None |
| 11-3 | Ah65 | Ah66 | Ah38 |
| 11-4 | Ah65 | Ah66 | None |
| 11-5 | Ah36 | Ah66 | Ah38 |
| 11-6 | Ah36 | Ah66 | None |
| 11-7 | Ah65 | Ah37 | Ah38 |
| 11-8 | Ah65 | Ah37 | None |

Figure 11:
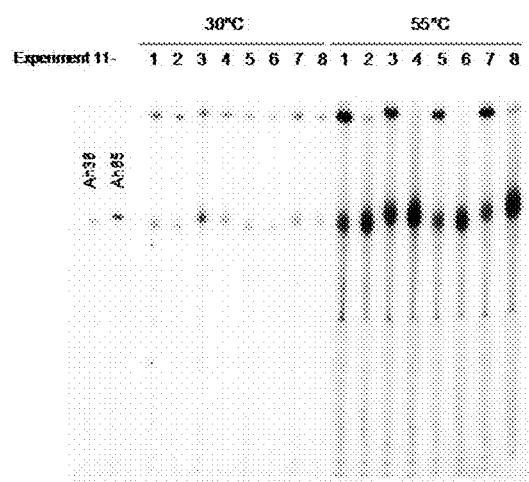
FIG. 11 shows an image of a PAGE gel displaying the effect of different temperatures on the cross-linking efficiency when a 10 mer zipper box is used.

The results are shown in FIG. 11.

Discussion of the Results of the Examples 1 to 11

Influence of Linker Length and Spacing Between the Reactive Groups on Cross-Linking Efficiency.

We first examined the effect of changing the length of the linker that connects the amine and the nucleotide. Oligos Ah3 and Ah5 contain an amine separated from the base of the nucleotide by seven and eleven bonds, respectively (called amino modifier C2 dT and amino modifier C6 dT, see formulae above). These oligos were annealed immediately next to oligo Ah 4 or Ah6 (carrying amino modifier C2 dT and amino modifier C6 dT, respectively), i.e., with a spacing between the two oligos of 0 base pairs.

As seen in FIG. 1, lanes A and B, the efficiency of cross-linking is approximately equal for either amino modifier.

In all the following experiments, the oligo Ah5 (containing amino modifier C6 dT) was used as the reactive group amine.

Next, the two oligos were annealed to templates with spacings of 0, 1, 2, and 30 base pairs between the two oligos, and the efficiency of cross-linking examined. First, cross-linking using TSAT (Tris-succinimidyl aminotriacetate, Pierce cat #33063 dissolved in DMSO) was investigated. When oligos Ah5 and Ah6 were used, the efficiency of the cross-linking reaction were highest with a spacing of 0 base pairs (FIG. 1, lanes B; FIG. 2, panel H), less efficient with a spacing of 1 base pairs (FIG. 1, lanes D; FIG. 2, panel I), and very inefficient with spacings of 2 and 30 base pairs (FIG. 1, lanes E and F; FIG. 2, panel J and K).

Second, cross-linking of an amine and a carboxylic acid was examined. In this experiment, EDC (1-Ethyl-3-(3-dimethylaminopropyl) Carbodiimide Hydrochloride and NHS (N-Hydroxysuccinimide) was added in order to crosslink the two reactive groups. When oligos Ah1 and Ah6 were used, the efficiency of cross-linking was again highest for the shortest spacing of zero base pairs (FIG. 3, panel M), relatively high for a spacing of one base pairs (FIG. 3, panel N), and modest and insignificant for spacings of 2 and 30 base pairs, respectively (FIG. 3, panel O and P).

Optimization of TSAT and EDC Concentration.

The importance of TSAT concentration was tested by using the oligos Ah5 and Ah 6. A concentration of 1 or 10 mM TSAT leads to more efficient cross-linking than both 0.1 mM and 100 mM TSAT (FIGS. 1 and 2). The lower cross-linking efficiency obtained when using the highest TSAT concentration (100 mM) may be explained by two TSAT molecules reacting with each of the neighbouring amines.

Next, the importance of EDC concentration was examined for cross-linking an oligo carrying an amine (Ah6) and an oligo carrying a carboxylic acid (Ah1). Previously, it has been found that NHS concentrations of about 10 mM provides the highest cross-linking efficiency when used together with EDC. As shown in FIG. 3, 100 mM EDC results in the highest cross-linking efficiency when compared to 0.1 mM, 1 mM and 10 mM EDC.

Optimization of pH for TSAT and EDC/NHS Cross-Linking Reactions.

Next, we tested the influence of different pH profiles for cross-linking efficiency using either the EDC/NHS or TSAT reagents.

A pH of 10 provides the most efficient TSAT cross-linking of two amines (FIG. 4, panel R; FIG. 5, panel S). Oligos Ah5 and Ah6 were used in this study. In experiment 6 (FIG. 6) a cross-linking efficiency of 80% is obtained using pH 10, and a spacing of zero base pairs between amine-carrying oligos Ah24 and Ah27. In other experiments where the linker that separates the complementing element (the region of the oligo that anneals to the template) and the reactive group (amine or carboxylic acid) is much larger (e.g. FIGS. 11 and 12), the cross-linking efficiency is much lower.

Oligos Ah1 and Ah6 were next used to examine the influence of different pH profiles on the the cross-linking efficiency using EDC/NHS. The constant pH that mediates the most efficient cross-linking is pH 7.5 (FIG. 4, panel Q). However, an even better cross-linking efficiency is obtained when the pH is initially kept at pH 6, and then increased to pH 9 (FIG. 6) or 10 (FIG. 7). In the latter two experiments, oligos Ah23 and Ah27 were used. Under those conditions, the cross-linking efficiency is almost 100%. Note, that in these experiments the linker that connects the reactive group and the complementing element is relatively short (e.g. 11 bonds for the Ah27).

Examination of Cross-Linking Efficiency when Using a Zipper Box Sequence.

We next examined the cross-linking efficiency using oligos carrying reactive groups (amine or carboxylic acid) where the linker connecting the reactive group and the annealing region were approximately 25 nucleotides.

In a first experiment oligos Ah36 (carrying a carboxylic acid) and Ah67 (carrying an amine) were used. The template used (Ah38) anneals the two oligos immediately adjacent, i.e. with a spacing of zero base pairs.

Under the conditions of the experiment, less than 5% cross-linking efficiency is observed, and only at the highest tested temperature (FIG. 10, A and B, lanes 5).

In order to improve the cross-linking efficiency, we introduced a so-called zipper box sequence at the 5'- and 3' end of oligos Ah67 and Ah36, respectively, the same termini that carries the reactive groups. The zipper-boxes are complementary sequences, and thus may bring the reactive groups of the two oligos into closer proximity. Two different lengths of zipper boxes were tested, namely a 10'mer zipper box (Ah37/Ah66, Ah37 forming a DNA duplex of 10 base pairs) and a 5'mer zipper box (forming a DNA duplex of 5 base pairs). See FIG. 12. Moreover, different designs of zipper boxes were tested, e.g. oligos in which the reactive group is attached immediately adjacent to the zipper box (Ah36, Ah37, Ah51), or placed two nucleotides upstream from the zipper box (Ah65, Ah66), or placed in the middle of the zipper box (Ah67).

Figure 10A:
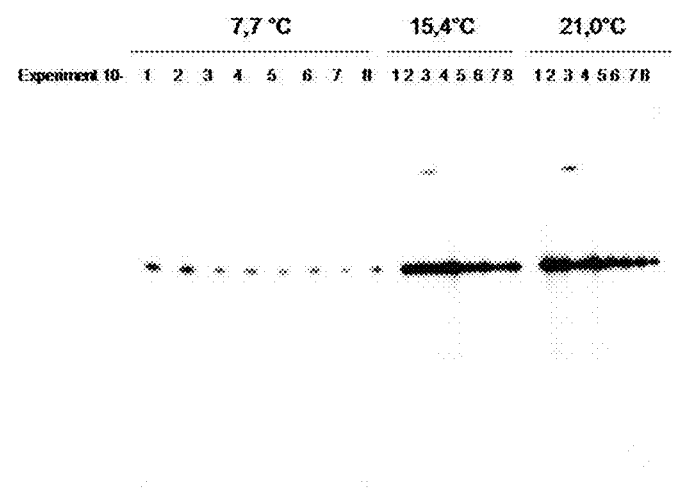
FIGS. 10A and B shows an image of a PAGE gel displaying the effect of a 5 mer zipper box on the cross-linking efficiency.
Figure 10B:
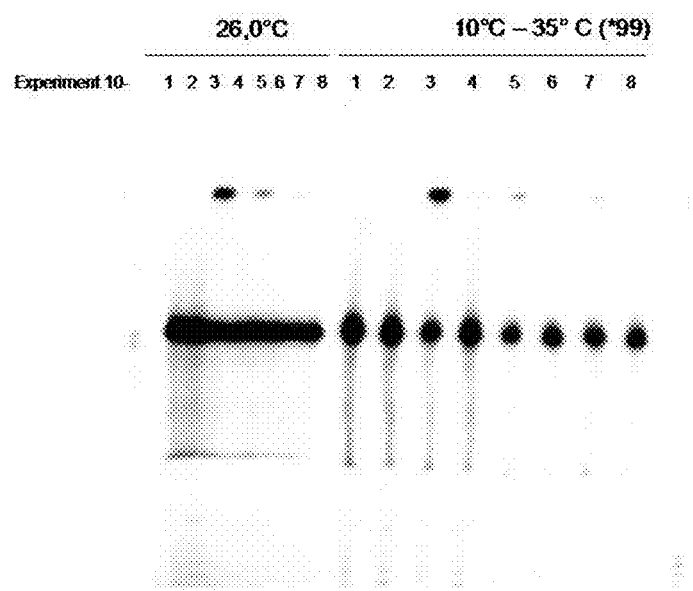

We first tested the effect of the 5'mer zipper box on cross-linking efficiency. As can be seen, the 5'mer zipper box improves the cross-linking efficiency dramatically (FIG. 10, A and B, compare lanes 3 and lanes 5). Note that the template is absolutely required for cross-linking at all temperatures tested. The highest cross-linking efficiency is obtained when the temperature is cycled 99 times up and down between 10° C. and 35° C. (FIG. 10B). A high efficiency is also obtained when the temperature is kept constant at 21° C. or 26° C. (FIG. 10A and B, lanes 3). The cross-linking efficiency does not improve further at temperatures above 26° C. (FIG. 9, A and B).

We next tested the efficiency of cross-linking in the 10'mer zipper box format. Oligos Ah36 and Ah37 were annealed to template Ah38, and the cross-linking efficiency examined at various temperatures. A surprisingly high degree of cross-linking in the absence of template was observed (FIG. 8, 45° C. and 48.2° C.). However, at temperatures above 58.5° C., no cross-linking is observed in the absence of template.

Next, the different locations of the reactive groups relative to the zipper box were tested. As shown in FIG. 10, A and B, lanes 7, the cross-linking efficiency decreases dramatically when one of the two reactive groups is located in the middle of the zipper box (i.e., the reactive group is attached to a nucleotide involved in DNA double helix formation; Ah67).

The location of the reactive groups relative to the zipper box was also tested in the context of the 10'mer zipper box. In this context, when both reactive groups are separated from the zipper box by two nucleotides (Ah65, Ah66), the efficiency of cross-linking is slightly decreased (FIG. 11, compare lanes 1 and 3). The cross-linking efficiency is not changed dramatically when different combinations of Ah65, Ah66, Ah36 and Ah37 are tested (i.e., when the reactive groups are placed immediately next to the zipper box, or two nucleotides upstream). Note that the template is not absolutely required at all temperatures in the context of the 10'mer zipper box. This template-independency is particularly pronounced at lower temperature (e.g., FIG. 11, 30° C.).

Example 12

Trisamine Scaffold Building Block

An oligo containing a modified nucleobase having a carboxylic acid moiety, was synthesised using the conventional phosphoramidite approach:

```
                                (SEQ ID NO: 24)
5'-GAC CTG TCG AGC ATC CAG CTT CAT

GGG AAT TCC TCG TCC ACA ATG XT
```

X was incorporated using the commercially available carboxy-dT phosphoramidite (10-1035-90 from Glen research). The underlined nucleobases represent the zipper region.

Schematic Representation of the Reaction:

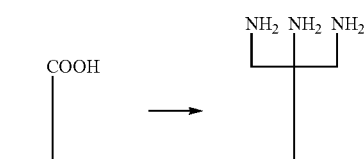

The oligo containing the modified nucleobase with a carboxylic acid moiety (1 nmol) was mixed with water (100 uL), hepes buffer (40 uL of a 200 mM, pH=7.5), NHS (20 uL of a 100 mM solution), EDC (20 uL of a freshly prepared 1 M solution) and tetrakis(aminomethyl)methane tetrahydrochloride (20 uL of a 100 mM solution). The reaction mixture was left o/n at room temperature. The volume was reduced to 60 uL by evaporation in vacuo. The pure oligo was obtained by addition of $NH_3$ conc. (20 uL) followed by HPLC purification. It was possible to isolate a peak after approximately 6 min using the following gradient: 0-3 minutes 100% A then 15% A and 85% B from 3-10 minutes then 100% B from 10-15 minutes then 100% A from 15-20 minutes. A=2% acetonitrile in 10 mM TEAA and B=80% acetonitrile in 10 mM TEAA.

Example 13

General Procedure for Attachment of a Functional Entity to a Thio Oligo

The following oligos containing a modified nucleobase, with a S-triphenylmethyl protected thio moiety, were synthesised using the conventional phosphoramidite approach:

```
                                (SEQ ID NO: 25)
5'-WCA TTG ACC TGT CTG CC (SEQ ID NO: 62)
internal biotin- TGT CAG TCG GTA CTG

TGG TAA CGC GGA TCG ACC T (SEQ ID NO: 26)
5'-WCA TTG ACC TGA ACC ATG (SEQ. ID NO: 63)
internal biotin- TA AGC TGC CTG TCA

GTC GGT ACT ACG ACT ACG TTC AGG CAA GA
```

W was incorporated using the commercially available thiol modifier phosphoramidite (10-1926-90 from Glen research). An internal biotin was incorporated using the commercially available phosphoramidite (10-1953-95 from Glen research). The nucleobases which are underlined indicates the zipper region.

The S-triphenylmethyl protected thio oligo (10 nmol) was evaporated in vacuo and resuspended in TEAA buffer (200 uL of a 0.1M solution, pH=6.4). $AgNO_3$ (30 uL of a 1 M solution) was added and the mixture was left at room temperature for 1-2 hours. DTT (46 uL of a 1M solution) was added and left for 5-10 minutes. The reaction mixture was spun down (20.000 G for 20 minutes) and the supernatant was collected. The solid was extracted with additional TEAA buffer (100 ul of a 0.1 M solution, pH=6.4). The pure thio oligo was obtained by conventional EtOH-precipitation.

Schematic Representation of the Loading Reaction:

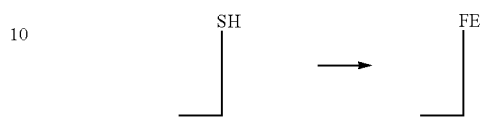

Each of the thio oligos (1 nmol) was dried in vacuo and treated with a chemical entity comprising the functional entity:

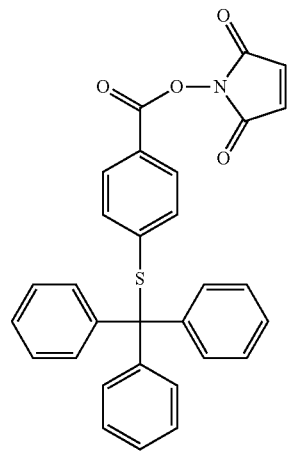 [SMILES: O=C(ON1C(=O)C=CC1=O)c1ccc(SC(c2ccccc2)(c2ccccc2)c2ccccc2)cc1]

in dimethylformamide (50 ul of a 0.1 M solution) and left o/n at rt. The building block was spun down (20.000 G for 10 minutes) and the supernatant removed. Dimethylformamide (1 mL) was added and the building block was spun down (20.000 G for 10 minutes). The dimethylformamide was removed and the loaded thio oligo was resuspended in TEAA buffer (25 uL of a 0.1M solution, pH=6.4) and analysed by HPLC.

Example 14

Synthesis of a Encoded Scaffolded Molecule

Template

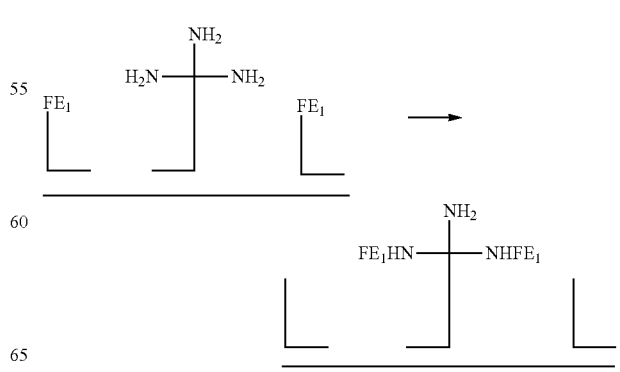

Figure 15:
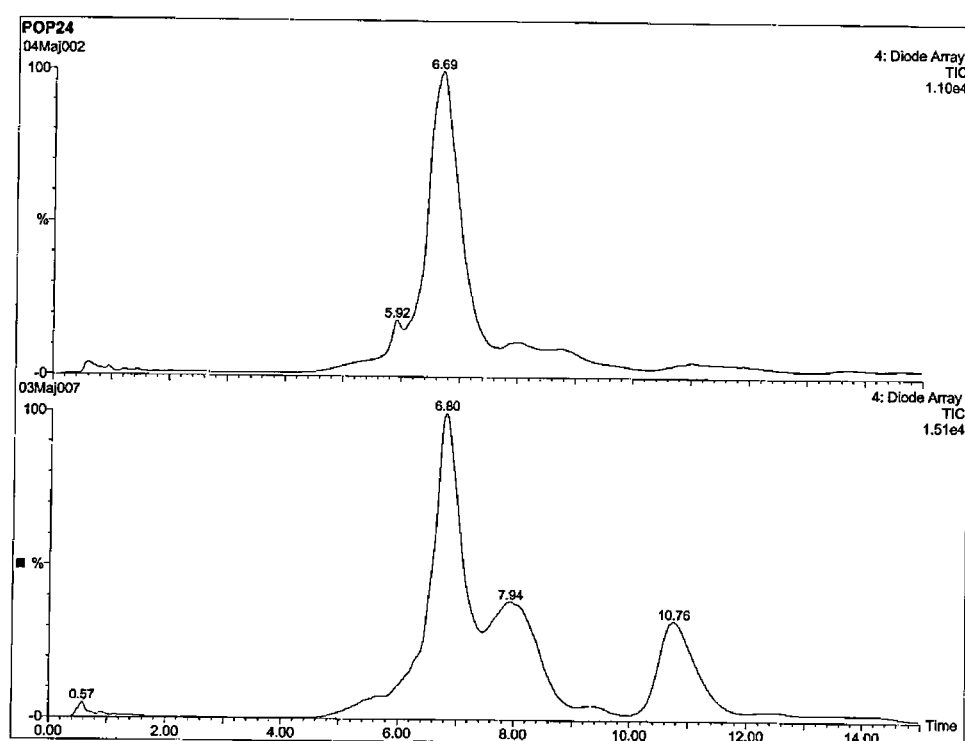
FIG. 15 shows a LC-chromatogram of the transfer of two identical functional entities to a scaffold molecule.

The template oligo 5'-BTCTTGCCTGAACGTAGTCG-TAGGTCGATCCGCGTTACCAGAGCTGGATGCTC-GACAGGTCCCGATGCAATCCAGAGGTCG (SEQ ID NO: 27) (1 nmol) was mixed with the two building blocks prepared in example 13 and with the scaffold building block prepared in example 12 (1 nmol) in hepes-buffer (20 uL of a 100 mM hepes and 1 M NaCl solution, pH=7.5) and water (added to a final volume of 100 uL). The building blocks were annealed to the template by heating to 50° C. and cooled (−2° C./30 second) to 30° C. The mixture was then left o/n at a fluctuating temperature (10° C. for 1 second then 35° C. for 1 second). The oligo complex was attached to streptavidine by addition of streptavidine beads (100 uL, prewashed with 2×1 mL 100 mM hepes buffer and 1M NaCl, pH=7.5). The beads were washed with hepes buffer (1 mL). The trisamine scaffolded building block was separated from the streptavidine bound complex by addition of water (200 uL) followed by heating to 70° C. The water was transferred and evaporated in vacuo, resuspended in TEAA buffer (45 uL of a 0.1 M solution) and product formation analysed by HPLC (see FIG. 15).

The HPLC chromatogram shows the transfer of two functional entities to a scaffold building block. The top chromatogram shows the reference scaffold building block. The bottom chromatogram show the streptavidine purified scaffold building block after the partial transfer of one (peak at 7.94 minutes) and two (peak at 10.76 minutes) identical functional entities. The following gradient was used: 0-3 minutes 100% A, then 15% A and 85% B from 3-10 minutes, then 100% B from 10-15 minutes. A=2% acetonitrile in 10 mM TEAA and B=80% acetonitrile in 10 mM TEAA.

Due to the lipophilic nature of the functional entities a longer retention time, in the HPLC chromatogram, of the scaffolded molecule with two functional entities compared to one functional entity, was observed. The efficiency of the templated synthesis of a scaffolded molecule with the two identical functional entities was about 25% (peak at 10.76 minutes in FIG. 15).

General Methods and Materials for Examples 15 to 21

In order to examine the reaction efficiency between two reactive groups, each coupled to a oligonucleotide, when the two oligos are annealed on the same template, the two set-ups shown in FIG. 16 was used (set-up A and set-up B). The two oligos contain terminal nucleotides derivatized with a carboxylic acid or an amine. After reaction ("cross-linking") of the reactive groups on the termini of the two oligos, the cross-linking efficiency may be analyzed by polyacrylamide gel electrophoresis, as the two oligos become coupled as a result of this cross-linking, and therefore migrate slower through the column DNA Oligos:
X=Carboxy-dT
Z=Amino Modifier C6
6=Amino-Modifier 5 cat. Nr. 10-1905

Zipper box sequences are underlined. Note that when the building block zipper boxes interact with zipper boxes in the template, the length of the zipper box duplex is one nucleotide longer than is underlined.

AH36:
(SEQ ID NO: 11)
5'-
CGACCTCTGGATTGCATCGGTCATGGCTGACTGTCCGTCGAATGTGTCCA
GTTAC X

AH51:
(SEQ ID NO: 13)
5'-
ZGTAACACCTGTGTAAGCTGCCTGTCAGTCGGTACTGACCTGTCGAG-
CATCCAGCT

AH82:
(SEQ ID NO: 28)
5'-ZGTAACACCTGGACCTGTCGAGCATCCAGCT

AH 201:
(SEQ ID NO: 29)
5'-TCTGGATTGCATCGGGAGTTACX

AH133:
(SEQ ID NO: 30)
5'-
ZGTAACTCCTGTGTAAGCTGCCTGTCAGTCGGTACTGACCTGTCGAG-
CATCCAGCT

AH134:
(SEQ ID NO: 31)
5'-
ZGTAACTGCTGTGTAAGCTGCCTGTCAGTCGGTACTGACCTGTCGAG-
CATCCAGCT

AH135:
(SEQ ID NO: 32)
5'-
ZGTAACTGGTGTGTAAGCTGCCTGTCAGTCGGTACTGACCTGTCGAG-
CATCCAGCT

AH 142:
(SEQ ID NO: 33)
5'-
CGACCTCTGGATTGCATCGGTCATTTTTTTTTTTTTTTTTTT-
GGCTGACTGTCCGTCGAATGTGTCCAGTTACX

AH 156:
(SEQ ID NO: 34)
5'-ZGACCTGTCGAGCATCCAGCT

AH 202:
(SEQ ID NO: 35)
5'-TCTGGATTGCATCGGGTTACX

AH 203:
(SEQ ID NO: 36)
5'-TCTGGATTGCATCGGTTTTX

AH 236:
(SEQ ID NO: 37)
5'-6GTAACACCTGGACCTGTCGAGCATCCAGCT

AH 240:
(SEQ ID NO: 38)
5'-CGACCTCTGGATTGCATCGGGCACGGTTACX

AH 249:
(SEQ ID NO: 39)
5'-ZCTGGACAGCTCGTAGGTCGTTTTTTTTTTT

AH 251:
(SEQ ID NO: 40)
5'-ZGACCTGTCGAGCATCCAGCT

AH 252:
(SEQ ID NO: 41)
5'-XGACCTGTCGAGCATCCAGCT

AH 255:
(SEQ ID NO: 42)
5'-CGACCTCTGGATTGCATCGGTGTTACZ

AH 258:
(SEQ ID NO: 43)
5'-ACGACTACGTTCAGGCAAGAGTTACZ

AH 260:
(SEQ ID NO: 44)
5'-XCTGGACAGCTCGTAGGTCGTTTTTTTTTT

AH 261:
(SEQ ID NO: 45)
5'-CGACCTCTGGATTGCATCGGZ

AH 262:
(SEQ ID NO: 46)
5'-CGACCTCTGGATTGCATCGGTTACZ

AH 270:
(SEQ ID NO: 47)
5'-6GTAACGACCTGTCGAGCATCCAGCT

AH 271:
(SEQ ID NO: 48)
5'-6GTAACTGGACCTGTCGAGCATCCAGCT

AH 272:
(SEQ ID NO: 49)
5'-ACGACTACGTTCAGGCAAGAGTTACX

AH 273:
(SEQ ID NO: 50)
5'-ACGACTACGTTCAGGCAAGAGCGTTACX

AH 274:
(SEQ ID NO: 51)
5'-ACGACTACGTTCAGGCAAGAGCACGGTTACX

AH 275:
(SEQ ID NO: 52)
5'-CGACCTCTGGATTGCATCGGGCGTTACX

AH 276:
(SEQ ID NO: 53)
5'-CTGGTAACGCGGATCGACCTGCACGGTTACX

AH 277:
(SEQ ID NO: 54)
5'-CTGGTAACGCGGATCGACCTGCGTTACX

The oligonucleotides were prepared following the conventional phosphoramidite approach. X represents the commercially available carboxy-dT phosphoramidite (10-1035-90 from Glen research). Z represents amino modifier C6 dT (10-1039-from Glen Research). 6 represents the aminomodifier 5 (10-1905 from Glen Research)
Templates:
Zipper Box Sequences are Underlined.

AH38:
(SEQ ID NO: 19)
5'-AGCTGGATGCTCGACAGGTCCCGATGCAATCCAGAGGTCG

AH140:
(SEQ ID NO: 55)
5'-
AGCTGGATGCTCGACAGGTCAGGTCGATCCGCGTTACCAGTCTTGCCTGA
ACGTAGTCGTCCGATGCAATCCAGAGGTCG

AH 154:
(SEQ ID NO: 56)
5'-
AGCTGGATGCTCGACAGGTCAAGTAACAGGTCGATCCGCGTTACCAGTCT
TGCCTGAACGTAGTCGTCCGATGCAATCCAGAGGTCG

AH 250:
(SEQ ID NO: 57)
5'-
CGACCTACGAGCTGTCCAGAAGTAACAGGTCGATCC

AH 256:
(SEQ ID NO: 58)
5'-
AGCTGGATGCTCGACAGGTCAAGTAACACCAGGTCGATCCGCGTTACCA
GTCTTGCCTGAACGTAGTCGTCCGATGCAATCCAGAGGTCG

AH 263:
(SEQ ID NO: 59)
5'-
CGACCTACGAGCTGTCCAGAAGTAACAGGTCGATCCGCGTTACCAGTCT
TGCCTGAACGTAGTCGTCTGGTCACGTGGATCCTTGA

AH 278:
(SEQ ID NO: 60)
5'-
AGCTGGATGCTCGACAGGTCGAGGTCGATCCGCGTTACCAGTCTT-
GCCTGAACGTAGTCGTCCGATGCAATCCAGAGGTCG

AH 279:
(SEQ ID NO: 61)
5'-
CGACCTAC-
GAGCTGTCCAGAAGTAACTTTTTTTTTTTTTTTTTTTTTTTTTTTTT
TTTTTTTTCTGGTCACGTGGATCCTTGA

The templates were prepared by conventional phosphoramidite synthesis.
Buffers:
Buffer A (100 mM Hepes pH=7.5; 1 M NaCl)
Buffer B (20 mM Hepes pH=7.5; 200 mM NaCl)
5'-Labeling with $^{32}$P.
Mix 5 pmol oligonucleotide, 2 µl 10× phosphorylation buffer (Promega cat #4103), 1 µl T4 Polynucleotide Kinase (Promega cat #4103), 1 µl γ-$^{32}$P ATP, add H$_2$O to 20 µl. Incubate at 37° C., 10-30 minutes.
PAGE (Polyacrylamide Gel Electrophoresis).
The samples are mixed with formamide dye 1:1 (98% formamide, 10 mM EDTA, pH 8, 0.025% Xylene Cyanol, 0.025% Bromphenol Blue), incubated at 80° C. for 2 minutes, and run on a denaturing 10% polyacrylamide gel. Develop gel using autoradiography (Kodak, BioMax film).

Example 15

In order to examine the effects of concentration on annealing efficiency, reaction efficiency and template dependency in the context of Set-up B, we did the following experiment, which included i) annealing and reaction at high building block and template concentration (experiments A and B), ii) annealing at high concentrations, followed by a 100-fold dilution and reaction at this low concentration (E and F), and iii) annealing and reaction at low concentrations (C and D). To examine the extent to which template-independent reactions occur, we also included a control complex, consisting of a competitor template and a competitor oligo carrying a reactive group (an amine).

Experimental

Mix 10 µl Buffer A, relevant oligos in various concentrations (See table X, below), and add H$_2$O to 50 µl.

TABLE X

| Experiment | Oligo 1 ($^{32}$P-labelled) (BB1) | Oligo 2 (BB0) | Oligo 3 (Template) | Oligo 4 (Competitor oligo) | Oligo 5 (Competitor template) |
|---|---|---|---|---|---|
| A | Ah 202 (1 pmol) | Ah 156 (5 pmol) | Ah 154 (5 pmol) | Ah 249 (500 pmol) | Ah 250 (500 pmol) |
| B | Ah 202 (1 pmol) | Ah 156 (5 pmol) | Ah 154 (5 pmol) | Ah 249 (500 pmol) | |
| C | Ah 202 (0.01 pmol) | Ah 251 (0.05 pmol) | Ah 256 (0.05 pmol) | Ah 249 (5 pmol) | Ah 257 (5 pmol) |
| D | Ah 202 (0.01 pmol) | Ah 251 (0.05 pmol) | Ah 256 (0.05 pmol) | Ah 249 (5 pmol) | |
| E | Ah 202 (1 pmol) | Ah 251 (5 pmol) | Ah 154 (5 pmol) | | |
| F | Ah 202 (1 pmol) | Ah 251 (5 pmol) | Ah 154 (5 pmol) | Ah 249 (500 pmol) | Ah 263 (500 pmol) |

Anneal from 80° C. to 20° C. (−1° C./30 sek) for A-D and from 80° C. to 20° C. (−1° C./1 min) for E and F. E and F is diluted 100 times after annealing in buffer B. Then add 5 µl 500 mM DMT-MM (Prepared according to Kunishima et al. *Tetrahedron* (2001), 57, 1551) dissolved in H$_2$O. Incubate at various temperatures o/n, then analyze by 10% urea polyacrylamide gel electrophoresis.

Figure 17:
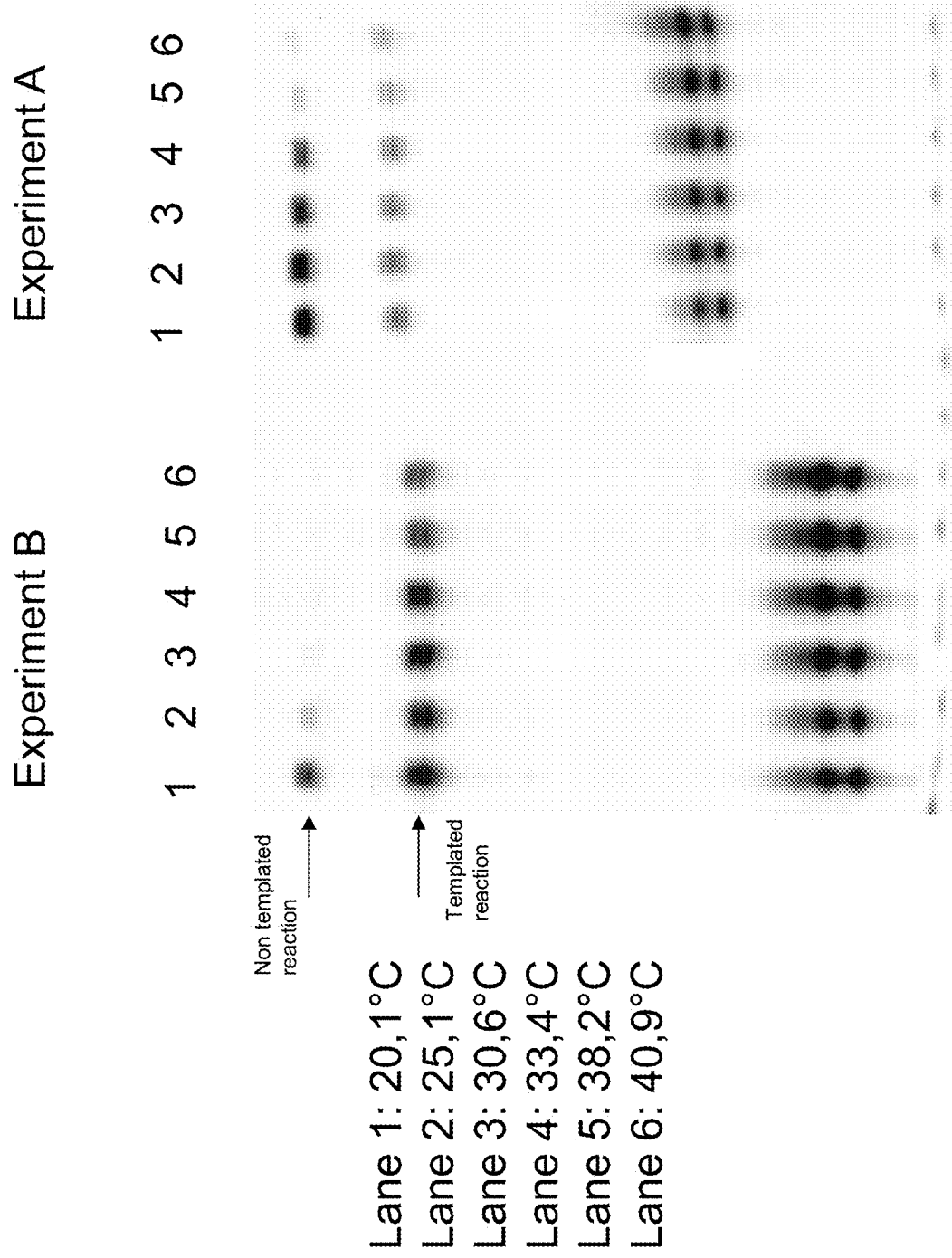
FIG. 17 shows the results of experiment A and B in example 15.
Figure 18:
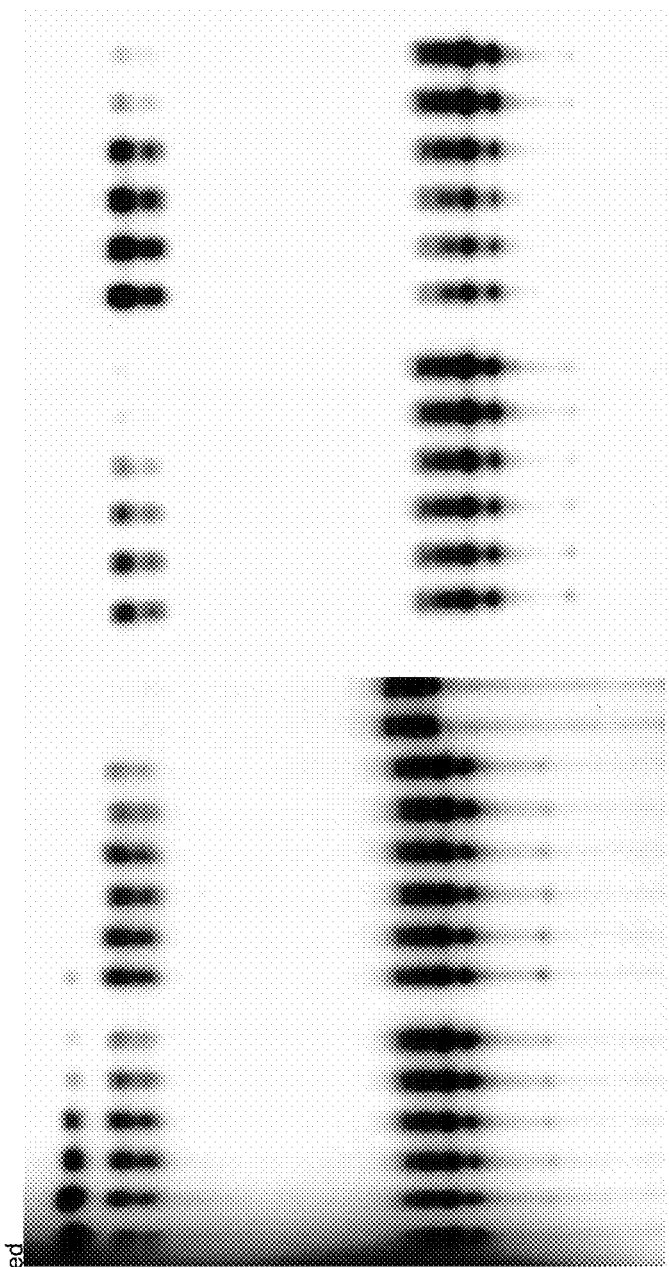
FIG. 18 shows the results of experiment D, E, and F reported in Example 16.

The results are shown in FIG. 17 (Experiment A and B) and FIG. 18 (Experiment C, D, E and F).

Conclusions

A templated-independent reaction is often observed at 20° C. This artefact is presumably not mediated by the zipper box in the template, as it is observed even when the competitor template (carrying the zipper box) is not included in the incubation mixture (see e.g. FIG. 17, exp. B, lane 1). Annealing at a high concentration, followed by dilution and reaction at the resulting low concentration eliminates template independent reactions, but maintains efficient annealing of building block oligos at the template prior to the reaction step (compare the efficient cross-linking and the absence of template independent reaction of experiments E and F with the less attractive experiments A, B, C and D).

Example 16

In order to examine the effect of the zipper box in set-up B, when the building block is annealed at position 3, an experiment was performed using two different building block oligos, one of which has a 6-meric zipper box (six nucleotides of the building block oligo anneals to the complementary zipper box on the template), and one of which has no zipper box.

Experimental

Mix 10 µl Buffer A, relevant oligos in various concentrations (See table II, below), and add H$_2$O to 50 µl.

TABLE XI

| Experiment | Oligo 1 ($^{32}$P-labelled) (BB1) | Oligo 2 (BB0) | Oligo 3 (Template) | Oligo 4 (Competitor oligo) |
|---|---|---|---|---|
| A | Ah 202 (0.01 pmol) | Ah 156 (0.05 pmol) | Ah 256 (0.05 pmol) | Ah 249 (5 pmol) |
| B | Ah 261 (0.01 pmol) | Ah 252 (0.05 pmol) | Ah 256 (0.05 pmol) | Ah 260 (5 pmol) |

Anneal from 80° C. to 20° C. (−1° C./30 sek). Then add 5 µl 500 mM DMT-MM (Prepared according to Kunishima et al. *Tetrahedron* (2001), 57, 1551) dissolved in H$_2$O. Incubate at various temperatures o/n, then analyze by 10% urea polyacrylamide gel electrophoresis.

Figure 19:
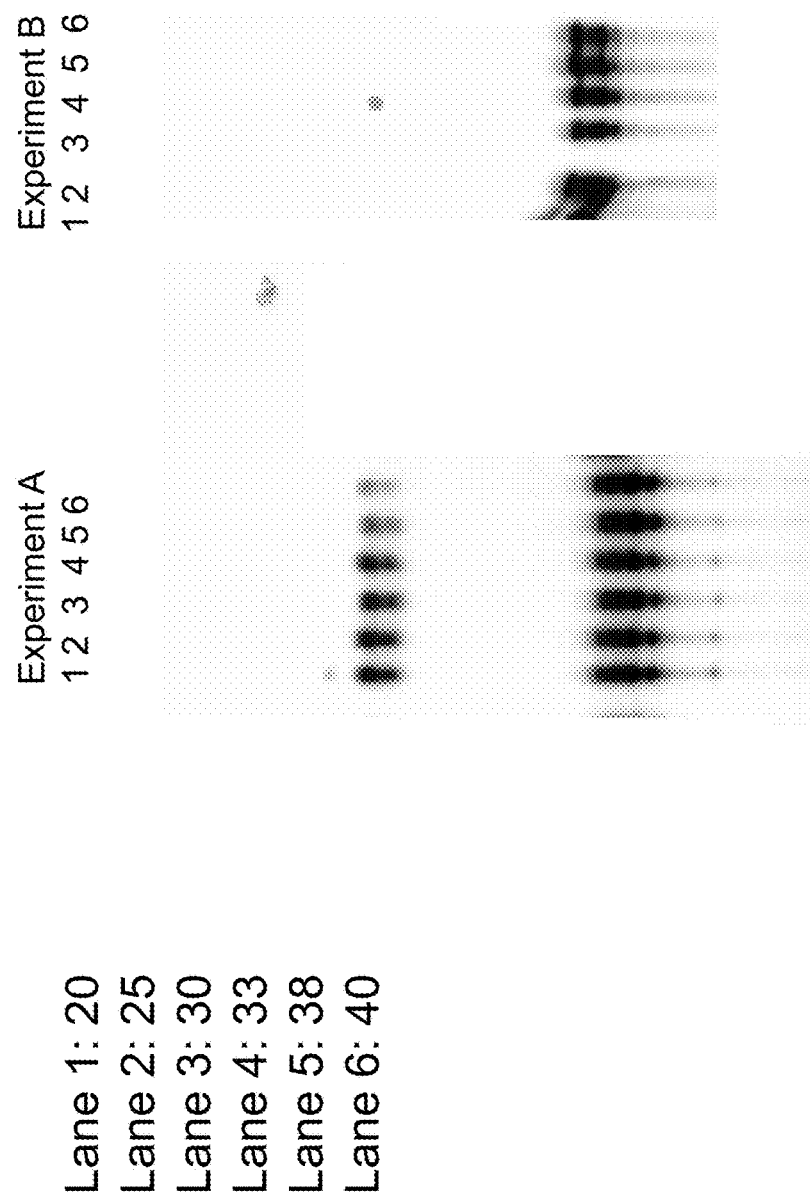
FIG. 19 discloses the results of experiment A and B reported in example 17.

The results are shown in FIG. 19.

Conclusions

Experiment A employs a building block carrying a 6-meric zipper box, and a cross-linking efficiency of about 30% is observed (experiment A, lane 2-4). When a building block without a zipper box is employed (experiment B), no cross-linking is observed (the spot in lane 3-4 is an artefact on the film, and does not represent a cross-link). No cross-linking is observed, and even at 20° C. no reaction is observed (possibly because the building block does not carry a zipper box)

Example 17

We examined the cross-linking efficiency using zipper box lengths of 5, 6 or 7 nucleotides, in set-up B, using building blocks that anneal at position 3.

Experimental

Mix 10 μl Buffer A, relevant oligos in various concentrations (See table XII, below), and add H₂O to 50 μl.

TABLE XII

| Experiment | Oligo 1 ($^{32}$P-labelled) (BB1) | Oligo 2 (BB0) | Oligo 3 (Template) | Oligo 4 (Competitor oligo) | Oligo 5 (Competitor template) |
|---|---|---|---|---|---|
| A | Ah 262 (1 pmol) | Ah 252 (5 pmol) | Ah 154 (5 pmol) | | |
| B | Ah 262 (1 pmol) | Ah 252 (5 pmol) | Ah 154 (5 pmol) | Ah 260 (500 pmol) | Ah 263 (500 pmol) |
| C | Ah 202 (1 pmol) | Ah 251 (5 pmol) | Ah 154 (5 pmol) | | |
| D | Ah 202 (1 pmol) | Ah 251 (5 pmol) | Ah 154 (5 pmol) | Ah 249 (500 pmol) | Ah 263 (500 pmol) |
| E | Ah 255 (1 pmol) | Ah 252 (5 pmol) | Ah 154 (5 pmol) | | |
| F | Ah 255 (1 pmol) | Ah 252 (5 pmol) | Ah 154 (5 pmol) | Ah 260 (500 pmol) | Ah 263 (500 pmol) |

Anneal from 80° C. to 20° C. (−1° C./min.). Dilute 100 times in buffer B+50 mM DMT-MM (Prepared according to Kunishima et al. *Tetrahedron* (2001), 57, 1551). Incubate at various temperatures o/n, then analyze by 10% urea polyacrylamide gel electrophoresis.

Figure 20:
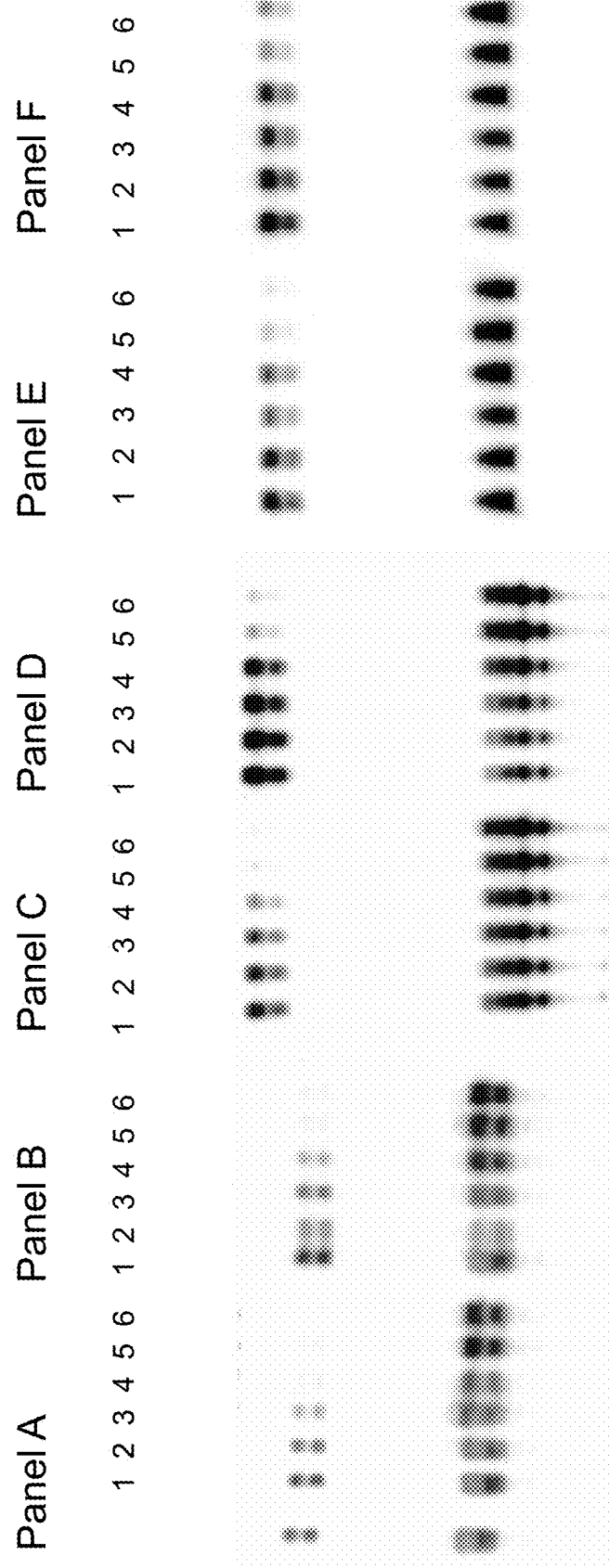
FIG. 20 discloses the results of example 17.

The results are shown in FIG. 20.

Conclusions

Zipper boxes of length 5, 6 or 7 nucleotides mediate efficient cross-linking in the temperature range 24-28° C. (FIG. 20, Panel A, C, E). Under these conditions (where the annealing is at high concentration and the cross-linking at low concentration), no cross-linking to the competitor complex is observed (FIG. 20, Panel B, D and F).

Example 18

In this experiment we analyzed the cross-linking efficiency of various linker lengths in set-up A (the linker connects the anti-codon and the zipper box).

Experimental

Mix 10 μl Buffer A, relevant oligos in various concentrations (See table XIII, below), and add H₂O to 50 μl.

TABLE XIII

| Experiment | Oligo 1 ($^{32}$P-labelled) (BB1) | Oligo 2 (BB0) | Oligo 3 (Template) |
|---|---|---|---|
| 1 | Ah 202 (1 pmol) | Ah 270 (10 pmol) | Ah 140 (5 pmol) |
| 2 | Ah 202 (1 pmol) | Ah 270 (10 pmol) | Ah 278 (5 pmol) |
| 3 | Ah 275 (1 pmol) | Ah 271 (10 pmol) | Ah 140 (5 pmol) |
| 4 | Ah 275 (1 pmol) | Ah 271 (10 pmol) | Ah 278 (5 pmol) |
| 5 | Ah 240 (1 pmol) | Ah 236 (10 pmol) | Ah 140 (5 pmol) |
| 6 | Ah 240 (1 pmol) | Ah 236 (10 pmol) | Ah 278 (5 pmol) |
| 7 | Ah 240 (1 pmol) | Ah 236 (10 pmol) | |
| 8 | Ah 272 (1 pmol) | Ah 270 (10 pmol) | Ah 140 (5 pmol) |
| 9 | Ah 272 (1 pmol) | Ah 270 (10 pmol) | Ah 278 (5 pmol) |
| 10 | Ah 273 (1 pmol) | Ah 271 (10 pmol) | Ah 140 (5 pmol) |
| 11 | Ah 273 (1 pmol) | Ah 271 (10 pmol) | Ah 278 (5 pmol) |
| 12 | Ah 274 (1 pmol) | Ah 236 (10 pmol) | Ah 140 (5 pmol) |
| 13 | Ah 274 (1 pmol) | Ah 236 (10 pmol) | Ah 278 (5 pmol) |
| 14 | Ah 274 (1 pmol) | Ah 236 (10 pmol) | |
| 15 | Ah 155 (1 pmol) | Ah 270 (10 pmol) | Ah 140 (5 pmol) |
| 16 | Ah 155 (1 pmol) | Ah 270 (10 pmol) | Ah 278 (5 pmol) |
| 17 | Ah 277 (1 pmol) | Ah 271 (10 pmol) | Ah 140 (5 pmol) |
| 18 | Ah 277 (1 pmol) | Ah 271 (10 pmol) | Ah 278 (5 pmol) |
| 19 | Ah 276 (1 pmol) | Ah 236 (10 pmol) | Ah 140 (5 pmol) |
| 20 | Ah 276 (1 pmol) | Ah 236 (10 pmol) | Ah 278 (5 pmol) |
| 21 | Ah 276 (1 pmol) | Ah 236 (10 pmol) | |

Anneal from 80° C. to 20° C. (−1° C./min.). Add 5 μl 500 mM DMT-MM (Prepared according to Kunishima et al. *Tetrahedron* (2001), 57, 1551). Incubate at 10° C. for 5 sec. and then 35° C. for 1 sec. Repeat o/n, then analyze by 10% urea polyacrylamide gel electrophoresis.

Figure 21:
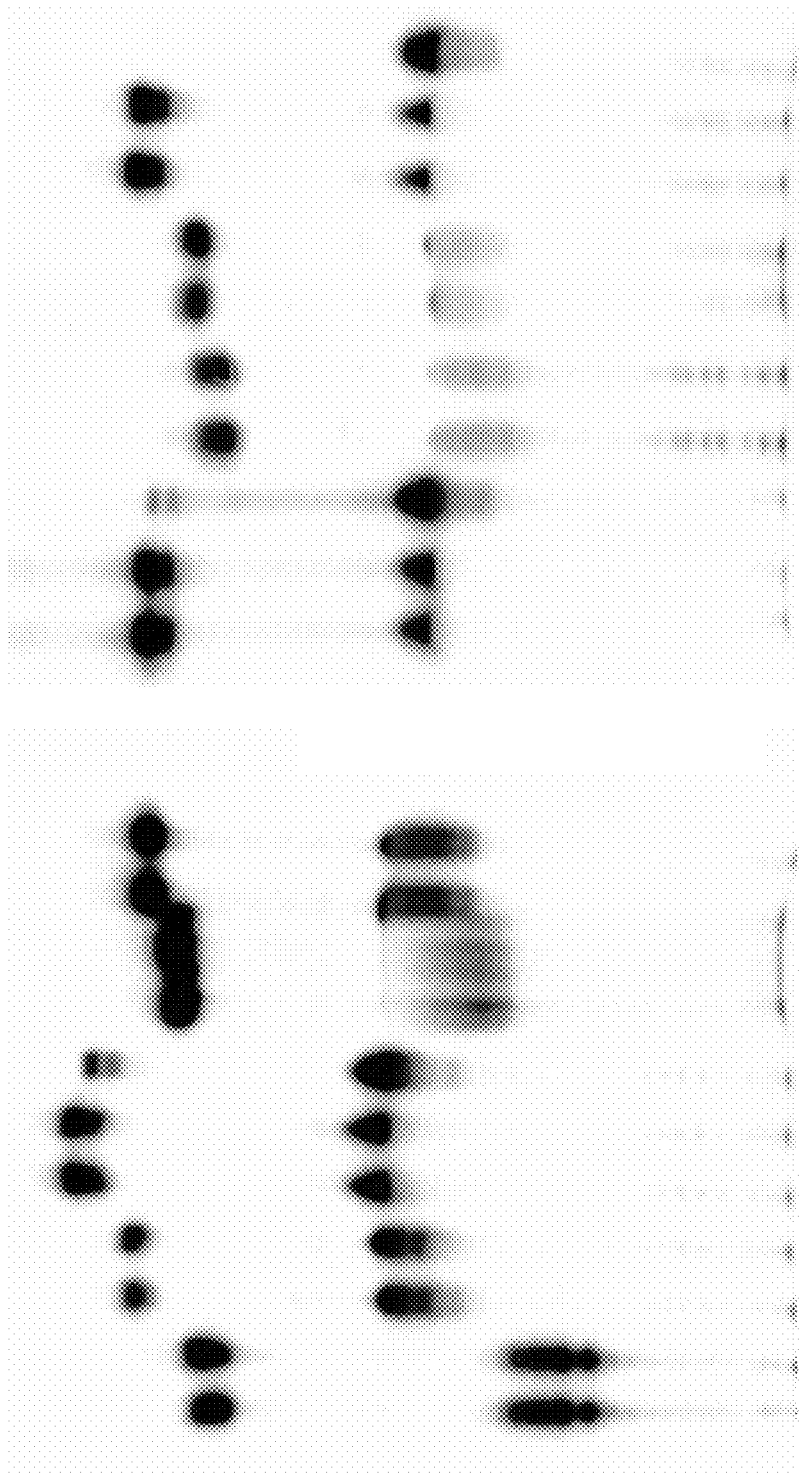
FIG. 21 shows the results of the experiments conducted in example 18.

The results are shown in FIG. 21.

Conclusions

Two aspects are examined: i) The influence of linker length on cross-linking efficiency (linker lengths 0, 2, and 5 nucleotides are examined), ii) The importance of spacing between the two reacting building blocks. FIG. 21, Lanes 1-6 involve a building block oligo annealed to position 3; Lane 7 involves the same building block, however, no template is present in lane 7. Lanes 8-13 involve a building block oligo annealed to position 2; lane 14 involve the same building block oligo, however, no template is present. Lanes 15-20 involve a building block oligo annealed to position 1; lane 21 involve the same oligo, and no template is present. Lanes 1, 3, 5, 8, 10, 12, 15, 17, 19 uses templates where the spacing between the bound building block oligos is one nucleotide larger than the templates used in experiments of lane 2, 4, 6, 9, 11, 13, 16, 18, and 20.

The optimal linker length as regards cross-linking efficiency is 0 nucleotides at all positions (FIG. 21, lanes 1, 2 for position 3; lanes 8, 9 for position 2; lanes 15, 16 for position. Separations of 0 or 1 nucleotides between building blocks bound to position 1 and 0, has no effect on the efficiency of cross-linking between the two building blocks (FIG. 21, compare e.g. lanes 1 and 2). Very high efficiencies of cross-linking are observed, from all three positions. Using a zipper box of 5 nucleotides, the reaction efficiency is approximately 50%, 95% and 95% when the building block oligo is annealed at position 3, 2 and 1 respectively, and the linker length is 0 nucleotides (FIG. 21, lanes 1, 2 and 8, 9 and 15, 16).

Example 19

In this example, in experiments 5, 8, 14 and 17, we analyzed the cross-linking efficiency of various linker lengths in set-up B.

Experimental

Mix 10 µl Buffer A, relevant oligos in various concentrations (See table XIV, below), and add H$_2$O to 50 µl.

TABLE XIV

| Experiment | Oligo 1 ($^{32}$P-labelled) (BB1) | Oligo 2 (BB0) | Oligo 3 (Template) |
|---|---|---|---|
| 1 | Ah 240 (5 pmol) | | |
| 2 | Ah 240 (5 pmol) | Ah 82 (10 pmol) | Ah 136 (10 pmol) |
| 3 | Ah 240 (5 pmol) | Ah 82 (10 pmol) | Ah 140 (10 pmol) |
| 4 | Ah 240 (5 pmol) | Ah 82 (10 pmol) | |
| 5 | Ah 240 (5 pmol) | Ah 156 (10 pmol) | Ah 154 (10 pmol) |
| 6 | Ah 240 (5 pmol) | Ah 156 (10 pmol) | |
| 7 | Ah 202 (5 pmol) | | |
| 8 | Ah 202 (5 pmol) | Ah 156 (10 pmol) | Ah 154 (10 pmol) |
| 9 | Ah 203 (5 pmol) | Ah 156 (10 pmol) | |
| 10 | Ah 203 (5 pmol) | | |
| 11 | Ah 203 (5 pmol) | Ah 156 (10 pmol) | Ah 154 (10 pmol) |
| 12 | Ah 203 (5 pmol) | Ah 156 (10 pmol) | |
| 13 | Ah 36 (5 pmol) | | |
| 14 | Ah 36 (5 pmol) | Ah 156 (10 pmol) | Ah 154 (10 pmol) |
| 15 | Ah 36 (5 pmol) | Ah 156 (10 pmol) | |
| 16 | Ah 142 (5 pmol) | | |
| 17 | Ah 142 (5 pmol) | Ah 156 (10 pmol) | Ah 154 (10 pmol) |
| 18 | Ah 142 (5 pmol) | Ah 156 (10 pmol) | |

Anneal from 80° C. to 20° C. (−1° C./min.). Add 5 µl 500 mM DMT-MM (Prepared according to Kunishima et al. *Tetrahedron* (2001), 57, 1551). Incubate at 10° C. for 5 sec. and then 35° C. for 1 sec. Repeat o/n, then analyze by 10% urea polyacrylamide gel electrophoresis.

Figure 22:
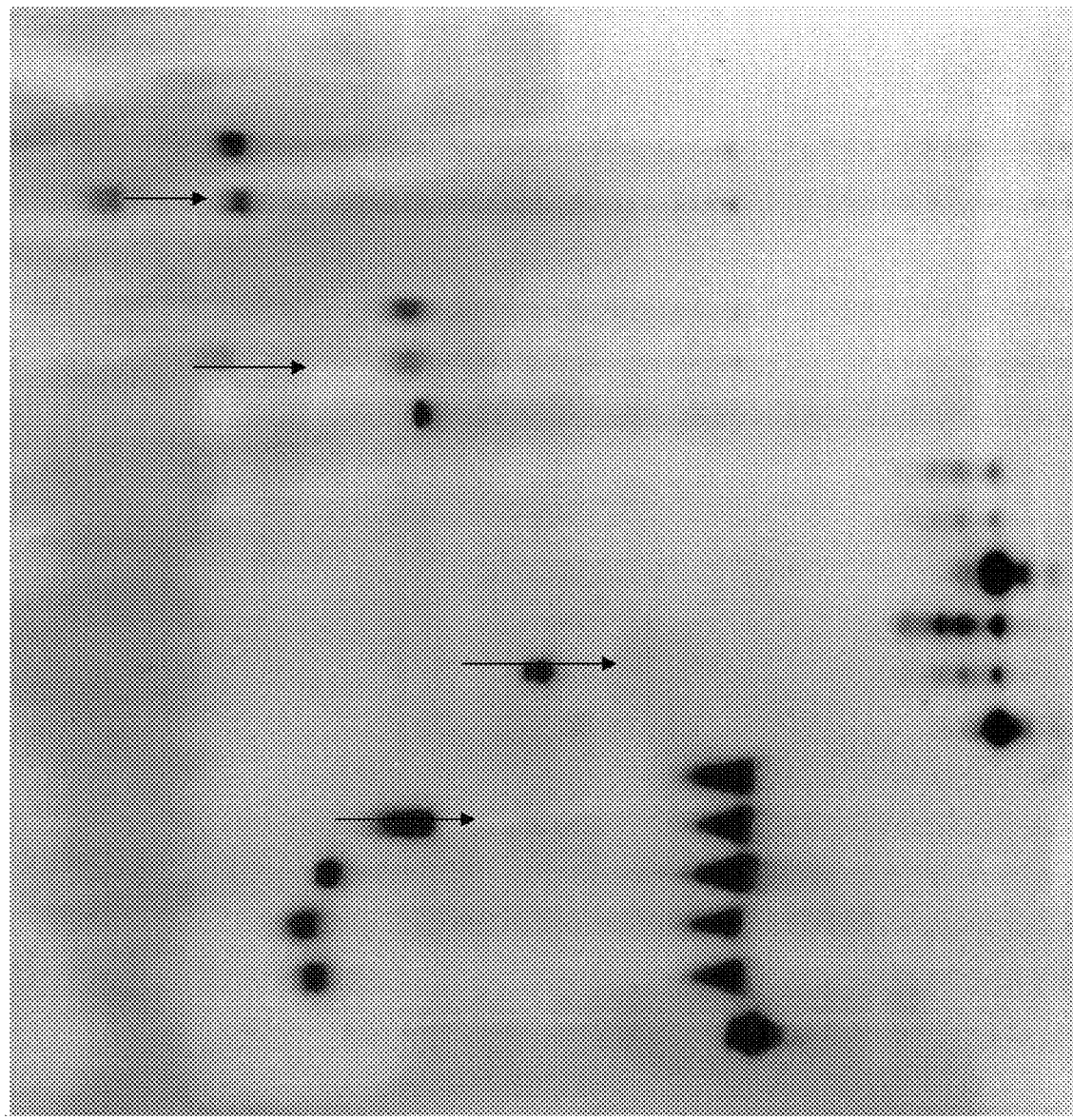
FIG. 22 shows the results of the experiments disclosed in example 19.

The results are shown in FIG. 22.

Conclusions

The experiments measure reaction efficiency between a building block oligo bound at position 3 in the oligo setup B. Linker lengths of 0, 5, 30 and 50 nucleotides mediates reaction efficiencies of appr. 90% (lane 8), 50% (lane 5), 20-40% (lane 14) and 20-40% (lane 17) respectively. In other words, a linker length of 0 nucleotides is optimal for set-up B, as was also observed for set-up A. In setup B reaction efficiencies from position 2 and position 1 of approximately 75% and 90% have been achieved (data not shown).

Example 20

We tested the extent of template-independent reactions at various temperatures, using zipper box lengths of 5, 6, 7, or 8 nucleotides, under conditions where template-independent reactions are observed (i.e., both annealing and reaction is done at high template and building block concentrations).

Experimental

Mix 2 µl Buffer A, relevant oligos in various concentrations (See table XV, below), and add H$_2$O to 10 µl.

TABLE XV

| Experiment | Oligo 1 ($^{32}$P-labelled) (BB1) | Oligo 2 (BB0) | Oligo 3 (Template) |
|---|---|---|---|
| A | Ah 36 (2 pmol) | Ah 51 (10 pmol) | Ah 38 (10 pmol) |
| B | Ah 36 (2 pmol) | Ah 51 (10 pmol) | |
| C | Ah 36 (2 pmol) | Ah 133 (10 pmol) | Ah 38 (10 pmol) |
| D | Ah 36 (2 pmol) | Ah 133 (10 pmol) | |
| E | Ah 36 (2 pmol) | Ah 134 (10 pmol) | Ah 38 (10 pmol) |
| F | Ah 36 (2 pmol) | Ah 134 (10 pmol) | |
| G | Ah 36 (2 pmol) | Ah 135 (10 pmol) | Ah 38 (10 pmol) |
| H | Ah 36 (2 pmol) | Ah 135 (10 pmol) | |

Anneal from 80° C. to 20° C. (−1° C./min.). Add 1 µl 500 mM DMT-MM (Prepared according to Kunishima et al. *Tetrahedron* (2001), 57, 1551). Incubate at various temperatures o/n, then analyze by 10% urea polyacrylamide gel electrophoresis.

Figure 23:
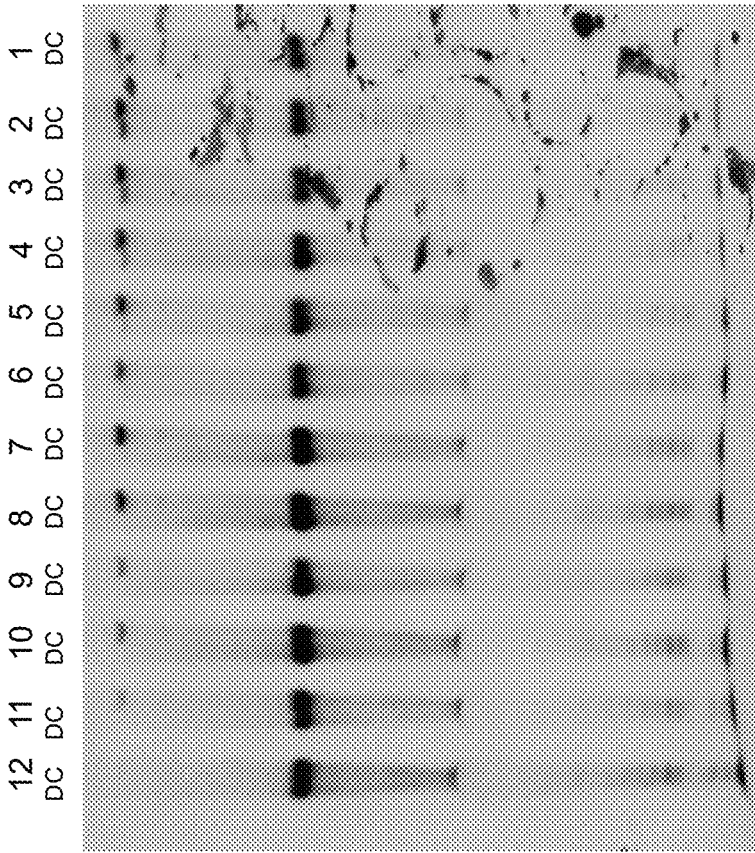
FIG. 23 shows the results of Experiments A to B reported in example 20.

The results are shown in FIGS. 23 and 24.

Conclusions

Using a 5-meric zipper box (experiments A and B), no template-independent reaction is observed for temperatures between 9.9° C. and 50.8° C. (FIG. 23, lanes 1-12). Using a zipperbox of length 6, 7, or 8 nucleotides, a template-independent reaction is observed in the temperature range of 5-28° C., 5-32° C., and 5-35° C., respectively. When performing templated reactions that cannot be initiated by the experimenter (e.g. by addition of reagent), it is therefore recommended to perform annealing and reaction at a temperature that does not lead to template-independent reaction (e.g. 25° C., 30° C., 34° C., and 37° C. for zipper box lengths of 5-, 6-, 7-, and 8-nucleotides, respectively).

When performing reactions that can be initiated by the experimenter (e.g. by addition of reagent or UV-exposure) the complexes may be formed at lower temperatures, to ensure high degree of zipper box-zipper box complex formation, where after excess building block-oligos may be removed by washing, and then the reaction can be initiated. Because of the lower concentration of building block-oligos after the wash, the template-independent reaction will be much less significant.

Example 21

In a multistep procedure (where the building block-oligos are added to the template scaffold complex and reacted one at a time), it is important that the oligos (used in the previous step, and still bound to the template) do not interfere with the reaction of the last added building block-oligo.

We here examine whether the efficiency of cross-linking between building block oligos bound at position 2 and position 0 is affected by building block oligos bound at position 3, in both set-up A and B.

Experimental

Mix 10 µl Buffer A, relevant oligos in various concentrations (See table XVI, below), and add H$_2$O to 50 µl.

TABLE XVI

| Experiment | Oligo 1 ($^{32}$P-labelled) (BB1) | Oligo 1+ | Oligo 2 (BB0) | Oligo 3 (Template) | Oligo 4 (Competitor oligo) | Oligo 5 (Competitor template) |
|---|---|---|---|---|---|---|
| A | Ah 258 (1 pmol) | Ah 202 (10 pmol) | Ah 252 (10 pmol) | Ah 154 (5 pmol) | | |
| B | Ah 258 (1 pmol) | | Ah 252 (10 pmol) | Ah 154 (5 pmol) | | |
| C | Ah 258 (1 pmol) | Ah 202 (10 pmol) | Ah 252 (10 pmol) | Ah 154 (5 pmol) | Ah 260 (10 pmol) | Ah 279 (5 pmol) |
| D | Ah 258 (1 pmol) | | Ah 252 (10 pmol) | Ah 154 (5 pmol) | Ah 260 (10 pmol) | Ah 279 (5 pmol) |
| E | Ah 272 (1 pmol) | Ah 255 (10 pmol) | Ah 270 (10 pmol) | Ah 140 (5 pmol) | | |
| F | Ah 272 (1 pmol) | | Ah 270 (10 pmol) | Ah 140 (5 pmol) | | |

Anneal from 80° C. to 30° C. (−1° C./min.) without BB1. Add BB1 and anneal again from 55° C. to 30° C. (−1° C./min). Dilute 100 times in buffer B+50 mM DMT-MM (Prepared according to Kunishima et al. *Tetrahedron* (2001), 57, 1551). Incubate at 30° C. o/n for A to D, and at 10° C. for 5 sec and then 35° C. for 1 sec repeat o/n for E and F, then analyze by 10% urea polyacrylamide gel electrophoresis.

Figure 25:
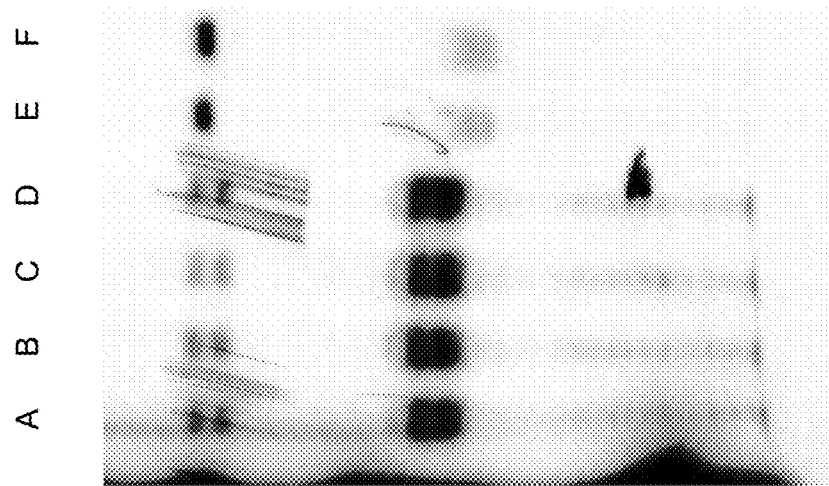
FIG. 25 shows the results of example 21.

The results are shown in FIG. 25.

CONCLUSIONS

An occupied position 3 does not interfere with the cross-linking of building blocks bound at position 2 and 0 (FIG. 25, compare lane A with lane B, lane C with lane D, lane E with F).

---

The invention claimed is:

1. A library comprising a plurality of different scaffolded molecules comprising a scaffold connected to a plurality of functional entities, wherein the scaffolded molecule is covalently linked to an identifier oligonucleotide comprising a first plurality of oligonucleotide sequences and a second plurality oligonucleotide sequences comprising oligonucleotide sequences complementary to the first plurality of oligonucleotide sequences, wherein the first plurality is covalently linked to the second plurality and each of the first and second plurality identifies the scaffolded molecule and further wherein the library comprises at least $10^3$ different scaffolded molecules.

2. The library according to claim 1, wherein the identifier oligonucleotide comprises nucleotide monomers composed of a nucleobase and a backbone moiety.

3. The library according to claim 2, wherein the nucleobases of the nucleotide monomers are naturally occurring nucleobases.

4. The library according to claim 2, wherein the identifier oligonucleotide comprises nucleotide monomers comprising naturally occurring nucleobases and nucleotide monomers comprising non-natural nucleobases.

5. The library according to claim 4, wherein the nucleotide monomers comprise nucleobases selected from the group consisting of purine and pyrimidine hetero cycles and heterocyclic analogues and tautomers thereof.

6. The library according to claim 4, wherein the nucleotide monomers comprise nucleobases selected from the group consisting of adenine, 8-oxo-$N^6$-methyladenine;

guanine, isoguanine, 7-deazaguanine;

cytosine, isocytosine, pseudoisocytosine, $N^4,N^4$-ethano-cytosine, 5-methylcytosine, 5-($C^3$-$C^6$)-alkynylcytosine;

thymine;

uracil, 5-bromouracil, 5-fluorouracil;

inosine;

purine, diaminopurine, $N^6,N^6$-ethano-2,6-diamino-purine;

xanthine, 7-deazaxanthine;

pyrimidine and 2-hydroxy-5-methyl-4-triazolopyridine; and heterocyclic analogues and tautomers thereof.

7. The library according to claim 2, wherein the nucleotide monomers comprise backbone moieties selected from the group consisting of

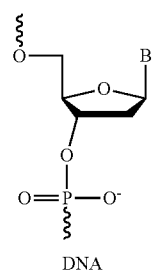
DNA

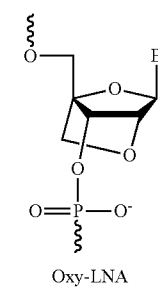
Oxy-LNA

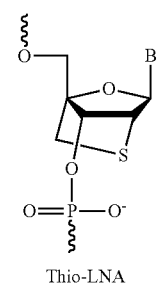
Thio-LNA

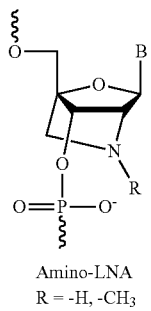
Amino-LNA
R = -H, -CH$_3$

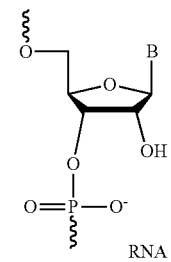
RNA

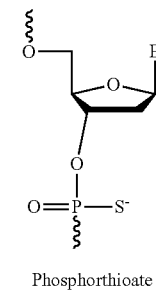
Phosphorthioate

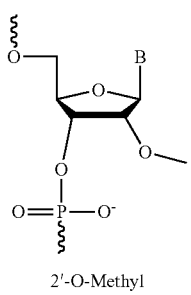
2'-O-Methyl

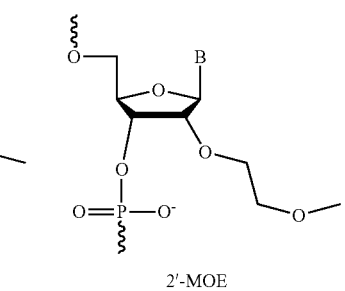
2'-MOE

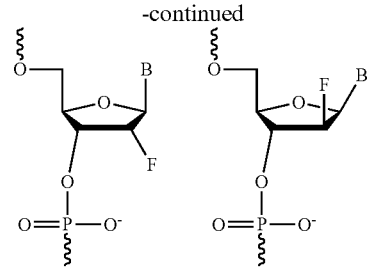
2'-Fluoro          2'-F-ANA

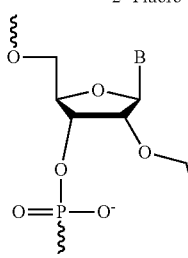
2'-AP

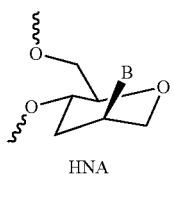
HNA

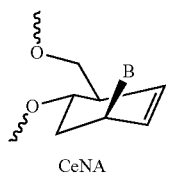
CeNA

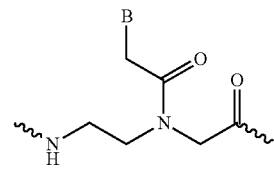
PNA

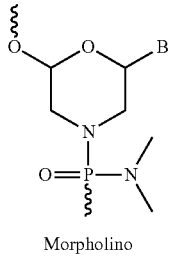
Morpholino

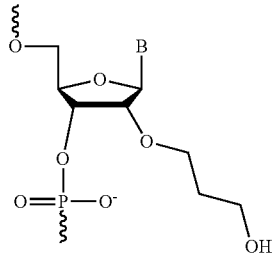
2'-(3-hydroxy)propyl

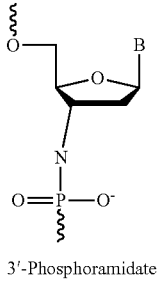
3'-Phosphoramidate

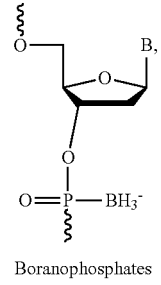
Boranophosphates wherein B denotes the nucleobase of the nucleotide monomer.

8. The library according to claim 2, wherein the nucleotide monomers comprise backbone moieties comprising a pentose sugar moiety and an internucleoside linker.

9. The library according to claim 8, wherein the pentose sugar moiety is selected from the group consisting of ribose, 2'-deoxyribose, 2'-O-methyl-ribose, 2'-flour-ribose, and 2'-4'-O-methylene-ribose, and wherein the nucleobase is attached to the 1' position of the pentose sugar moiety.

10. The library according to claim 8, wherein the internucleoside linker connects the 3' end of a preceding pentose monomer to the 5' end of a succeeding pentose monomer.

11. The library according to claim 10, wherein the internucleoside linker is selected from the group of consisting of phosphodiester linkers, phosphorothioate linkers, methylphosphonate linkers, phosphoramidate linkers, phosphotriester linkers, phosphodithioate linkers, and internucleoside linkers not containing phosphorous.

12. The library according to claim 2, wherein the identifier oligonucleotide comprises nucleosides selected from the group consisting of deoxyadenosine, deoxyguanosine, deoxythymidine, and deoxycytidine, and wherein said nucleosides are connected through phosphodiester linkers.

13. The library according to claim 2, wherein the identifier oligonucleotide comprises nucleosides selected from the group consisting of adenosine, guanosine, uridine, cytidine, and inosine, and wherein said nucleosides are connected through phosphodiester linkers.

14. The library according to claim 2, wherein the identifier oligonucleotide comprises nucleosides selected from a first group consisting of deoxyadenosine, deoxyguanosine, deoxythymidine, and deoxycytidine, and nucleosides selected from a second group consisting of adenosine, guanosine, uridine, cytidine, and inosine, wherein said nucleosides are connected through through a phosphodiester linker.

15. The library of claim 1, wherein the library comprises from about $10^3$ to about $10^{12}$ different scaffolded molecules.

16. The library of claim 15, wherein the scaffolded molecules are small molecules.

17. The library of claim 15, wherein the oligonucleotide sequences in the second plurality of oligonucleotide sequences are covalently linked.

18. The library of claim 15, wherein the oligonucleotide identifier comprises one or more single stranded oligonucleotide sequences.

19. The library of claim 15, wherein the oligonucleotide identifier comprises double stranded oligonucleotide sequences.

20. The library of claim 15 wherein each of the first plurality and the second plurality of oligonucleotide sequences contain an oligonucleotide sequence identifying the scaffold.

21. The library of claim 15 wherein the scaffold is connected to at least two of the plurality of functional entities through a different reactive group on the scaffold or at a different position on the scaffold previously occupied by a reactive group.

22. A library comprising a plurality of different scaffolded molecules comprising
a scaffold connected to two or more functional entities, wherein the scaffolded molecule is covalently linked to an identifier oligonucleotide comprising
a plurality of codons and a plurality of anticodons comprising oligonucleotide sequences complementary to the plurality of codons, wherein the plurality of codons is covalently linked to the plurality of anticodons, and each of the plurality of codons and the plurality of anti-codons identifies the scaffolded molecule, and wherein at least two of the functional entities are connected to different reactive groups on the scaffold or different positions on the scaffold previously occupied by reactive groups.

23. The library of claim 22, wherein the library comprises from about $10^3$ to about $10^{12}$ different scaffolded molecules.

24. The library according to claim 23, wherein the scaffolded molecules are small molecules.

25. The library according to claim 23, wherein the scaffolded molecules are selected from the group consisting of monofunctional, difunctional, trifunctional and oligofunctional, open-chain hydrocarbons;
monocyclic, bicyclic, tricyclic and polycyclic hydrocarbons,
bridged polycyclic hydrocarbons;
monofunctional, difunctional trifunctional and oligofunctional, non-aromatic carbocycles;
monofunctional, difunctional, trifunctional and oligofunctional, aromatic carbocycles;
monocyclic, bicyclic, tricyclic and polycyclic, aromatic carbocycles;
monofunctional, difunctional, trifunctional and oligofunctional, non-aromatic heterocycles;
monofunctional, difunctional, trifunctional and oligofunctional, aromatic heterocycles;
monocyclic, bicyclic, tricyclic and polycyclic heterocycles; and
bridged polycyclic heterocycles.

26. The library of claim 23, wherein anti-codons in the plurality of anti-codons are covalently linked.

27. The library of claim 22, wherein the oligonucleotide identifier comprises one or more single stranded oligonucleotide sequences.

28. The library of claim 22 wherein the oligonucleotide identifier comprises double stranded oligonucleotide sequences.

29. The library of claim 22, wherein one or more of the different scaffolded molecules comprises a core structure connected to the two or more functional entities, wherein at least two of the functional entities are connected to different reactive groups on the core structure or different positions on the core structure previously occupied by reactive groups.

30. The library of claim 22 wherein each of the plurality of codons and the plurality of anti-codons contains an oligonucleotide sequence identifying the scaffold.

31. The library of claim 22 wherein the scaffold is connected to each of the functional entities through a different reactive group on the scaffold or a different position on the scaffold previously occupied by a reactive group.

32. The library according to claim 22, wherein one or more scaffolded molecules are covalently linked to an identifier oligonucleotide through a linker comprising polyethylene glycol (PEG).

33. The library according to claim 22, wherein the identifier oligonucleotide comprises nucleotide monomers comprising naturally occurring nucleobases and nucleotide monomers comprising non-natural nucleobases.

34. The library according to claim 33, wherein the nucleotide monomers comprise nucleobases selected from the group consisting of
adenine, 8-oxo-$N^6$-methyladenine;
guanine, isoguanine, 7-deazaguanine;
cytosine, isocytosine, pseudoisocytosine, $N^4,N^4$-ethanocytosine,
5-methylcytosine, 5-($C^3$-$C^6$)-alkynylcytosine;
thymine;
uracil, 5-bromouracil, 5-fluorouracil;
inosine;
purine, diaminopurine, $N^6,N^6$-ethano-2,6-diamino-purine;
xanthine, 7-deazaxanthine;
pyrimidine and 2-hydroxy-5-methyl-4-triazolopyridine; and
heterocyclic analogues and tautomers thereof.

35. The library according to claim 33, wherein the nucleotide monomers comprise backbone moieties selected from the group consisting of

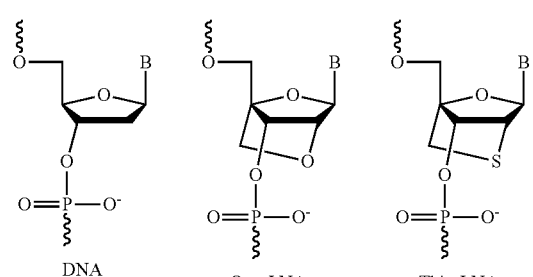
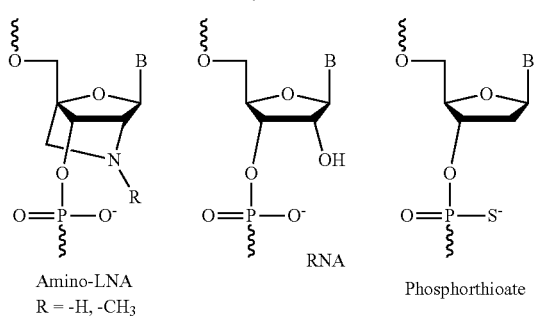
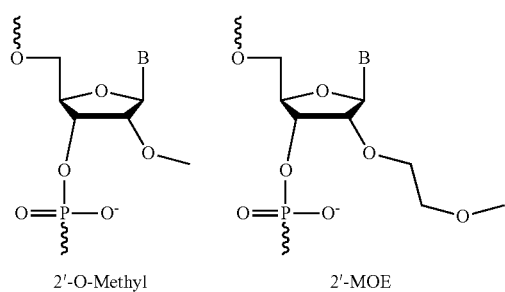
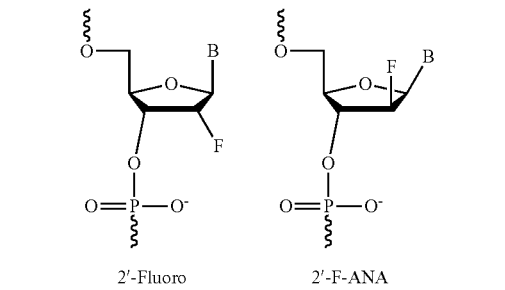
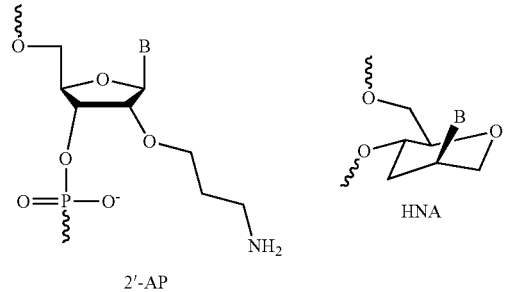
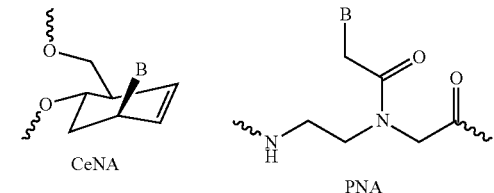

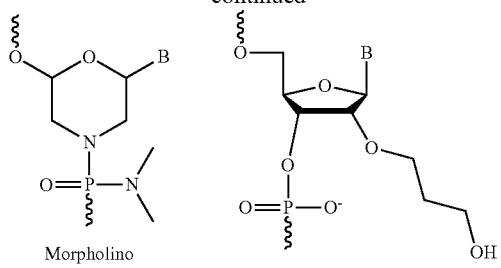
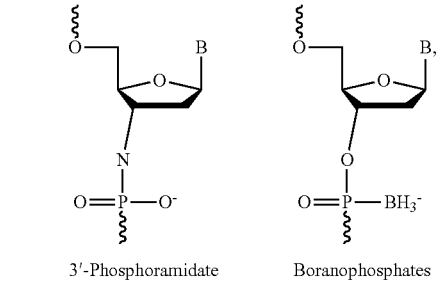

wherein B denotes the nucleobase of the nucleotide monomer.

36. The library according to claim 33, wherein the nucleotide monomers comprise backbone moieties comprising a pentose sugar moiety and an internucleoside linker.

37. The library according to claim 36, wherein the internucleoside linker is selected from the group of consisting of phosphodiester linkers, phosphorothioate linkers, methylphosphonate linkers, phosphoramidate linkers, phosphotriester linkers, phosphodithioate linkers, and internucleoside linkers not containing phosphorous.

38. A method for selecting scaffolded molecules from the library of different scaffolded molecules of claim 22, the method comprising:
(1) exposing the library to conditions enriching the library with complexes having a predetermined activity toward a biological target;
(2) amplifying the complexes of the enriched library;
(3) optionally repeating steps (1) and (2); and
(4) obtaining an enriched library having a higher ratio of scaffolded molecules with the predetermined activity.

39. The library according to claim 22, wherein the scaffolded molecules are not polynucleotides.

40. The library according to claim 15, wherein the number of different scaffolded molecules in the library is at least $10^6$.

41. The library according to claim 15, wherein one or more scaffolded molecules are covalently linked to an identifier oligonucleotide through a linker comprising polyethylene glycol (PEG).

42. The library according to claim 15, wherein the scaffolded molecules are not polymeric molecules.

43. The library according to claim 15, wherein the scaffolded molecules are not polynucleotides.

44. The library according to claim 15, wherein the scaffolded molecules are selected from the group consisting of
monofunctional, difunctional, trifunctional and oligofunctional, open-chain hydrocarbons;
monocyclic, bicyclic, tricyclic and polycyclic hydrocarbons;
bridged polycyclic hydrocarbons;
monofunctional, difunctional trifunctional and oligofunctional, non-aromatic carbocycles;

monofunctional, difunctional, trifunctional and oligofunctional, aromatic carbocycles;

monocyclic, bicyclic, tricyclic and polycyclic, aromatic carbocycles;

monofunctional, difunctional, trifunctional and oligofunctional, non-aromatic heterocycles;

monofunctional, difunctional, trifunctional and oligofunctional, aromatic heterocycles;

monocyclic, bicyclic, tricyclic and polycyclic heterocycles; and bridged polycyclic heterocycles.

45. The library of claim 15, wherein one or more of the different scaffolded molecules comprise one or more core structures covalently linked to a plurality of functional entities.

46. A method for selecting scaffolded molecules from the library of different scaffolded molecules of claim 15, the method comprising:
(1) exposing the library to conditions enriching the library with complexes having a predetermined activity toward a biological target;
(2) amplifying the complexes of the enriched library;
(3) optionally repeating steps (1) and (2); and
(4) obtaining an enriched library having a higher ratio of scaffolded molecules with the predetermined activity.

47. The library of claim 45 wherein the core structure is connected at least two of the plurality of functional entities through a different reactive group on the core structure or at a different position on the core structure previously occupied by a reactive group.

* * * * *